United States Patent
Bottger et al.

(10) Patent No.: US 11,485,751 B2
(45) Date of Patent: Nov. 1, 2022

(54) APRAMYCIN DERIVATIVES

(71) Applicants: WAYNE STATE UNIVERSITY, Detroit, MI (US); UNIVERSITAT ZURICH, Zurich (CH)

(72) Inventors: Erik C. Bottger, Zurich (CH); Sven N. Hobbie, Zurich (CH); Andrea Vasella, Zurich (CH); David Crich, Detroit, MI (US); Amr Sonousi, Detroit, MI (US); Takayuki Kato, Detroit, MI (US); Jonathan Quirke, Detroit, MI (US); Parasuraman Rajasekaran, Detroit, MI (US); Vikram Ashok Sarpe, Detroit, MI (US)

(73) Assignees: WAYNE STATE UNIVERSITY, Detroit, MI (US); UNIVERSITAT ZURICH, Zurich (CH)

( * ) Notice: Subject to any disclaimer, the term of this patent is extended or adjusted under 35 U.S.C. 154(b) by 167 days.

(21) Appl. No.: 16/609,788

(22) PCT Filed: May 1, 2018

(86) PCT No.: PCT/US2018/030447
§ 371 (c)(1),
(2) Date: Oct. 31, 2019

(87) PCT Pub. No.: WO2018/204358
PCT Pub. Date: Nov. 8, 2018

(65) Prior Publication Data
US 2020/0062793 A1  Feb. 27, 2020

Related U.S. Application Data

(60) Provisional application No. 62/492,474, filed on May 1, 2017.

(51) Int. Cl.
 - *C07H 5/06* (2006.01)
 - *C07H 15/232* (2006.01)
 - *C07H 15/224* (2006.01)

(52) U.S. Cl.
 CPC .............. *C07H 5/06* (2013.01); *C07H 15/224* (2013.01); *C07H 15/232* (2013.01)

(58) Field of Classification Search
 None
 See application file for complete search history.

(56) References Cited

U.S. PATENT DOCUMENTS

| 4,358,585 A | 11/1982 | Igarsahi et al. |
| 4,360,665 A | 11/1982 | Kirst |
| 2007/0225246 A1 | 9/2007 | Denu et al. |
| 2013/0016539 A1 | 6/2013 | Boettger et al. |
| 2013/0165397 A1* | 6/2013 | Boettger ............... A61P 11/00 514/36 |
| 2013/0203693 A1 | 8/2013 | Chaparian et al. |
| 2015/0352136 A1 | 12/2015 | Baasov et al. |

FOREIGN PATENT DOCUMENTS

| CA | 2993425 | 2/2017 |
| JP | 2013-537177 | 9/2013 |
| WO | 2017/018528 | 2/2017 |

OTHER PUBLICATIONS

Sati, GC et al., N6', N6''', and O4'-Modifications to Neomycin Affect Ribosomal Selectivity Without Compromising Antibacterial Activity, American Chemical Society Infectious Disease 3(5), pp. 1-24 (pp. 368-377), published online Apr. 6, 2017.
Duscha, S et al., Identification and Evaluation of Improved 4'-O-(Alkyl) 4, 5-Disubstituted 2-Deoxystreptamines as Next-Generation Aminoglycoside Antibiotics, Open-Access Online Research Article, vol. 5, Issue 5, pp. 1-10, 2014; Retrieved from the internet: URL:https://www.ncbi.nlm.nih.gov/pmc/articles/PMC4196235/pdf/mBio.-1827-14.pdf.
Pubchem CID 53652436, pp. 1-13, Create Date: Dec. 3, 2011; p. 4.
Pubchem CID 14139642, pp. 1-10, Create Date: Feb. 9, 2007; p. 3.
Abe et al.: "Aminoglycoside Antibiotics. Xiv Synthesis and Activity Of 6-0-(3-AMINO-3-DEOXY-a-D-G Lucopyranosyl)- and 5-0-(13-D-RIBOFURANOSYL)APRAMYCINS", the Journal of Antibiotics 34 (11) :1434-1446, 1981.

\* cited by examiner

*Primary Examiner* — Traviss C McIntosh, III
(74) *Attorney, Agent, or Firm* — JMB Davis Ben-David

(57) ABSTRACT

The invention relates to derivatives of apramycin-based aminoglycoside antibacterial drugs modified in positions C5 and/or C6 and O5 and/or O6. The modifications impart favourable properties regarding increased selectivity and retention of activity in the presence of resistance determinants of the AAC(3) class. The invention further relates to said compounds for use in the therapy of bacterial infection by systemic administration, especially in instances where the infection is caused by a pathogen comprising a resistance determinant of the AAC(3) class, in particular AAC(3)-IV.

14 Claims, 19 Drawing Sheets

APRAMYCIN DERIVATIVES

CROSS-REFERENCE TO RELATED APPLICATION

This is the U.S. National Stage of International Patent Application No. PCT/US2018/030447 filed on May 1, 2018, which was published in English under PCT Article 21(2), and which in turn claims priority to U.S. Provisional Patent Application No. 62/492,474 filed on May 1, 2017, which is incorporated herein by reference in its entirety as if fully set forth herein.

STATEMENT REGARDING FEDERALLY SPONSORED RESEARCH OR DEVELOPMENT

This invention was made with government support under grant 1R01AI123352-01 awarded by the National Institutes of Health. The government has certain rights in the invention.

FIELD OF THE DISCLOSURE

The present invention relates to aminoglycoside compounds based on the apramycin scaffold having improved antibacterial properties. The invention further relates to use of the compounds of the invention in the treatment of infections by pathogens carrying certain resistance genes rendering such pathogens refractive to classical aminoglycoside antibacterial drugs.

BACKGROUND OF THE DISCLOSURE

The clinically important class of aminoglycoside antibiotics (AGAs) derive their activity from binding to bacterial ribosomal RNA. Aminoglycosides are an important class of broad spectrum antibiotics owing to the combination of their high potency, lack of allergic response, and minimal effect on the host's microbiome. AGAs currently in clinical practice, however, are compromised by toxicity issues (mainly irreversible ototoxicity) and the rise of resistant pathogens. No new aminoglycosides have been introduced into clinical practice since the early 1990s. There is therefore an unmet need for new aminoglycoside drugs that retain their favorable characteristics yet overcome the now widespread resistance determinants and do so without significant toxicity.

Apramycin is an unusual monosubstituted 2-deoxystreptamine (DOS) type aminoglycoside antibiotic that is currently being evaluated as a possible clinical candidate for the treatment of carbapenem resistant enterobacteriaceae (CREs). Apramycin has the advantage over other AGAs currently in clinical use of displaying little ototoxicity. Furthermore, its unusual structure safeguards it from susceptibility to many of the aminoglycoside modifying enzymes (AMEs) that act on the various AGAs in clinical use and from susceptibility to the ribosomal methyl transferase ArmA that modifies the target ribosome and destroys the activity of all members of the 4,6-class of disubstituted DOS AGAs. Apramycin is however susceptible to aminoglycoside acetyltransferases (AAC) of the AAC(3) class, including the enzyme AAC(3)-IV.

Based on the above-mentioned state of the art, the objective of the present invention is to provide improved apramycin derivatives that overcome the problems found in the prior art. This objective is attained by the claims of the present specification.

DESCRIPTION

Many aminoglycoside antibiotic drug candidates have been developed over more than 50 years, and a vast number of synthetic approaches are known to the skilled artisan. Useful reviews of modern aminoglycoside chemistry are available in Wang and Chang, Aminoglycoside Antibiotics: From Chemical Biology to Drug Discovery, $2^{nd}$ Ed. (Editor: D. Arya), Wiley 2007, and in Berkov-Zrihen and Fridman, Modern Synthetic Methods in Carbohydrate Chemistry (Editors: D. B. Werz and S. Vidal) with the latter covering protecting group strategies in the apramycin class.

Apramycin is a monosubstituted 2 deoxystreptamine (DOS) type aminoglycoside antibiotic (AGA) characterized by the following formula (1)

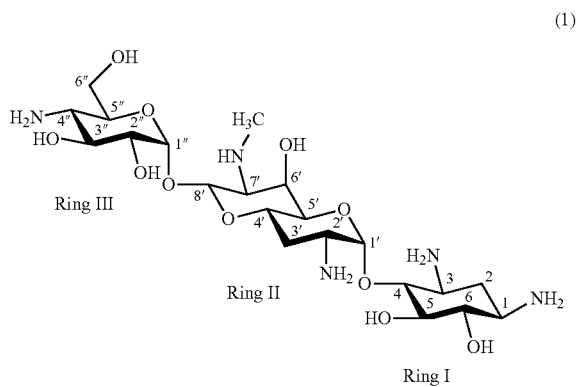

Apramycin consists of four rings, the numbering of which is indicated in formula (1) above, where the complete central bicyclic moiety is called ring II.

Position C5 of apramycin in the context of the present specification relates to the carbon atom designated 5 in ring I. Position O5 relates to the oxygen atom attached to C5.

Bacteria evade the action of existing aminoglycoside antibiotics by expression of aminoglycoside modifying enzymes (AMEs) which inactivate the drug. While AMEs vary between different bacteria, only a limited number of positions on the AGA framework are modified across the complete spectrum of bacteria.

Due to its structural uniqueness, apramycin has remained inherently potent against otherwise highly drug resistant pathogenic bacteria. Among the numerous classes of AMEs only the isoform AAC(3)-IV of the AAC(3) class of aminoacetyltransferases acting on N3 in the 2-deoxystreptamine ring of the AGAs gives rise to apramycin resistance.

Whole genome sequencing conducted by the inventors has identified the presence of AAC(3)-IV in human clinical isolates from the University of Zurich Institute of Medical Microbiology (IMM). It is to be expected that, if apramycin is approved for use in human medicine, resistance due to the presence of the AAC(3)-IV determinant will eventually emerge.

The inventors have found that certain modifications of apramycin at position C5 result in the retention of activity in the presence of the AAC(3) class of AME, including AAC(3)-IV.

In the context of the present specification, "apmA" refers to an apramycin-resistant aminocyclitol acetyltransferase gene identified from bovine multi drug resistant Staphylococcus aureus (MRSA) as described in Fessler et al. 2011. Antimicrob. Agents Chemother. 55(1):373-5.

In their effort to modify and improve apramycin, the inventors have surprisingly found that modification by introduction of a β-D-ri bofuranosyl group carrying a basic substituent at the ultimate 3'''-position results in a set of highly active compounds at the target level and in antibacterial assays including clinical isolates carrying the AAC(3)-IV AME. Many of the compounds also provide increased target specificity for bacterial versus human rRNA.

The inventors have additionally found that simple manipulation of the apramycin 5-OH by either deoxygenation, inversion, substitution by a halogen atom or by alkylation provides significant protection against the influence of the AAC(3)-IV AME. These improvements are made without loss of activity against wild type bacterial strains and exhibit improved activity when compared to the parent.

In a further related finding, the inventors have discovered that alkylation of the apramycin 6-OH provides increased target specificity for bacterial versus human rRNA.

The inventors provide apramycin derivatives with increased potency that circumvent inactivation by AAC(3)-VI. Further beneficial effects are increased antibacterial potency, protection against apmA, increased target specificity for bacterial versus human, and retained activity against G1405 methylated ribosomes.

As the derivatives are straightforward to prepare, this invention has enormous potential for the treatment of CREs and other multi-drug-resistant bacterial infections.

Terms and Definitions

A $C_1$-$C_4$ alkyl in the context of the present invention signifies a saturated linear or branched hydrocarbon having 1, 2, 3 or 4 carbon atoms, wherein in certain embodiments one carbon-carbon bond may be unsaturated and/or one $CH_2$ moiety may be exchanged for oxygen (ether bridge) or nitrogen (NH, or NR with R being methyl, ethyl, or propyl; amino bridge). Non-limiting examples for a $C_1$-$C_4$ alkyl are methyl, ethyl, propyl, prop-2-enyl, n-butyl, 2-methylpropyl, tert-butyl, but-3-enyl, prop-2-inyl and but-3-inyl. In certain embodiments, a $C_1$-$C_4$ alkyl is a methyl, ethyl, propyl or butyl moiety.

The term $C_1$-$C_6$ alkyl similarly refers to $C_1$-$C_4$ alkyls and their higher homologues, including additionally 3-methylbut-2-enyl, 2-methylbut-3-enyl, 3-methylbut-3-enyl, n-pentyl, 2-methylbutyl, 3-methylbutyl, 1,1-dimethylpropyl, 1,2-dimethylpropyl, 1,2-dimethylpropyl, pent-4-inyl, 3-methyl-2-pentyl, and 4-methyl-2-pentyl. In certain embodiments, a $C_5$ alkyl is a pentyl moiety and a $C_6$ alkyl is a hexyl or cyclohexyl moiety.

Where used in the context of chemical formulae, the following abbreviations may be used: Me is methyl $CH_3$ or —$CH_2$—, Et is ethyl —$CH_2CH_3$ or —$CH_2CH_2$—, Prop is propyl —$(CH_2)_2CH_3$ or —$(CH_2)_3$— (n-propyl, n-pr) or —$CH(CH_3)_2$ (iso-propyl, i-pr), but is butyl —$C_4H_9$, or —$C_4H_8$—, —$(CH_2)_3CH_3$, —$CHCH_3CH_2CH_3$, —$CH_2CH(CH_3)_2$ or —$CH(CH_3)_3$.

The term amino-substituted alkyl or hydroxy-substituted alkyl refers to an alkyl according to the above definition that is modified by one or several amine or hydroxyl groups $NH_2$, NHR, $NR_2$ or OH, wherein the R substituent as used in the current paragraph, different from other uses assigned to R in the body of the specification, is methyl, ethyl or propyl unless otherwise specified. An alkyl having more than one carbon may comprise more than one amine or hydroxyl. Unless otherwise specified, the term "substituted alkyl" refers to alkyl in which each C is only substituted by one amine or hydroxyl group, in addition to bonds to the alkyl chain, terminal methyl, or hydrogen.

Non-limiting examples of amino-substituted alkyl include —$CH_2NH_2$, —$CH_2NHMe$, —$CH_2NHEt$, —$CH_2CH_2NH_2$, —$CH_2CH_2NHMe$, —$CH_2CH_2NHEt$, —$(CH_2)_3NH_2$, —$(CH_2)_3NHMe$, —$(CH_2)_3NHEt$, —$CH_2CH(NH_2)CH_3$, —$CH_2CH(NHMe)CH_3$, —$CH_2CH(NHEt)CH_3$, —$(CH_2)_3CH_2NH_2$, —$(CH_2)_3CH_2NHMe$, —$(CH_2)_3CH_2NHEt$, —$CH(CH_2NH_2)CH_2CH_3$, —$CH(CH_2NHMe)CH_2CH_3$, —$CH(CH_2NHEt)CH_2CH_3$, —$CH_2CH(CH_2NH_2)CH_3$, —$CH_2CH(CH_2NHMe)CH_3$, —$CH_2CH(CH_2NHEt)CH_3$, —$CH(NH_2)(CH_2)_2NH_2$, —$CH(NHMe)(CH_2)_2NHMe$, —$CH(NHEt)(CH_2)_2NHEt$, —$CH_2CH(NH_2)CH_2NH_2$, —$CH_2CH(NHMe)CH_2NHMe$, —$CH_2CH(NHEt)CH_2NHEt$, —$CH_2CH(NH_2)(CH_2)_2NH_2$, —$CH_2CH(NHMe)(CH_2)_2NHMe$, —$CH_2CH(NHEt)(CH_2)_2NHEt$, —$CH_2CH(CH_2NH_2)_2$, —$CH_2CH(CH_2NHMe)_2$ and —$CH_2CH(CH_2NHEt)_2$.

Non-limiting examples of hydroxy-substituted alkyl include —$CH_2OH$, —$(CH_2)_2OH$, —$(CH_2)_3OH$, —$CH_2CH(OH)CH_3$, —$(CH_2)_4OH$, —$CH(CH_2OH)CH_2CH_3$, —$CH_2CH(CH_2OH)CH_3$, —$CH(OH)(CH_2)_2OH$, —$CH_2CH(OH)CH_2OH$, —$CH_2CH(OH)(CH_2)_2OH$ and —$CH_2CH(CH_2OH)_2$.

The term fluoro-substituted alkyl refers to an alkyl according to the above definition that is modified by one or several fluorine moieties F. Non-limiting examples of fluoro-substituted alkyl include —$CH_2F$, —$CHF_2$, —$CF_3$, —$(CH_2)_2F$, —$(CHF)_2H$, —$(CHF)_2F$, —$C_2F_5$, —$(CH_2)_3F$, —$(CHF)_3H$, —$(CHF)_3F$, —$C_3F_7$, —$(CH_2)_4F$, —$(CHF)_4H$, —$(CHF)_4F$ and —$C_4F_9$.

Non-limiting examples of hydroxyl-and fluoro-substituted alkyl include —$CHFCH_2OH$, —$CF_2CH_2OH$, —$(CHF)_2CH_2OH$, —$(CF_2)_2CH_2OH$, —$(CHF)_3CH_2OH$, —$(CF_2)_3CH_2OH$, —$(CH_2)_3OH$, —$CF_2CH(OH)CH_3$, —$CF_2CH(OH)CF_3$, —$CF(CH_2OH)CHFCH_3$, and —$CF(CH_2OH)CHFCF_3$.

The term "$C_1$ to $C_4$ alkenyl or alkynyl" refers to unsaturated linear carbon chains, particularly unsubstituted carbon chains, i.e. the moiety thus referred to is constituted of carbon and hydrogen atoms only. It encompasses, but is not limited to, ethenyl (—$CHCH_2$), ethynyl (—CCH) or allyl (CH—$CHCH_2$) and but-2-enyl (—$CH_2CHCHCH_3$).

Unless explicitly stated otherwise, the following letters, when contained as capital lettering in a formula, refer to atoms: H hydrogen, C carbon, F fluorine, N nitrogen, O oxygen, S sulphur, P phosphorus. CHO designates a formyl moiety. $NHCONH_2$ designates an ureido moiety.

A first aspect of the invention relates to a compound characterized by a general formula (100)

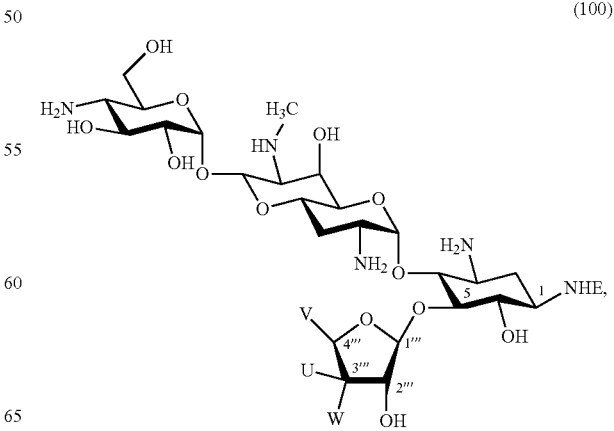

(100)

wherein

E is selected from H, —COR$^E$, —CONHR$^E$, —CON(OH)R$^E$ and unsubstituted $C_1$ to $C_4$ alkyl or amino- and/or hydroxyl-substituted $C_2$ to $C_4$ alkyl, wherein R$^E$ is H or an unsubstituted or amino- and/or hydroxyl-substituted $C_1$ to $C_6$ alkyl (particularly R$^E$ is H or an amino- and/or hydroxyl-substituted $C_1$ to $C_5$ alkyl), particularly wherein E is selected from H and (S)-4-amino-2-hydroxybutyryl, (S)-3-amino-2-hydroxypropionyl, —CON(OH)(CH$_2$)$_2$NH$_2$), (2R,3S)-2-hydroxy-4,5-diamino-pentanoyl, and (2S,3R)-2,5-dihydroxy-4-aminopentanoyl;

V is selected from H and —CH$_2$D, wherein

D is selected from OH, NH$_2$, —NHCHO, NHR$^D$ and —NHCONHR$^D$, wherein R$^D$ is selected from H, OH, unsubstituted or amino- and/or hydroxy-substituted $C_1$ to $C_6$ alkyl, particularly wherein D is selected from OH, —NHCHO and —NHCONH$_2$;

U and W are selected from the following alternatives:

one of U and W is —R$^W$ and the other one is selected from H, F, OH, or one of U and W is —OR''' and the other one is H, or one of U and W is F and the other one is H, both are H or both are F, or one of U and W is OH and the other one is H, wherein R$^W$ is selected from an amino- and/or hydroxy-substituted $C_1$ to $C_6$ alkyl, —CH$_2$(CH$_2$)$_n$NH(CH$_2$)$_3$NH$_2$ and —CH$_2$(CH$_2$)$_n$R$^N$, wherein n is selected from 1, 2 or 3, R$^N$ is selected from NXY and a moiety characterized by formula (400)

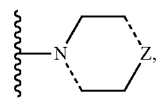

(400)

wherein

X and Y are independently selected from H, and unsubstituted or amino- and/or hydroxyl-substituted $C_1$ to $C_3$ alkyl, particularly from H and CH$_3$, CH$_2$CH$_3$ and —CH$_2$CH$_2$OH or —CH$_2$CH$_2$NH$_2$ and Z is selected from O, NX (where X has the same meaning as indicated above in this paragraph) and CH$_2$, or one of U and W (particularly W) is described by a moiety characterized by formula (300), (301), (304) or (305) and the other one of U and W is H

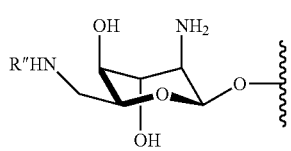

(300)

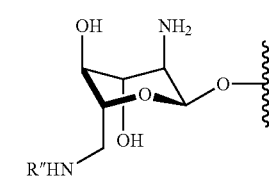

(301)

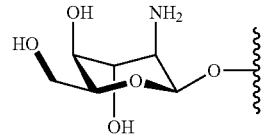

(304)

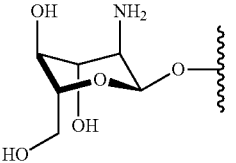

(305)

wherein R'' is selected from H and an amino- and/or hydroxy-substituted $C_1$ to $C_6$ alkyl, particularly wherein one of U and W (particularly W) is

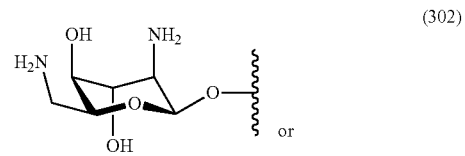

(302) or (303)

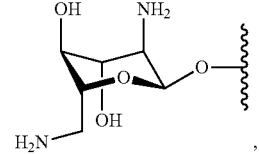

with the proviso that the molecule is not described by the following combination of parameters:

D is OH, U is H and W is OH.

Furthermore, with effect to certain countries not including Australia, Brazil, Mexico, Singapore, the USA, and Ukraine, the following compounds are disclaimed:

V and U are H and W is OH,

D is OH, U is H and W is —O(CH$_2$)$_2$NH$_2$,

D is OH, U is H and W is a moiety characterized by formula (302).

In certain embodiments, V is —CH$_2$OH.

In certain embodiments, V is H.

In certain embodiments, V is selected from —CH$_2$NHCHO and —CH$_2$NHCONH$_2$.

In certain embodiments, V is —CH$_2$NHR$^D$ and R$^D$ has the same meaning as indicated above.

In certain embodiments, E is H or —COR$^E$, wherein R$^E$ is an amino- and/or hydroxy-modified $C_1$ to $C_5$ alkyl.

In certain embodiments, one of U and W is —R$^W$ and the other one is selected from H, F and OH, wherein R$^W$ has the same meaning as indicated above.

In certain embodiments, one of U and W is —OR$^W$ and the other one is H, wherein R$^W$ has the same meaning as indicated above.

In certain embodiments, one of U and W is —OR$^W$, with R$^W$ being selected from (CH$_2$)$_2$OH, (CH$_2$)$_2$NH$_2$, (CH$_2$)$_2$NMe$_2$, (CH$_2$)$_2$NEt$_2$, (CH$_2$)$_2$NHMe, (CH$_2$)$_2$NHEt, (CH$_2$)$_3$OH, (CH$_2$)$_3$NH$_2$, (CH$_2$)$_3$NMe$_2$, (CH$_2$)$_3$NEt$_2$, (CH$_2$)$_3$NHMe, (CH$_2$)$_3$NHEt, CH$_2$CHOHCH$_2$OH, CH$_2$CHOHCH$_2$NH$_2$, CH$_2$CHOHCH$_2$NMe$_2$, CH$_2$CHOHCH$_2$NEt$_2$, CH$_2$CHOHCH$_2$NHMe and CH$_2$CHOHCH$_2$NHEt.

In certain embodiments, one of U and W is —$R^W$, with $R^W$ being selected from $(CH_2)_2OH$, $(CH_2)_2NH_2$, $(CH_2)_2NMe_2$, $(CH_2)_2NEt_2$, $(CH_2)_2NHMe$, $(CH_2)_2NHEt$, $(CH_2)_3OH$, $(CH_2)_3NH_2$, $(CH_2)_3NMe_2$, $(CH_2)_3NEt_2$, $(CH_2)_3NHMe$, $(CH_2)_3NHEt$, $CH_2CHOHCH_2OH$, $CH_2CHOHCH_2NH_2$, $CH_2CHOHCH_2NMe_2$, $CH_2CHOHCH_2NEt_2$, $CH_2CHOHCH_2NHMe$ and $CH_2CHOHCH_2NHEt$.

In certain embodiments, one of U and W is F and the other one is H, both are H or both are F.

In certain embodiments, one of U and W is OH and the other one is H.

In certain embodiments, W is —$R^W$ and U is selected from H, F, OH; or W is —$OR^W$ and U is H, wherein $R^W$ has the same meaning as indicated above.

In certain embodiments, the compound is characterized by a general formula (110)

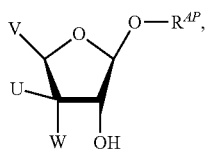
(110)

wherein $R^{AP}$ designates a moiety described by formula (2)

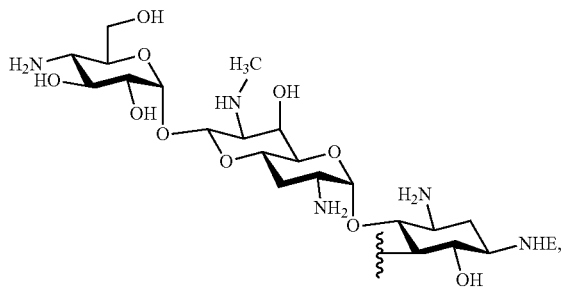
(2)

E has the meaning as defined above in the broadest sense, or in more narrowly defined embodiments of E;

V is selected from H and —$CH_2D$, wherein
D is selected from OH, $NH_2$, —NHCHO and —$NHCONHR^D$, wherein $R^D$ is selected from H, OH, unsubstituted or amino- and/or hydroxy-substituted $C_1$ to $C_3$ alkyl, particularly wherein D is selected from OH, —NHCHO and —$NHCONH_2$;

W is F and U is selected from OH and F and $\xi$ denotes the position where the apramycin backbone is attached to the compound described by general formula (110).

In certain embodiments, the compound is characterized by a general formula (112), (113) or (114)

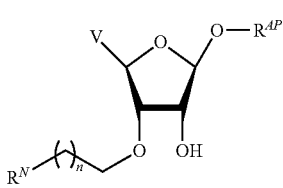
(112)

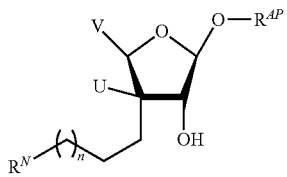
(113)

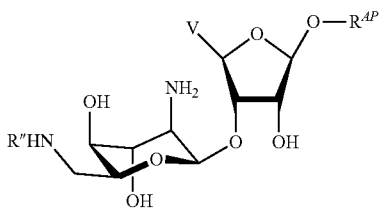
(114)

wherein U is selected from OH and F and n, $R^{AP}$, R″, $R^N$ and V have the same meaning as indicated above.

In certain embodiments, E is H, V is —$CH_2NHCHO$, U is H and W is OH [5—O—β—(5‴-Formamido-5‴-deoxy-D-ribofuranosyl) apramycin DCWSU177].

In certain embodiments, the compound is characterized by the general formula
a. (112), wherein E is H, $R^N$ is OH, V is $CH_2OH$ and n is 1 [5—O—β-[3‴-O-(2-hydroxyethyl)-D-ribofuranosyl] apramycin; DCWSU178];
b. (112), wherein E is H, $R^N$ is $NH_2$, V is $CH_2NH_2$ and n is 1 [5—O-β-[5-amino-3-O-(2-aminoethyl)-5-deoxy-D-ribofuranosyl] apramycin; DCWSU185];
c. (112), wherein E is H, V is $CH_2NHCOH$, $R^N$ is $NH_2$ and n is 1 [5—O-β-[3-O-(2-aminoethyl)-5-deoxy-5-formamido-D-ribofuranosyl] apramycin; DCWSU186].

In certain embodiments, the compound is characterized by the general formula (100), wherein
a. E, U and V are H and W is —$OR^W$, and $R^W$ is selected from $(CH_2)_2OH$, $(CH_2)_2NH_2$, $(CH_2)_2NMe_2$, $(CH_2)_2NEt_2$, $(CH_2)_2NHMe$, $(CH_2)_2NHEt$, $(CH_2)_3OH$, $(CH_2)_3NH_2$, $(CH_2)_3NMe_2$, $(CH_2)_3NEt_2$, $(CH_2)_3NHMe$, $(CH_2)_3NHEt$, $CH_2CHOHCH_2OH$, $CH_2CHOHCH_2NH_2$, $CH_2CHOHCH_2NMe_2$, $CH_2CHOHCH_2NEt_2$, $CH_2CHOHCH_2NHMe$ and $CH_2CHOHCH_2NHEt$;
b. E and U are H, V is $CH_2OH$ and W is a moiety described by formula (300), with R″ selected from H, $(CH_2)_2OH$, $(CH_2)_2NH_2$, $(CH_2)_2NMe_2$, $(CH_2)_2NEt_2$, $(CH_2)_2NHMe$ and $(CH_2)_3NHEt$;
c. E and W are H, U is OH and V is selected from $CH_2OH$ and $CH_2NH_2$;
d. E is H, V is $CH_2D$ with D being selected from OH, $NH_2$ and —NHCHO, and one of
U and W is F, and the other one of U and W is H.

These compounds are claimed with effect in Australia, Brazil, Mexico, Singapore, the USA, and Ukraine: compounds according to formula (100), wherein U is H and
a. V is H and W is OH,
b. D is OH, U is H and W is $O(CH_2)_2NH_2$,
c. D is OH, U is H and W is a moiety characterized by formula (302).

The intermediates in a synthesis for an apramycin derivative antibacterial drug:
a. 3-O-(2-azidoethyl)-5-O-benzyl-1,2-O-isopropylidene-α-D-ribofuranose (E FIG. 1);
b. 3-O-(2-azidoethyl)-5-O-benzyl-1,2-di-O-(4-nitrobenzoyl)-α-D-ribofuranose (F FIG. 1)

c. 5,6,2″,3″,6″-penta-O-acetyl-1,3,2′,4″-tetraazido-5-epi-6′,7′-oxazolidino-apramycin (j; FIG. 12);
d. 6,2″,3″,6″-tetra-O-acetyl-1,3,2′,4″-tetraazido-5-epi-6′,7′-oxazolidino-apramycin (k; FIG. 12)
e. 5,2″,3″,6″-tetra-O-acetyl-6-O-allyl-1,3,2′, 4″-tetraazido-6′, 7′-oxazolidino-apramycin (AK; FIG. 16)
f. 1,2,3-tri-O-acetyl-5-deoxy-5-phthalimido-α-D-ribofuranose (I; FIG. 5);
g. 2,3-di-O-acetyl-5-deoxy-5-phthalimido-D-ribofuranosyl trichloroacetimidate (J; FIG. 5);
h. 3-O-(2-azidoethyl)-5-di(benzyloxycarbonyl)amino-5-deoxy-1,2-O-isopropylidene-α-D-ribofuranose (P; FIG. 7)
i. 3-O-(2-azidoethyl)-5-di(benzyloxycarbonyl)amino-5-deoxy-1,2-di-O-(p-nitrobenzoyl)-60 /β-D-ribofuranose (Q; FIG. 7);
and with effect for Australia, Brazil, Mexico, Singapore, the USA, and Ukraine:
j. 6,2″, 3″, 6″-tetra-O-acetyl-1,3,2′, 4″-tetraazido-6′, 7′-oxazolidino-apramycin (A; FIG. 17)

According to another aspect, the invention relates to a compound characterized by a general formula (200)

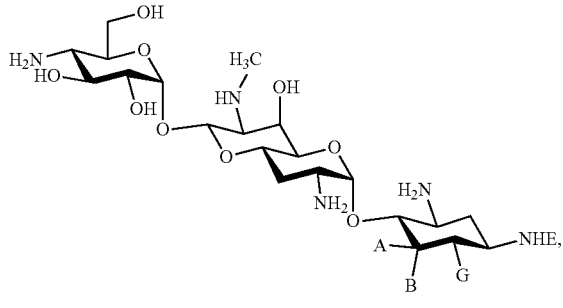

(200)

wherein A or B or G is $OR^1$, and
if one of A and B is $OR^1$, the other is H and G is OH, or
if G is $OR^1$, one of A and B is OH and the other one is H,
wherein $R^1$ is an unsubstituted $C_1$ to $C_6$ alkyl or an amino- and/or hydroxy-substituted $C_2$ to $C_6$ alkyl, particularly $R^1$ is an amino- and/or hydroxy-substituted $C_2$ to $C_6$ alkyl, more particularly $R^1$ is selected from 3-aminopropyl $(CH_2)_3NH_2$, 3-hydroxypropyl $(CH_2)_3OH$, 2-hydroxy-3-aminopropyl $CH_2CH(OH)CH_2NH_2$, and 2,3-dihydroxypropyl $CH_2CH(OH)CH_2OH$;
or
wherein one of A and B is F and the other one is H, or A and B together form a carbonyl oxygen (see compound AF in FIG. 13), and G is OH;
E is selected from H, $—COR^E$, $—CONHRE$, $—CON(OH)R^E$ and unsubstituted $C_1$ to $C_4$ alkyl or amino- and/or hydroxyl-substituted $C_2$ to $C_4$ alkyl, wherein
$R^E$ is H or an unsubstituted or amino- and/or hydroxyl-substituted $C_1$ to $C_6$ alkyl (particularly $R^E$ is H or an amino- and/or hydroxyl-substituted $C_1$ to $C_5$ alkyl), particularly E is selected from H and (S)-4-amino-2-hydroxybutyryl, (S)-3-amino-2-hydroxypropionyl, $—CON(OH)(CH_2)_2NH_2$), (2R,3S)-2-hydroxy-4,5-di-amino-pentanoyl, and (2S,3R)-2,5-dihydroxy-4-aminopentanoyl;
with the proviso that that the molecule is not described by any one of the following combination of parameters:

A and G are OH and B and E are H,
A and G are OH, B is H and E is unsubstituted $C_1$ to $C_4$ alkyl or amino- and/or hydroxyl-substituted $C_2$ to $C_4$ alkyl,
A and G are OH, B is H and E is $—COC(OH)(CH_2)_2NH_2$
A, B and E are H and G is OH,
A and E are H and B and G are OH
A and E are H, B is F and G is OH.

Furthermore, with effect to certain countries not including Australia, Brazil, Mexico, Singapore, the USA, and Ukraine, the following compounds are disclaimed:
B is H, G is OH and A is selected from $—OCH_2CH_2EtOH$, $—OCH_2CHOHCH_2OH$ (glyceryl), and $—OEt$.

In certain embodiments of this aspect of the invention, one of A and B is F.

In certain embodiments of this aspect of the invention, one of A and B is $—OR^1$, wherein $R^1$ has the meaning as indicated above.

In certain embodiments of this aspect of the invention, G is $—OR^1$.

In certain embodiments of this aspect of the invention, E is H or $—COR^E$, wherein $R^E$ is an amino- and/or hydroxy-modified $C_1$ to $C_5$ alkyl.

In certain embodiments of this aspect of the invention, E is H and:
a. A is F, B is H and G is OH;
b. B is H, G is OH and A is $—OR^1$, with $R^1$ being selected from $(CH_2)_2OH$, $CH_2CH_2CH_3$, $(CH_2)_2NH_2$, $(CH_2)_2NMe_2$, $(CH_2)_2NEt_2$, $(CH_2)_2NHMe$, $(CH_2)_2NHEt$, $(CH_2)_3OH$, $(CH_2)_3NH_2$, $(CH_2)_3NMe_2$, $(CH_2)_3NEt_2$, $(CH_2)_3NHMe$, $(CH_2)_3NHEt$, $CH_2CHOHCH_2OH$, $CH_2CHOHCH_2NH_2$, $CH_2CHOHCH_2NMe_2$, $CH_2CHOHCH_2NEt_2$, $CH_2CHOHCH_2NHMe$ and $CH_2CHOHCH_2NHEt$;

In certain embodiments of this aspect of the invention, E is $—COCHOH(CH_2)_2NH_2$, E is particularly (S)-2-hydroxy-4-aminobutyl, and:
a. G is OH and A and B are selected from the alternatives: A is H and B is F or A is H and B is OH or A is F and B is H or A and B are both H or A and B together form a carbonyl O;
b. B is H, G is OH and A is $—OR^1$, with $R^1$ being selected from $(CH_2)_2OH$, $CH_2CH_2CH_3$, $(CH_2)_2NH_2$, $(CH_2)_2NMe_2$, $(CH_2)_2NEt_2$, $(CH_2)_2NHMe$, $(CH_2)_2NHEt$, $(CH_2)_3OH$, $(CH_2)_3NH_2$, $(CH_2)_3NMe_2$, $(CH_2)_3NEt_2$, $(CH_2)_3NHMe$, $(CH_2)_3NHEt$, $CH_2CHOHCH_2OH$, $CH_2CHOHCH_2NH_2$, $CH_2CHOHCH_2NMe_2$, $CH_2CHOHCH_2NEt_2$, $CH_2CHOHCH_2NHMe$ and $CH_2CHOHCH_2NHEt$
c. A is OH, B is H, and G is $—OR^1$, with $R^1$ being selected from $(CH_2)_2OH$, $(CH_2)_2NH_2$, $(CH_2)_2NMe_2$, $(CH_2)_2NEt_2$, $(CH_2)_2NHMe$, $(CH_2)_2NHEt$, $(CH_2)_3OH$, $(CH_2)_3NH_2$, $(CH_2)_3NMe_2$, $(CH_2)_3NEt_2$, $(CH_2)_3NHMe$, $(CH_2)_3NHEt$, $CH_2CHOHCH_2OH$, $CH_2CHOHCH_2NH_2$, $CH_2CHOHCH_2NMe_2$, $CH_2CHOHCH_2NEt_2$, $CH_2CHOHCH_2NHMe$ and $CH_2CHOHCH_2NHEt$.

An alternative aspect of the invention relates to a compound characterized by a general formula (201)

(201)

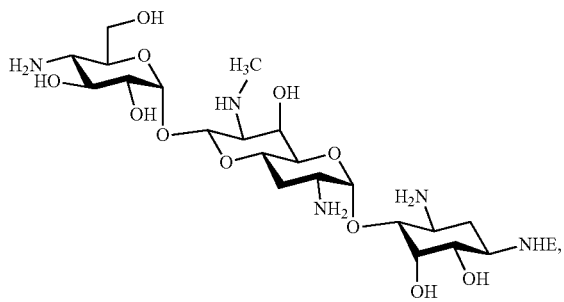

wherein E is selected from CO—$R^E$, CONH$R^E$, CON(OH)$R^E$ and unsubstituted $C_1$ to $C_4$ alkyl or amino- and/or hydroxyl-substituted $C_2$ to $C_4$ alkyl, wherein $R^E$ is H or an unsubstituted or amino- and/or hydroxyl-substituted $C_1$ to $C_6$ alkyl (particularly $R^E$ is H or an amino- and/or hydroxyl-substituted $C_1$ to $C_5$ alkyl), particularly E is selected from H and (S)-4-amino-2-hydroxybutyryl, (S)-3-amino-2-hydroxypropionyl, —CON(OH)(CH$_2$)$_2$NH$_2$), (2R,3S)-2-hydroxy-4,5-diamino-pentanoyl, and (2S,3R)-2,5-dihydroxy-4-aminopentanoyl.

In certain embodiments, the compound is characterized by one of the following structures:

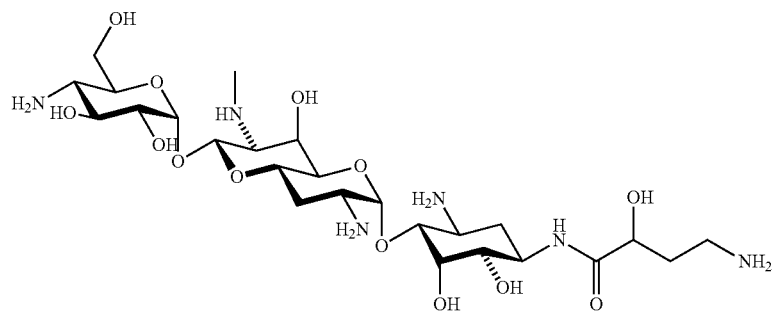

DC191

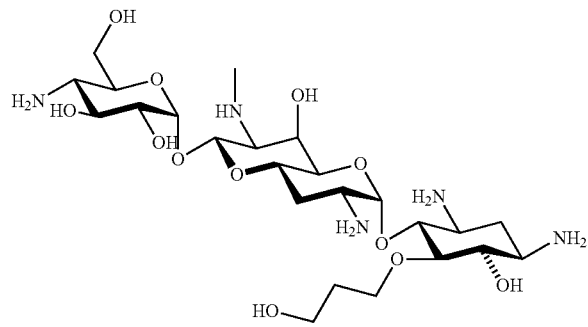

DC207

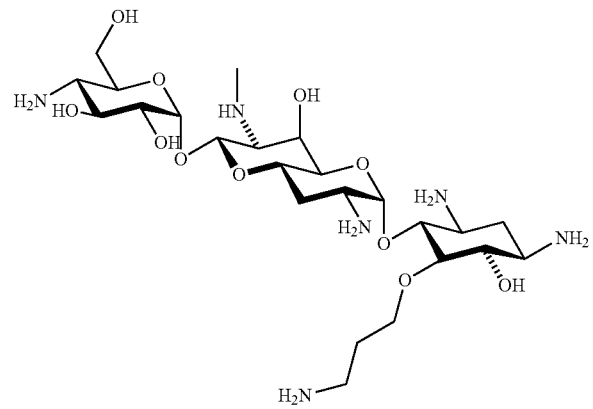

DC213

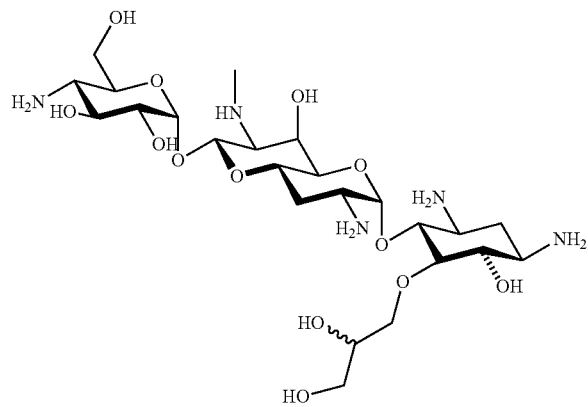

DC208

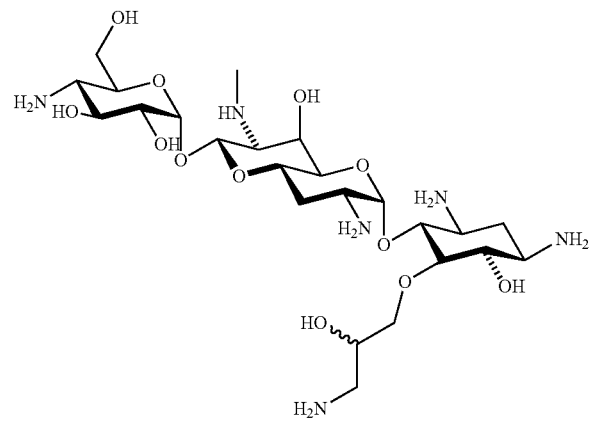

DC209

DC201
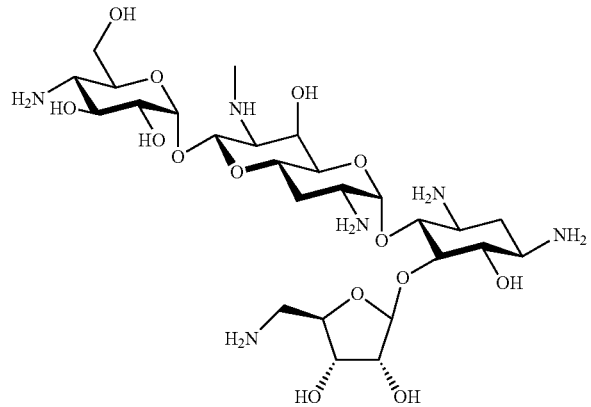

DC214
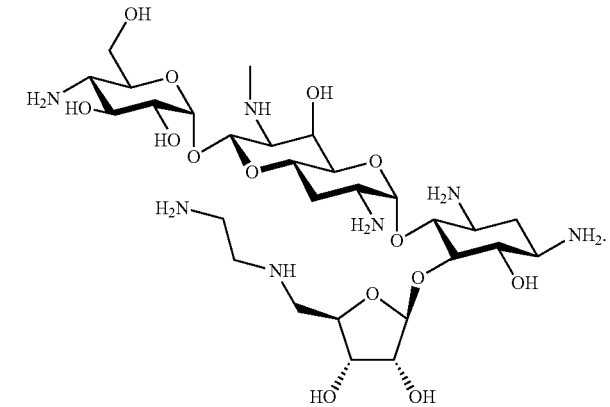

Another aspect of the invention relates to the use of a compound according to any of the previously described aspects and embodiments, or combinations of their particular features, in the therapy of bacterial infection by systemic administration. The skilled artisan is aware that on the basis of the data provided and the general description, certain compounds can be identified that show advantageous selectivity for bacterial, rather than eukaryotic mitochondrial, ribosomes. This aspect of the invention alternatively relates to a method of treatment of a patient suffering from bacterial infection and comprises systemic administration of an effective amount of a compound as defined in the present application.

Infections in which the compounds of the invention are of particular therapeutic interest include those caused by pathogens comprised in the family Enterobacteriaceae, particularly in the genera Enterobacter, Escherichia and Klebsiella, or caused by pathogens selected from a genus comprised in the group of Acinetobacter, Mycobacteria, Pseudomonas and Staphylococcus.

Another aspect of the invention relates to a compound for use in the therapy of bacterial infection, particularly by systemic administration, wherein the infection is caused by a pathogen carrying the AAC(3)-IV resistance determinant, and wherein the compound is characterized by a general formula (100) or (200).

The compounds disclaimed above have not been shown to provide advantages in treatment of pathogens carrying the resistance determinant AAC(3)-IV. Therefore, these compounds are not excluded from the compounds useful in the therapy of bacterial infection caused by a pathogen carrying the AAC(3)-IV resistance determinant, particularly by systemic administration. These compounds are selected from
  a. a compound defined by formula (100), wherein
   i. D is OH, U is H and W is OH;
   ii. V and U are H and W is OH;
   iii. D is OH, U is H and W is O(CH$_2$)$_2$NH$_2$;
   iv. D is OH, U is H and W is a moiety characterized by formula (302); and
  b. a compound defined by formula (200), wherein
   i. A and G are OH, B is H and E is unsubstituted C$_1$ to C$_4$ alkyl, or amino- and/or hydroxyl-substituted C$_2$ to C$_4$ alkyl;
   ii. A and G are OH, B is H and E is COC(OH)(CH$_2$)$_2$NH$_2$;
   iii. A, B and E are H and G is OH;
   iv. A and E are H and B and G are OH;
   v. A and E are H, B is F and G is OH; and
   vi. B is H, G is OH and A is selected from —OCH$_2$CH$_2$EtOH, —OCH$_2$CHOHCH$_2$OH (glyceryl), and —OEt.

The same compounds as included in the preceding paragraph are also useful for infections caused by a pathogen, selected from a genus comprised in the group of Enterobacter, Klebsiella, Acinetobacter, and Mycobacteria.

A particular aspect of the invention relates to the use of a compound defined by formula (100),
 wherein V is CH$_2$NH$_2$, W is —OR$^W$, and
 R$^W$ is selected from (CH$_2$)$_2$OH, (CH$_2$)$_2$NH$_2$, (CH$_2$)$_2$NMe$_2$, (CH$_2$)$_2$NEt$_2$, (CH$_2$)$_2$NHMe, (CH$_2$)$_2$NHEt, (CH$_2$)$_3$OH, (CH$_2$)$_3$NH$_2$, (CH$_2$)$_3$NMe$_2$, (CH$_2$)$_3$NEt$_2$, (CH$_2$)$_3$NHMe, (CH$_2$)$_3$NHEt, CH$_2$CHOHCH$_2$OH, CH$_2$CHOHCH$_2$NH$_2$, CH$_2$CHOHCH$_2$NMe$_2$, CH$_2$CHOHCH$_2$NEt$_2$, CH$_2$CHOHCH$_2$NHMe and CH$_2$CHOHCH$_2$NHEt,
 particularly wherein R$^W$ is selected from (CH$_2$)$_2$NH$_2$, (CH$_2$)$_2$NMe$_2$, (CH$_2$)$_2$NEt$_2$, (CH$_2$)$_2$NHMe, (CH$_2$)$_2$NHEt, (CH$_2$)$_3$NH$_2$, (CH$_2$)$_3$NMe$_2$, (CH$_2$)$_3$NEt$_2$, (CH$_2$)$_3$NHMe, (CH$_2$)$_3$NHEt, CH$_2$CHOHCH$_2$NH$_2$, CH$_2$CHOHCH$_2$NMe$_2$, CH$_2$CHOHCH$_2$NEt$_2$, CH$_2$CHOHCH$_2$NHMe and CH$_2$CHOHCH$_2$NHEt, more particularly R$^W$ is selected from (CH$_2$)$_2$NH$_2$ and (CH$_2$)$_3$NH$_2$,
 U is H and E is defined as above in the broadest definition, particularly wherein E is selected from H and CO—R$^E$, wherein R$^E$ is a C$_1$ to C$_6$ unsubstituted or amino- and/or hydroxyl-substituted alkyl, more particularly E is selected from H and (S)-4-amino-2-hydroxybutyryl, (S)-3-amino-2-hydroxypropionyl, —CON(OH)(CH$_2$)$_2$NH$_2$), (2R,3S)-2-hydroxy-4,5-diamino-pentanoyl, and (2S,3R)-2,5-dihydroxy-4-aminopentanoyl,
 in the therapy of bacterial infection, wherein the infection is caused by a pathogen comprised in the family Enterobacteriaceae, particularly in the genera Enterobacter, Escherichia and Klebsiella, or selected from a genus comprised in the group of Acinetobacter, Mycobacteria, Pseudomonas and Staphylococcus.

The position O5 modifications of apramycin with a β-D-ribofuranosyl group carrying a basic substituent at the ultimate 3'''-position are suitable modifications to the parent enabling the reduction of toxicity and surmounting the effect of the AAC(3)-IV resistance determinant. These modifications are suitable for use either alone or in combination with other tolerated aminoglycoside modifications designed to surmount other resistance mechanisms and/or reduce toxicity.

Similarly, the invention relates to a dosage form for the prevention or treatment of bacterial infection, the dosage form comprising an apramycin derived antibacterial drug according to one of the above aspects of the invention. Dosage forms may be for enteral administration, such as nasal, buccal, rectal, transdermal or oral administration, or as an inhalation form or suppository. Alternatively, parenteral administration may be used, such as subcutaneous, intravenous, intrahepatic or intramuscular injection forms. Optionally, a pharmaceutically acceptable carrier and/or excipient may be present.

Topical administration is also within the scope of the advantageous uses of the invention. The skilled artisan is aware of a broad range of possible recipes for providing topical formulations, as exemplified by the content of Benson and Watkinson (Eds.), Topical and Transdermal Drug Delivery: Principles and Practice (1st Edition, Wiley 2011, ISBN-13: 978-0470450291); and Guy and Handcraft: Transdermal Drug Delivery Systems: Revised and Expanded ($2^{nd}$ Ed., CRC Press 2002, ISBN-13: 978-0824708610); Osborne and Amann (Eds.): Topical Drug Delivery Formulations (1st Ed. CRC Press 1989; ISBN-13: 978-0824781835).

Wherever alternatives for single separable features such as, for example, substituents A, B and D are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

EXAMPLES

Example 1

General Methods and Materials

Figure 1:
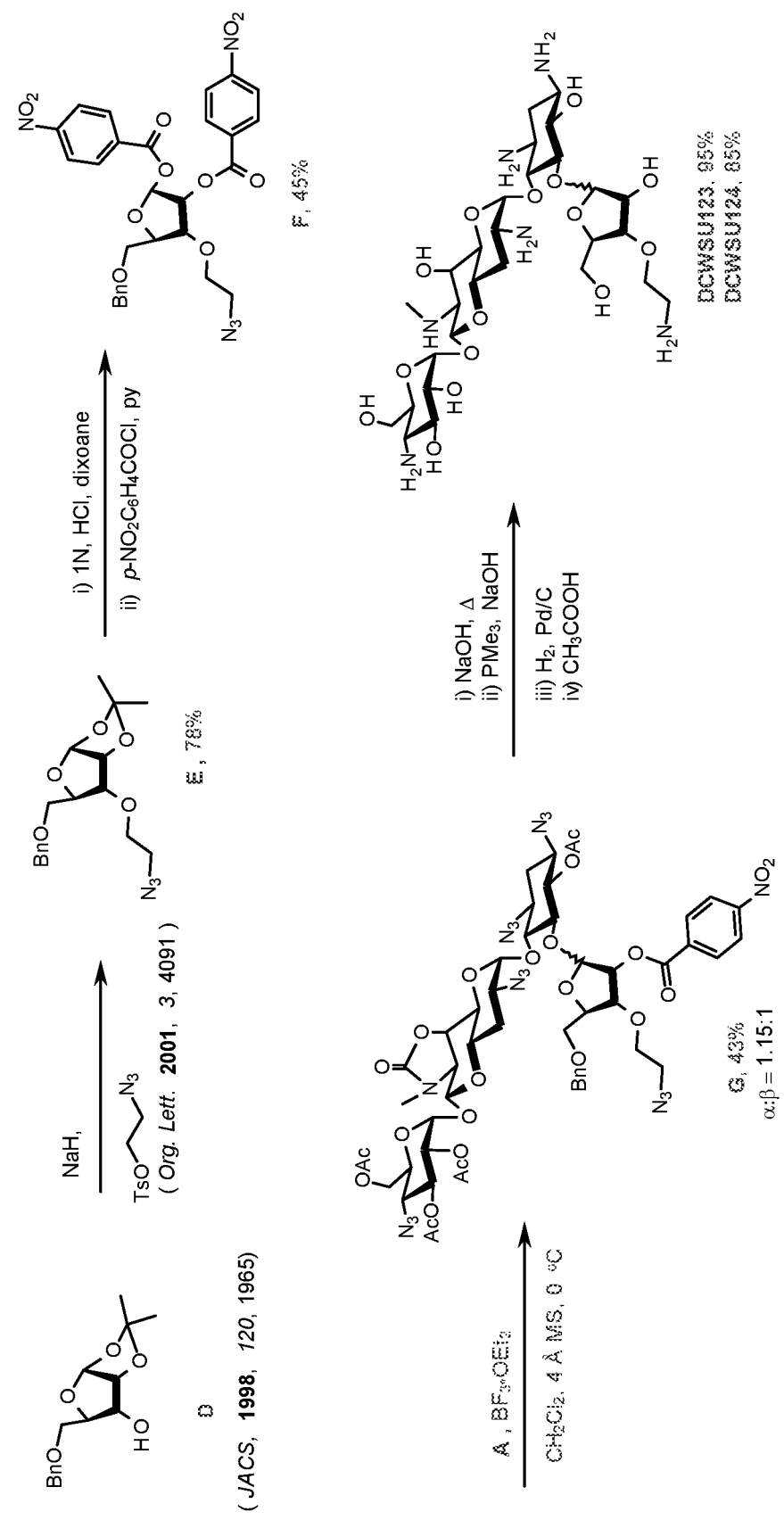
FIGS. 1 to 11 show the synthesis of exemplary compounds of the invention that are ribosylated at position 5.

All reagents and solvents were purchased from commercial suppliers and were used without further purification unless otherwise specified. Chromatographic purifications were carried out over silica gel. Analytical thin-layer chromatography was performed with pre-coated glass backed plates (w/UV 254) and visualized by UV irradiation (254 nm) or by staining with 25% $H_2SO_4$ in EtOH or ceric ammonium molybdate (ceric sulfate: (4.0 g); ammonium molybdate (10 g); $H_2SO_4$: 40 mL, $H_2O$: 360 mL) solution. Specific rotations were obtained using a digital polarimeter in the solvent specified at 589 nm and 23° C. on an Autopol III polarimeter (Rudolph Research Analytical, Hacketts-town, N.J.) with a path length of 10 cm. Infrared spectra were recorded on a FT/IR instrument. High resolution mass spectra were recorded with an electrospray source coupled to a time-of-flight mass analyzer (Waters). $^1H$, $^{13}C$ and 2D NMR spectra were recorded on 400 MHz, 500 MHz or 600 MHz instruments as specified. Assignments in $^1H$ and $^{13}C$ NMR were done by the assistance of H—H COSY, HSQC and/or HMBC experiments.

Chemistry: All syntheses were run under an atmosphere of nitrogen or argon. Solvents were dried and purified by standard techniques.

Minimal inhibitory concentrations (MIC) have been determined by broth microdilution assays (CLSI. *Methods for Dilution Antimicrobial Susceptibility Tests for Bacteria That Grow Aerobically*; Approved Standard—Tenth Edition. CLSI document M07-A10. Wayne, Pa.: Clinical and Laboratory Standards Institute; 2015.).

IC50 values for bacterial, human chimeric, and rabbit reticulocyte ribosomes have been determined by in-vitro translation assays as described previously (Proc. Nat. Ac. Sci USA 2012, 109(27):10984-10989).

Example 2

Apramycin Derivatives Active in the Presence of AAC(3) AMEs.

A) O5-ribosylated apramycin derivatives

Table 1 shows 5-ribosylated apramycin derivatives. Minimal inhibitory concentrations (MICs, pg/ml) against clinical isolates from Institute of Medical Microbiology, Univ. Zurich, and the IC50 values for bacterial, human mitochondrial and human cytosolic ribosomes are indicated.

Compounds 124 and 138, in which the β-D-ri bofuranosyl ring appended to the O5-position of apramycin is substituted with a basic residue at the 3'"-position show excellent antiribosomal and antibacterial activity even against the IMM clinical isolates carrying the gene for AAC(3)-IV. These compounds are distinct from the simple unsubstituted β-D-ribofuranosyl apramycin derivative (compound 131), which was described in 1981 by a Japanese group, and which shows no activity against the AAC(3)-IV carrying bacterial strains.

The introduction of a ribofuranosyl ring renders compound 124 and compound 138 susceptible to the APH(3', 5") resistance determinant, but modifications such as the inclusion of a 5'"-formamido group as in compound 186 circumvent this problem. The introduction of a formamido group results in compounds that display increased selectivity for the bacterial ribosome over the mitochondrial (wild type and A1555G mutant) ribosomes, predictive of reduced ototoxicity.

In addition to its outstanding antibacterial profile, compound 124 shows excellent selectivity at the target level with only low activity against eukaryotic ribosomes, indicating that it will share and even improve on the toxicity profile of apramycin itself.

Compound 185 shows increased antibacterial potency not only against Enterobacteriaceae, but also and in particular for Pseudomonas, Acinetobacter, and Mycobacteria (Tables 4+5).

B) 5-OH Manipulated Apramycin Derivatives

Table 2 shows 5-OH manipulated apramycin derivatives.
Examples include the manipulation of the 5-OH of apramycin by deoxygenation (compound 169), inversion (compound 161), substitution by a halogen atom (compound 170 and compound 168) or by alkylation.

Changes in the polarity or conformation of the substituent in position 5 (by oxygenation, inversion or substitution by a halogen atom) increase the antibacterial potency in comparison to the native apramycin. These compounds also circumvent the resistance mechanism apmA, a particular case in point being illustrated by compound 161.

Alkylation is expected to provide a similar effect as the ribosylation described above.

Minimal inhibitory concentrations (μg/ml) against clinical isolates from Institute of Medical Microbiology, Univ. Zurich, and the IC50 values for bacterial, human mitochondrial and human cytosolic ribosomes are indicated.

C) 6-OH Manipulated Apramycin Derivatives

Table 3 shows apramycin derivatives in which the 6-OH of apramycin is manipulated by alkylation.

Compound 167 shows an increased target specificity for bacterial versus human rRNA.

The Minimal inhibitory concentrations (MICs, μg/ml) against clinical isolates from Institute of Medical Microbiology, Univ Zurich, and the IC50 values for bacterial, human mitochondrial and human cytosolic ribosomes are indicated.

Table 4 and 5 show the antibacterial activity of the compounds of the invention against bacterial reference strains (table 4) and against representative clinical isolates (table 5).

Table 6 shows the activity of the compounds of the invention against G1405-methylated 16S-rRNA.

Example 3

DCWSU123 and DCWSU124

See the synthetic scheme of FIG. 1.

3-O-(2-Azidoethyl)-5-O-benzyl-1,2-O-isopropylidenea-α-D-ribofuranose (E). 5-O-Benzyl-1,2-O-isopropylidene-α-D-ribofuranose (1.00 g, 3.57 mmol) was dissolved in dry THF (3 mL) and NaH (214 mg, 5.36 mmol) was added under argon. After stirring for 15 min, a solution of 2-azidoethyl tosylate (1.72 g, 7.14 mmol) in dry THF (3 mL) was added dropwise followed by stirring for 12 h. More NaH (150 mg, 3.75 mmol) and 2-azidoethyl tosylate (860 mg, 3.57 mmol) were added and stirring continued for 24 h. After completion, the reaction was quenched with methanol and concentrated in vacuo and the crude product was purified by column chromatography (eluent: 5% to 30% EtOAc/hexanes) to give E (974 mg, 78%) as a gum; $[\alpha]_D^{25}$=+71.2 (c=1.0); $^1$H NMR (400 MHz, CDCl$_3$): δ 7.37-7.26 (m, 5H, ArH), 5.81 (d, J=3.8 Hz, 1H, H-1), 4.67-4.61 (m, 2H, H-2, PhCH$_2$), 4.55 (d, J=12.2 Hz, 1H, PhCH$_2$), 4.12 (ddd, J=9.0, 3.7, 2.1 Hz, 1H, H-4), 3.89-3.84 (m, 2H, H-3, H-5), 3.81 (dd, J=11.5, 2.2 Hz, 1H, OCH$_2$), 3.67-3.58 (m, 2H, OCH$_2$, H-5), 3.45 (ddd, J=13.3, 7.4, 3.5 Hz, 1H, CH$_2$N$_3$), 3.28 (ddd, J=13.3, 5.6, 3.5 Hz, 1H, CH$_2$N$_3$), 1.57 (s, 3H, CH$_3$), 1.35 (s, 3H, CH$_3$); $^{13}$C NMR (101 MHz, CDCl$_3$): δ 137.99 (Ar—C), 128.37 (Ar—C), 127.78 (Ar—C), 127.68 (Ar—C), 112.98 (CMe$_2$), 104.13 (C-1), 78.61 (C-2), 77.89 (C-3), 77.17 (C-4), 73.52 (PhCH$_2$), 69.38 (C-5), 67.65 (OCH$_2$), 50.59 (CH$_2$N$_3$), 26.69 (CH$_3$), 26.58 (CH$_3$); ESI-HRMS: m/z calcd for C$_{17}$H$_{23}$N$_3$O$_5$Na [M+Na]$^+$ 372.1535, found 372.1533

3-O-(2-Azidoethyl)-5-O-benzyl-1,2-di-O-(4-nitrobenzoyl)-α-D-ribofuranose (F). A solution of E (822 mg, 2.36 mmol) in a 1:3 mixture of 1 N aqueous hydrochloric acid and p-dioxane (16 mL) was stirred for 1.5 h at ambient temperature then was concentrated and dried under reduce pressure. The residue was diluted with pyridine (40 mL) and treated with 4-dimethylaminopyridine (30 mg, 0.236 mmol) and p-nitrobenzoyl chloride (1.53 g, 8.26 mmol) at ambient temperature and stirred for 10 h. The reaction mixture was concentrated and the residue was purified by silica gel column chromatography (hexane: ethyl acetate 8:1 to 4:1). to give F as a white foam (643 mg, 1.06 mmol, 45%); $[\alpha]_D^{25}$ =+66.9 (c=1.0); $^1$H NMR (600 MHz, CDCl$_3$) δ32 8.26 (s, 4H, ArH); 8.20 (d, J=8.8 Hz, ArH); 8.12 (d, J=8.8 Hz, ArH); 7.39-7.26 (m, 5H, ArH); 6.80 (d, J=4.4 Hz, 1H, H-1); 5.45 (dd, J=4.4 Hz, 6.6 Hz, 1H, H-2); 4.65 (d, J=11.7 Hz, 1H, PhCH); 4.58 (d, J=11.7 Hz, 1H, PhCH$_2$); 4.58 (m, 1H, H-4); 3.86 (dd, J=6.6 Hz, 2.9 Hz, 1H, H-3); 3.74-3.65 (m, 4H, H-5, CH$_2$CH$_2$N$_3$); 3.33 (m, 1H, CH$_2$CH$_2$N$_3$); 3.28 (m, 1H, CH$_2$CH$_2$N$_3$); $^{13}$C NMR (150 MHz, CDCl$_3$) δ=163.72, 163.56, 150.84, 150.79, 137.47, 131.00, 130.80, 128.55, 127.96, 127.70, 123.65 (18C, ArC.); 95.82 (C-1); 84.70 (C-4); 76.91 (C-3); 73.73 (PhCH$_2$); 73.14 (C-2); 70.33 (—CH$_2$CH$_2$N$_3$); 69.38 (C-5); 51.12 (CH$_2$CH$_2$N$_3$); ESI-HRMS: m/z calcd for C$_{28}$H$_{25}$N$_5$O$_{11}$Na [M+Na]$^+$ 630.1448, found 630.1453.

5-O-α-[3'''-O-(2-Azidoethyl)-5'''-O-benzyl-2'''-O-(4-nitrobenzoyl)-D-ribofuranosyl]-6,2'', 3'', 6''-tetra-O-acetyl-1, 3,2', 4''-tetraazido-6', 7'-oxazolidino-apramycin (Gα) and 5-O-β-[3'''-O-(2-Azidoethyl)-5'''-O-benzyl-2'''-O-(4-nitrobenzoyl)-D-ribofuranosyl]-6,2'', 3'', 6''-tetra-O-acetyl-1, 3,2', 4''-tetraazido-6', 7'-oxazolidino-apramycin (Gβ) 3-O-(2-Azidoethyl)-5-O-benzyl-1,2-di-O-(4-nitrobenzoyl)-α-D-ribofuranose F (181 mg, 0.30 mmol) and apramycin derivative A (100 mg, 0.12 mmol) were charged to a round bottom flask, co-evaporated with toluene three times and dried in vacuo overnight. The flask was purged with argon and the mixture dissolved in dry DCM (1.5 mL) before cooling to 0° C., treatment with BF$_3$.OEt$_2$ (0.23 mL, 0.63 mmol) and stirring for 12 h. The reaction was quenched with triethylamine (0.2 mL), diluted with EtOAc and washed with aqueous NaHCO$_3$ and brine then concentrated. The crude product was purified using silica gel column chromatography (eluent: 20%-40% EtOAc/hexanes) to give Gα (35 mg, 23%) and Gβ (31 mg, 20%); α anomer: $[\alpha]_D^{25}$=+79.1 (c 1.1, DCM); $^1$H NMR (600 MHz, CDCl$_3$): δ 8.32 (d, J=8.6 Hz, 2H, ArH), 8.23 (d, J=8.9 Hz, 2H, ArH), 7.36-7.29 (m, 5H, ArH), 5.68-5.65 (m, 1H, H-2'''), 5.56 (d, J=3.8 Hz, 1H, H-1'''), 5.38 (t, J=10.0 Hz, 1H, H-3''), 5.32 (d, J=3.8 Hz, 1H, H-1''), 5.15 (d, J=3.5 Hz, 1H, H-1), 4.94-4.87 (m, 3H, H-2'', H-6, H-8), 4.75 (dd, J=8.4, 3.1 Hz, 1H, H-6), 4.66 (dd, J=10.5, 3.1 Hz, 1H, H-5), 4.60 (d, J=11.9 Hz, 1H, CH$_2$Ph), 4.54 (d, J=12.0 Hz, 1H, CH$_2$Ph), 4.31 (dd, J=12.1, 1.8 Hz, 1H, H-6''), 4.25 (dt, J=7.0, 3.3 Hz, 1H, H-4'''), 4.21 (dd, J=12.2, 5.2 Hz, 1H, H-6''), 4.04 (dd, J=7.6, 5.1 Hz, 1H, H-3'''), 3.79 (dd, J=8.4, 3.0 Hz, 1H, H-7), 3.75-3.69 (m, 4H, H-4', H-5, H-5', H-5''), 3.68-3.62 (m, 1H, H-3), 3.62-3.57 (m, 3H, H-5''', H-4', OCH$_2$CH$_2$), 3.56-3.48 (m, 3H, H-1, H-4, OCH$_2$CH$_2$), 3.29 (dt, J=12.8, 4.1 Hz, 1H, H-2'), 3.18 (t, J=4.9 Hz, 2H, OCH$_2$CH$_2$), 2.91 (s, 3H, NCH$_3$), 2.42 (dt, J=12.9, 4.4 Hz, 1H, H-2), 2.25 (dt, J=10.6, 4.3 Hz, 1H, H-3), 2.13 (s, 3H, COCH$_3$), 2.11 (s, 3H, COCH$_3$), 2.09 (m, 6H, COCH$_3$), 1.86 (q, J=11.5 Hz, 1H, H-3'), 1.55 (q, J=12.6 Hz, 1H, H-2); $^{13}$C NMR (151 MHz, CDCl$_3$): δ 170.3 (C=O), 169.9 (C=O), 169.8 (C=O), 164.3 (C=O), 156.9 (C=O), 150.9 (Ar—C), 137.5 (Ar—C), 134.6 (Ar—C), 131.1 (Ar—C), 128.5 (Ar—C), 127.9 (Ar—C), 127.8 (Ar—C), 123.8 (Ar—C), 102.8 (C-1'''), 97.8 (C-1), 95.0 (C-8), 94.2 (C-1''), 82.5 (C-5), 80.4 (C-4''), 80.1 (C-4), 77.2 (C-3'''), 73.6 (C-6), 73.6 (CH$_2$Ph), 71.3 (C-2'''), 70.7 (C-3'), 70.0 (C-2''), 69.9 (C-6), 69.9 (OCH$_2$CH$_2$), 68.9 (C-5'''), 68.7 (C-5''), 65.5

(C-5'), 65.2 (C-4'), 62.8 (C-6"), 60.2 (C-7'), 60.1 (C-4"), 58.3 (C-3), 58.1 (C-1), 56.7 (C-2'), 50.6 (OCH$_2$CH$_2$), 31.4 (C-2'), 30.3 (C-3), 29.8 (NCH$_3$), 21.2 (COCH$_3$), 20.8 (COCH$_3$), 20.8 (COCH$_3$), 20.7 (COCH$_3$); ESI-HRMS: m/z calcd. for C$_{51}$H$_{59}$N$_{17}$O$_{23}$ [M+Na]$^+$ 1300.3867; found, 1300.3887; β anomer: [α]$_D^{25}$=+70.8 (c 1.8, DCM); $^1$H NMR (600 MHz, CDCl$_3$): δ 8.28 (d, J=8.6 Hz, 2H, ArH), 8.20 (d, J=8.7 Hz, 2H, ArH), 7.46-7.26 (m, 5H, ArH), 5.79 (d, J=3.4 Hz, 1H, H-1), 5.42 (t, J=10.0 Hz, 1H, H-3'''), 5.38 (s, 1H, H-1'''), 5.37 (d, J=3.8 Hz, 1H, H-1"), 5.23 (d, J=4.2 Hz, 1H, H-2'''), 4.92 (t, J=9.7 Hz, 1H, H-6), 4.86 (dd, J=10.3, 3.8 Hz, 1H, H-2"), 4.81 (d, J=4.4 Hz, 1H, H-8'), 4.76 (dd, J=7.5, 3.2 Hz, 1H, H-6'), 4.60 (d, J=11.9 Hz, 1H, CH$_2$Ph), 4.51 (d, J=11.9 Hz, 1H, CH$_2$Ph), 4.39 (dd, J=10.3, 3.2 Hz, 1H, H-5'), 4.33 (d, J=12.0 Hz, 1H, H-6"), 4.26-4.16 (m, 2H, H-6", H-4"), 4.14 (dd, J=7.1, 4.5 Hz, 1H, H-3'''), 3.84-3.71 (m, 3H, H-5, H-7', H-5"), 3.71-3.52 (m, 8H, H-4, H-4', H-4", H-3, H-5''', OCH$_2$CH$_2$), 3.47-3.37 (m, 1H, H-1), 3.17 (m, 2H, OCH$_2$CH$_2$), 3.09 (dt, J=12.8, 3.9 Hz, 1H, H-2'), 2.94 (s, 3H, NHCH$_3$), 2.41 (dt, J=12.9, 4.3 Hz, 1H, H-2), 2.19-1.99 (m, 13H, 4COCH$_3$, H-3'), 1.88 (q, J=11.8 Hz, 1H, H-3'), 1.57 (q, J=12.6 Hz, 1H, H-2); $^{13}$C NMR (151 MHz, CDCl$_3$): δ 170.4(C=O), 170.1(C=O), 169.8 (C=O), 169.7 (C=O), 163.8 (C=O), 157.1 (C=O), 150.8 (Ar—C), 137.7 (Ar—C), 134.5 (Ar—C), 131.1 (Ar—C), 130.9 (Ar—C), 128.5 (Ar—C), 127.8 (Ar—C), 127.7 (Ar—C), 123.7 (Ar—C), 123.6 (Ar—C), 106.9 (C-1'''), 97.3 (C-1), 96.4 (C-8'), 94.2 (C-1"), 82.0 (C-5), 80.5 (C-4'''), 77.8 (C-4), 76.8 (C-3'''), 75.7 (C-6), 75.0 (CH$_2$Ph), 73.4 (C-2'''), 71.0 (C-3"), 70.4 (C-2"), 70.2 (C-6'), 70.0 (OCH$_2$CH$_2$), 69.7 (C-5'''), 69.1 (C-5"), 65.9 (C-5'), 65.7 (C-4'), 62.9 (C-6"), 60.2 (C-7'), 60.1 (C-4"), 59.1 (C-3), 58.1 (C-1), 56.5 (C-2"), 50.6 (OCH$_2$CH$_2$), 31.3 (C-2), 30.1 (C-3'), 29.7(NCH$_3$), 20.9 (COCH$_3$), 20.8 (COCH$_3$), 20.7 (COCH$_3$), 20.7 (COCH3); ESI-HRMS: m/z calcd. for C$_{51}$H$_{59}$N$_{17}$O$_{23}$ [M+Na]$^+$ 1300.3867; found, 1300.3835.

5-O-α-[3-O-(2-Aminoethyl)-D-ribofuranosyl] apramycin hexaacetate salt (DCWSU123). A stirred solution of compound Gα (30 mg, 0.02 mmol) in dioxane (0.5 mL) was treated with 3N NaOH (0.25 mL) and heated at 100° C. for 18 h. The reaction mixture was cooled to rt and neutralized with glacial acetic acid and concentrated in vacuo. The crude product was passed through a silica gel column (eluent: 50% methanol/DCM). The product-containing fractions was concentrated and dissolved in THF (0.6 mL) followed by the addition of 0.3N NaOH (0.3 mL) and 1M P(CH$_3$)$_3$ in THF (0.3 mL). The reaction mixture was stirred at 55° C. for 2 h then concentrated and purified by column chromatography (eluent: 5% to 50% ammonia/MeOH).

The product-containing fractions were concentrated, dissolved in dioxane:water:glacial acetic acid=1:2:0.2 (0.3 mL). Pd(OH)$_2$/C (0.5 equiv) was added and the reaction mixture was stirred at room temperature under 1 atm of hydrogen (balloon) for 4 h. After completion, the reaction mixture was filtered over Celite®, concentrated to dryness and dissolved in aqueous acetic acid solution (pH 4, 1 mL) before it was charged to a Sephadex column (CM Sephadex C-25). The column was flushed with D.I. water (20 mL), then eluted with a gradient of 0.1%-1.0% NH$_4$OH in D.I. water. The fractions containing the product were combined, acidified with glacial acetic acid and lyophilized to afford DCWSU123 (21 mg, 85%) as the peracetate salt in the form of a white solid; [α]$_D^{25}$=+52.3 (c 1.1, H$_2$O); $^1$H NMR (600 MHz, D$_2$O): δ 5.65 (d, J=3.4 Hz, 1H, H-1'), 5.33 (s, 1H, H-1"), 5.24 (d, J=4.4 Hz, 1H, H-1'''), 5.03 (d, J=8.4 Hz, 1H, H-8'), 4.40 (s, 1H, H-6'), 4.23-4.18 (m, 1H, H-2'''), 4.16 (q, J=3.6 Hz, 1H, H-4'''), 3.87-3.80 (m, 1H, H-4), 3.80-3.64 (m, 8H, H-3", H-4', H-5, H-5", H-3''', H-6", OCH$_2$CH$_2$), 3.64-3.41 (m, 7H, H-6", H-5', H-6, H-5''', H-2', H-5', H-2"), 3.29-3.11 (m, 3H, H-1, H-3, H-7'), 3.05 (m, 3H, OCH$_2$CH$_2$, H-4"), 2.60 (s, 3H, NCH$_3$), 2.29-2.16 (m, 2H, H-2, H-3'), 1.91-1.80 (m, 1H, H-3'), 1.66-1.56 (m, 1H, H-2); $^{13}$C NMR (151 MHz, D$_2$O): δ 102.8 (C-1'''), 95.1 (C-1'), 94.4 (C-1"), 92.9 (C-8"), 84.3 (C-5), 83.2 (C-4'''), 78.4 (C-4), 78.0 (C-3'''), 71.6 (C-6), 70.9 (C-2'''), 70.3 (C-5"), 69.8 (C-2"), 68.7 (C-4'), 66.8 (OCH$_2$CH$_2$), 66.0 (C-5'), 62.8 (C-6'), 61.5 (C-5'''), 60.3 (C-6"), 59.5 (C-7'), 52.0 (C-4"), 50.0 (C-3), 48.6 (C-1'), 47.8 (C-2'), 39.1 (OCH$_2$CH$_2$), 30.1 (NCH$_3$), 29.2 (C-2), 27.0 (C-3'); ESI-HRMS: m/z calcd. for C$_{28}$H$_{55}$N$_6$O$_{15}$ [M+H]$^+$ 715.3725; found, 715.3742.

5-O-β-(3'''-O-(2-Aminoethyl)-D-ribofuranosyl) apramycin hexaacetate salt (DCWSU124). Substrate Gβ (35 mg, 0.03 mmol) was deprotected in the same manner as compound Gα to yield DCWSU124 (30 mg, 95%) as a pentaacetate salt in the form of a white solid; [α]$_D^{25}$=68.92 (c 0.5, H$_2$O); $^1$H NMR (600 MHz, D$_2$O): δ 5.64 (d, J=3.6 Hz, 1H, H-1'), 5.28 (d, J=3.7 Hz, 1H, H-1"), 5.16 (s, 1H, H-1'''), 5.00 (d, J=8.5 Hz, 1H, H-8'), 4.37 (s, 1H, H-6'), 4.19 (d, J=2.9 Hz, 1H, H-2'''), 3.97-3.88 (m, 1H, H-4'''), 3.86-3.54 (m, 12H, H-4, H-3''', H-3", H-5''', H-6", H-5", H-4', H-5, H-2', OCH$_2$CH$_2$), 3.53-3.39 (m, 5H, H-2', H-5', H-5''', H-2", H-6), 3.31-3.21 (m, 1H, H-3), 3.18 (d, J=8.4 Hz, 1H, H-7'), 3.16-3.08 (m, 1H, H-1), 3.05 (t, J=10.3 Hz, 1H, H-4"), 3.01 (t, J=4.8 Hz, 2H, OCH$_2$CH$_2$), 2.57 (s, 3H, NHCH$_3$), 2.24 (dd, J=8.6, 4.0 Hz, 1H, H-2), 2.20-2.09 (m, 1H, H-3'), 1.84 (q, J=11.9 Hz, 1H, H-3'), 1.66-1.59 (m, 1H, H-2); $^{13}$C NMR (151 MHz, D$_2$O): δ 110.5 (C-1'''), 94.5 (C-1'), 94.3 (C-1"), 92.8 (C-8'), 84.9 (C-5), 81.0 (C-4'''), 77.0 (C-3'''), 75.8 (C-4), 73.2 (C-2"), 72.5 (C-6), 70.2 (C-5"), 69.6 (C-2"), 69.5 (C-3"), 68.4 (C-4'), 66.0 (C-5'), 65.9 (OCH$_2$CH$_2$), 62.6 (C-6'), 61.0 (C-5'''), 60.2 (C-6"), 59.3 (C-7'), 51.9 (C-4"), 49.8 (C-3), 48.3 (C-1), 47.8 (C-2'), 39.2 (OCH$_2$CH$_2$), 30.0 (NCH$_3$), 28.5 (C-2), 26.7 (C-3); ESI-HRMS: m/z calcd. for C$_{28}$H$_{55}$N$_6$O$_{15}$ [M+H]$^+$ 715.3725; found, 715.3690.

5-O-β-(3'''-O-(2-Aminoethyl)-D-ribofuranosyl) apramycin hexaacetate salt (DCWSU124). Substrate Gβ (35 mg, 0.03 mmol) was deprotected in the same manner as compound Gα to yield DCWSU124 (30 mg, 95%) as a pentaacetate salt in the form of a white solid; [α]$_D^{25}$=68.92 (c 0.5, H2O); $^1$H NMR (600 MHz, D$_2$O): δ 5.64 (d, J=3.6 Hz, 1H, H-1'), 5.28 (d, J=3.7 Hz, 1H, H-1"), 5.16 (s, 1H, H-1'''), 5.00 (d, J=8.5 Hz, 1H, H-8'), 4.37 (s, 1H, H-6'), 4.19 (d, J=2.9 Hz, 1H, H-2'''), 3.97-3.88 (m, 1H, H-4'''), 3.86-3.54 (m, 12H, H-4, H-3''', H-3", H-5''', H-6", H-5", H-4', H-5, H-2', OCH$_2$CH$_2$), 3.53-3.39 (m, 5H, H-2', H-5', H-5''', H-2", H-6), 3.31-3.21 (m, 1H, H-3), 3.18 (d, J=8.4 Hz, 1H, H-7'), 3.16-3.08 (m, 1H, H-1), 3.05 (t, J=10.3 Hz, 1H, H-4"), 3.01 (t, J=4.8 Hz, 2H, OCH$_2$CH$_2$), 2.57 (s, 3H, NHCH$_3$), 2.24 (dd, J=8.6, 4.0 Hz, 1H, H-2), 2.20-2.09 (m, 1H, H-3'), 1.84 (q, J=11.9 Hz, 1H, H-3'), 1.66-1.59 (m, 1H, H-2); $^{13}$C NMR (151 MHz, D$_2$O): δ 110.5 (C-1'''), 94.5 (C-1'), 94.3 (C-1"), 92.8 (C-8'), 84.9 (C-5), 81.0 (C-4'''), 77.0 (C-3'''), 75.8 (C-4), 73.2 (C-2"), 72.5 (C-6), 70.2 (C-5"), 69.6 (C-2"), 69.5 (C-3"), 68.4 (C-4'), 66.0 (C-5'), 65.9 (OCH$_2$CH$_2$), 62.6 (C-6'), 61.0 (C-5'''), 60.2 (C-6"), 59.3 (C-7'), 51.9 (C-4"), 49.8 (C-3), 48.3 (C-1), 47.8 (C-2'), 39.2 (OCH$_2$CH$_2$), 30.0 (NCH$_3$), 28.5 (C-2), 26.7 (C-3); ESI-HRMS: m/z calcd. for C$_{28}$H$_{55}$N$_6$O$_{15}$ [M+H]$^+$ 715.3725; found, 715.3690.

Example 4

DCWSU131

Figure 2:
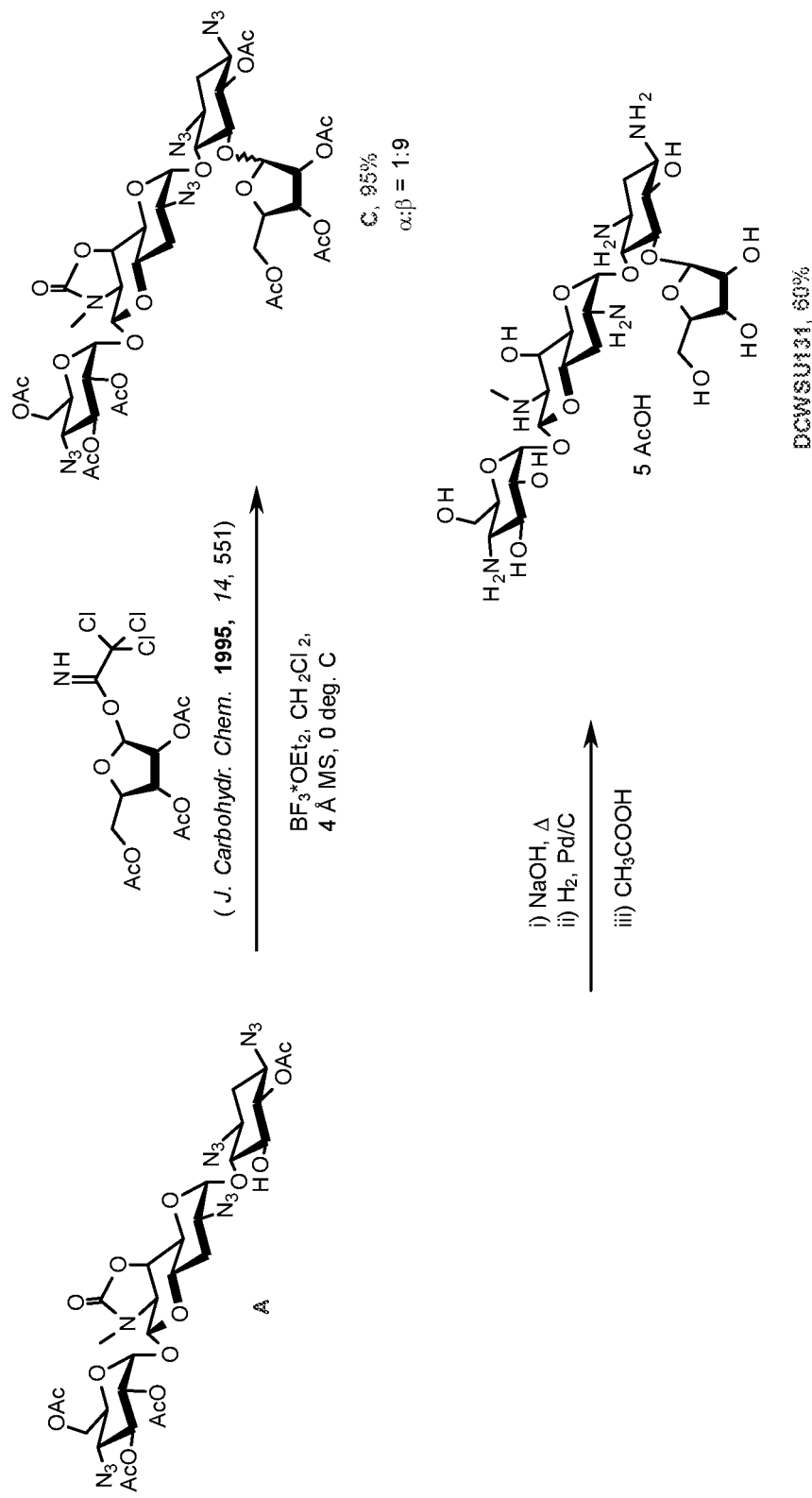

See the synthetic scheme of FIG. 2.

5-O-β-[2''',3''',5'''-Tri-O-acetyl-D-ribofuranosyl]-6,2'', 3'', 6''-tetra-O-acetyl-1,3,2', 4''-tetraazido-6', 7'-oxazolidino-apramycin (C). A suspension of 2,3,5-tri-O-acetyl-D-ribofuranosyl trichloroacetimidate 125 (150 mg, 0.36 mmol), acceptor A (100 mg, 0.12 mmol) and activated 4 Å MS in dry DCM was stirred at rt for 1 h before cooling to 0° C. and addition of $BF_3.OEt_2$ (132 μL, 0.54 mmol). After 4 h of stirring at 0° C., the reaction was quenched with triethylamine (0.5 mL) and filtered through Celite®. The reaction mixture was diluted with EtOAc and washed with aqueous $NaHCO_3$ and brine then concentrated. The crude product was purified using silica gel column chromatography (eluent: 20%-40% EtOAc/hexanes) to give C α:β=1.9 (126 mg, 95%), further purification was done to give C (47 mg) as the β-anomer in the form of a white solid with the remainder of the product isolated as a mixtures of anomers. $[α]_D^{25}$=+47.2 (c 2.7, DCM); $^1$H NMR (600 MHz, $CDCl_3$): δ 5.637 (d, J=3.5 Hz, 1H, H-1'), 5.43 (d, J=10.1 Hz, 1H, H-3''), 5.40 (d, J=2.3 Hz, 1H, H-1'''), 5.37 (d, J=3.8 Hz, 1H, H-1''), 5.11 (t, J=5.0 Hz, 1H, H-3'''), 5.07 (dd, J=4.9, 3.3 Hz, 1H, H-2'''), 4.92 (t, J=9.9 Hz, 1H, H-6), 4.85 (dd, J=10.4, 3.9 Hz, 1H, H-2''), 4.82 (d, J=4.6 Hz, 1H, H-8'), 4.76 (dd, J=7.4, 3.3 Hz, 1H, H-6'), 4.41 (dd, J=10.3, 3.3 Hz, 1H, H-5'), 4.32 (m, 2H, H-6'', H-5'''), 4.24 (q, J=4.0 Hz, 1H, H-4'''), 4.21 (dd, J=12.2, 5.4 Hz, 1H, H-6''), 4.09 (dd, J=12.1, 4.1 Hz, 1H, H-5'''), 3.79 (d, J=9.2 Hz, 1H, H-5), 3.77-3.64 (m, 4H, H-4, H-7', H-4', H-5''), 3.60-3.53 (m, 2H, H-4'', H-3), 3.46-3.38 (m, 1H, H-1), 3.22 (dt, J=12.9, 4.1 Hz, 1H, H-2'), 2.93 (s, 3H, $NCH_3$), 2.41 (dt, J=13.0, 4.5 Hz, 1H, H-2), 2.26-2.21 (m, 1H, H-3'), 2.20 (s, 3H, $COCH_3$), 2.14-2.02 (m, 18H, 6*$COCH_3$), 1.93 (q, J=11.7 Hz, 1H, H-3'), 1.58 (q, J=12.6 Hz, 1H, H-2); $^{13}$C NMR (151 MHz, $CDCl_3$): δ 170.8 (C=O), 170.4 (C=O), 170.2 (C=O), 169.8 (C=O), 169.6 (C=O), 169.5 (C=O), 169.5 (C=O), 157.0 (C=O), 106.1 (C-1'''), 97.4 (C-8'), 96.4 (C-1'), 94.0 (C-1''), 80.4 (C-5), 79.5 (C-4'''), 77.5 (C-4), 74.5 (C-6), 74.1 (C-2'''), 71.0 (C-6'), 70.9 (C-3'''), 70.3 (C-3''), 69.9 (C-2''), 69.1 (C-5''), 66.0 (C-5'), 65.7 (C-4'), 63.4 (C-5'''), 62.9 (C-6''), 60.2 (C-7'), 60.1 (C-4''), 59.1 (C-3), 58.1 (C-1), 56.6 (C-2'), 31.5 (C-2), 30.1 ($NCH_3$), 29.9 (C-3'), 20.8 ($COCH_3$), 20.8 ($COCH_3$), 20.7 ($COCH_3$), 20.7 ($COCH_3$), 20.7 ($COCH_3$), 20.4 ($COCH_3$), 20.4 ($COCH_3$); ESI-HRMS: m/z calcd. for $C_{41}H_{54}N_{13}O_{23}$ $[M+H]^+$ 1118.3275; found, 1118.3234.

5-O—(β-D-Ribefuranosyl) apramycin pentaacetate salt (DCWSU131) A stirred solution of substrate C (47 mg, 0.04 mmol) in dioxane (0.5 mL) was treated with 3 N NaOH (0.25 mL) and heated at 100° C. for 12 h. The reaction mixture was cooled to rt and neutralized with glacial acetic acid before it was concentrated in vacuo. The crude product was purified through a silica gel column (eluent: 10-20% methanol/DCM). The product-containing fractions were concentrated, dissolved in dioxane:water:glacial acetic acid=1:2:0.2 (0.3 mL) and Pd/C (0.5 equiv) was added. The reaction mixture was stirred at room temperature under 1 atm of hydrogen (balloon) for 1 h. After completion, the reaction mixture was filtered over Celite® and the filtrate concentrated to dryness and dissolved in aqueous acetic acid solution (pH 4, 1 mL) before it was charged to a Sephadex column (CM Sephadex C-25). The column was flushed with D.I. water (20 mL), then eluted with a gradient of 0.1%-1.0% $NH_4OH$ in D.I. water. The fractions containing the product were combined, acidified with glacial acetic acid and lyophilized to afford DCWSU131 (29 mg, 69%) as the pentaacetate salt in the form of a white solid $[α]_D^{25}$=+66.25 (c 0.8, $H_2O$); $^1$H NMR (600 MHz, $D_2O$): δ 5.66 (d, J=4.0 Hz, 1H, H-1'), 5.29 (d, J=3.8 Hz, 1H, H-1''), 5.14 (s, 1H, H-1'''), 5.01 (d, J=8.5 Hz, 1H, H-8'), 4.38 (s, 1H, H-6'), 4.00 (d, J=4.7 Hz, 1H, H-2'''), 3.98-3.93 (m, 1H, H-3'''), 3.86-3.74 (m, 3H, H-4''', H-4, H-3''), 3.74-3.63 (m, 5H, H-4', H-5, H-5'', H-5''', H-6''), 3.58 (dd, J=12.4, 4.4 Hz, 1H, H-6''), 3.53-3.41 (m, 5H, H-5', H-2', H-2'', H-6, H-5'''), 3.29-3.21 (m, 1H, H-3), 3.19 (dd, J=8.5, 2.4 Hz, 1H, H-7'), 3.12 (td, J=11.6, 4.3 Hz, 1H, H-1), 3.06 (t, J=10.4 Hz, 1H, H-4''), 2.58 (s, 3H, $NCH_3$), 2.24 (dt, J=11.3, 3.1 Hz, 1H, H-2), 2.21-2.10 (m, 1H, H-3'), 1.92-1.81 (m, 1H, H-3'), 1.66-1.57 (m, 1H, H-2); $^{13}$C NMR (151 MHz, $D_2O$): δ 110.3 (C-1'''), 94.5 (C-1'), 94.3 (C-1''), 92.8 (C-8'), 84.9 (C-5), 82.3 (C-4'''), 75.9 (C-4), 75.1 (C-2''') 72.5 (C-6), 70.2 (C-5''), 69.6 (C-2''), 69.6 (C-4'), 68.9 (C-3''), 68.4 (C-3''), 66.0 (C-5'), 62.6 (C-6'), 60.8 (C-5'''), 60.2 (C-6''), 59.3 (C-7'), 52.0 (C-4''), 49.8 (C-3), 48.3 (C-1), 47.8 (C-2'), 30.0 ($NCH_3$), 28.6 (C-2), 26.7 (C-3'); ESI-HRMS: m/z calcd. for $C_{26}H_{49}N_5NaO_{15}$ $[M+Na]^+$ 694.3123; found, 694.3122.

Example 5

DCWSU 138

Figure 3:
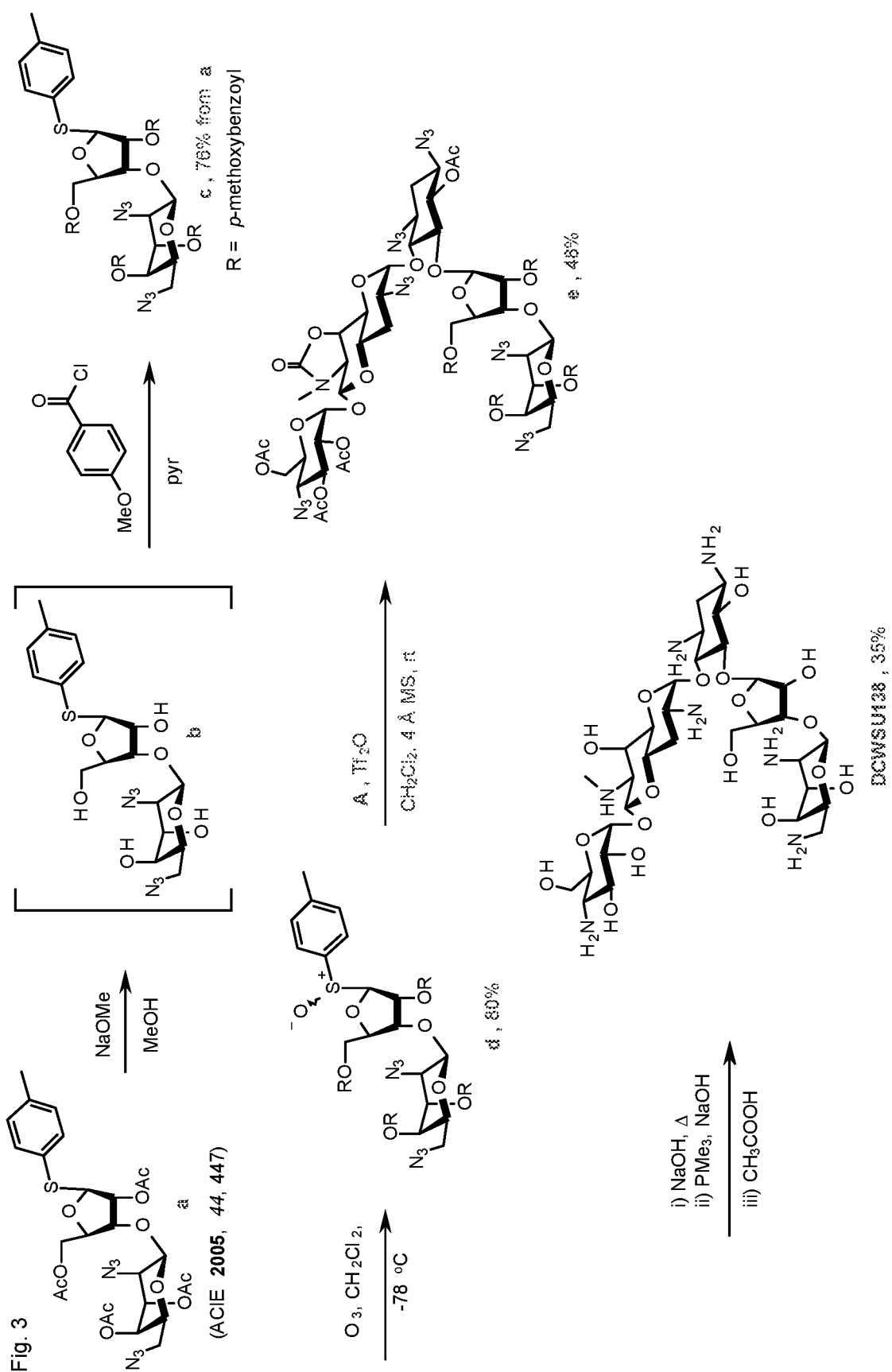

See the synthetic scheme of FIG. 3.

p-Cresyl-2',6'-diazido-2,5,3'4'-tetra(4-methoxybenzoyl)-1-thio-β-paromobioside (c). p-Cresyl-2',6'-diazido-2,5,3'4'-tetra-O-acetyl-α-thioparomobioside a (375 mg, 0.59 mmol) was dissolved in dry methanol, then NaOMe (4.7 mg, 0.12 mmol) was added and the reaction mixture was stirred for 1.5 h. The reaction was quenched with glacial acetic acid and concentrated till dryness. The crude product was dissolved in pyridine (5 mL) and p-methoxybenzoyl chloride (802 mg, 4.72 mmol) was added followed by stirring for 48 h then diluting with EtOAc. The organic layer was washed with aqueous $NaHCO_3$ followed by brine, dried with $Na_2SO_4$, and concentrated. The crude product was purified via silica gel chromatography eluting with 10% to 40% EtOAc in hexanes to give c (398 mg, 76%) as a white solid; $[α]_D^{25}$=−14.2 (c 13.2, DCM); $^1$H NMR (600 MHz, $CDCl_3$): -δ 8.08 (d, J=8.8 Hz, 2H, ArH), 8.04 (d, J=8.8 Hz, 2H, ArH), 7.95 (d, J=8.8 Hz, 2H, ArH), 7.85 (d, J=8.9 Hz, 2H, ArH), 7.40 (d, J=8.0 Hz, 2H, ArH), 7.02 (d, J=7.8 Hz, 2H, ArH), 6.97-6.88 (m, 6H, ArH), 6.78 (d, J=8.9 Hz, 2H, ArH), 5.51 (d, J=4.5 Hz, 1H, H-1), 5.43 (t, J=4.9 Hz, 1H, H-2), 5.23 (t, J=2.8 Hz, 1H, H-3'), 5.16 (d, J=1.8 Hz, 1H, H-1'), 5.04 (d, J=1.8 Hz, 1H, H-4'), 4.78 (t, J=5.6 Hz, 1H, H-3), 4.68 (dd, J=12.0, 2.7 Hz, 1H, H-5), 4.56 (td, J=5.8, 5.2, 2.7 Hz, 1H, H-4), 4.50 (dd, J=12.1, 4.6 Hz, 1H, H-5'), 4.24 (ddd, J=8.5, 4.1, 1.9 Hz, 1H, H-5'), 3.87 (s, 3H, $OCH_3$), 3.85-3.73 (m, 9H, 3 $OCH_3$), 3.57 (dd, J=13.1, 8.4 Hz, 1H, H-6'), 3.41 (t, J=2.2 Hz, 1H, H-2'), 3.27 (dd, J=13.1, 4.0 Hz, 1H, H-6'), 2.22 (s, 3H, $CH_3$); 13C NMR (151 MHz, $CDCl_3$): δ 166.0 (C=O), 165.4 (C=O), 165.0 (C=O), 164.03 (C=O), 163.97 (Ar—C), 163.9 (Ar—C), 163.7 (Ar—C), 163.4 (Ar—C), 138.6 (Ar—C), 133.9 (Ar—C), 132.3 (Ar—C), 132.0 (Ar—C), 131.9 (Ar—C), 131.8 (Ar—C), 129.8 (Ar—C), 127.7 (Ar—C), 122.3 (Ar—C), 121.1 (Ar—C), 120.9 (Ar—C), 120.8 (Ar—C), 99.3 (C-1'), 88.2 (C-1), 81.2 (C-4), 76.7 (C-3), 74.5 (C-2), 74.2 (C-5'), 69.1 (C-3'), 65.7 (C-4'), 63.8 (C-5), 56.9 (C-2'), 55.52 ($OCH_3$), 55.46 ($OCH_3$), 55.4 (2 $OCH_3$), 50.8 (C-6'), 21.1 ($CH_3$); ESI-HRMS: m/z calcd. for $C_{50}H_{48}N_6NaO_{15}S$ $[M+Na]^+$ 1027.2796; found, 1027.2749.

p-Cresyl-2',6'-diazido-2,5,3'4'-tetra(4-methoxybenzoyl)-β-thio-paromobiosyl S-oxide (d). A solution of compound c (198 mg, 0.2 mmol) in dry DCM (15 mL) was cooled to −78° C. before ozone gas was bubbled in for 5 min till the solution turned blue. The solution was then warmed to rt, concentrated and the crude product purified by gradient chromatography over silica gel (eluent: 40% EtOAc/hexanes) to give d (162 mg, 80%) as a white solid; $[\alpha]_D^{25}$=+60.0 (c 0.5, DCM); $^1$H NMR (400 MHz, CDCl$_3$): δ 8.16 (d, J=9.0 Hz, 2H, ArH), 8.12-8.03 (m, 4H, ArH), 7.68 (d, J=9.0 Hz, 2H, ArH), 7.51 (d, J=8.2 Hz, 2H, ArH), 7.24 (d, J=7.9 Hz, 2H, ArH), 7.00 (d, J=9.0 Hz, 2H, ArH), 6.96 (d, J=4.3 Hz, 2H, ArH), 6.93 (d, J=4.4 Hz, 2H, ArH), 6.78 (d, J=9.0 Hz, 2H, ArH), 6.14 (dd, J=5.0, 1.9 Hz, 1H, H-2), 5.28 (d, J=1.6 Hz, 1H, H-1'), 5.23 (t, J=2.7 Hz, 1H, H-3'), 5.09-5.03 (m, 1H, H-4'), 5.00 (dd, J=7.1, 5.1 Hz, 1H, H-3), 4.90 (d, J=1.9 Hz, 1H, H-1), 4.76 (dd, J=11.3, 1.5 Hz, 1H, H-5), 4.64-4.52 (m, 2H, H-5, H-4), 4.28 (ddd, J=7.7, 4.4, 1.7 Hz, 1H, H-5'), 3.92 (s, 3H, OCH$_3$), 3.86 (s, 3H, OCH$_3$), 3.85 (s, 3H, OCH$_3$), 3.82 (s, 3H, OCH$_3$), 3.54 (dd, J=13.0, 8.1 Hz, 1H, H-6'), 3.42-3.36 (m, 1H, H-2'), 3.32 (dd, J=13.0, 4.5 Hz, 1H, H-6'), 2.30 (s, 3H, CH$_3$); $^{13}$C NMR (101 MHz, CDCl$_3$): δ 166.0 (C=O), 165.0 (C=O), 164.8 (C=O), 164.1 (C=O), 163.94 (Ar—C), 163.86 (Ar—C), 163.6 (Ar—C), 142.2 (Ar—C), 136.6 (Ar—C), 132.3 (Ar—C), 132.1 (Ar—C), 131.9 (Ar—C), 131.7 (Ar—C), 130.0 (Ar—C), 124.6 (Ar—C), 122.1 (Ar—C), 121.1 (Ar—C), 121.0 (Ar—C), 120.6 (Ar—C), 113.94 (Ar—C), 113.86 (Ar—C), 113.8 (Ar—C), 113.7 (Ar—C), 100.1 (C-1), 99.1 (C-1), 81.6 (C-4), 75.9 (C-3), 74.1 (C-5'), 70.1 (C-2), 69.1 (C-3'), 65.7 (C-4'), 62.7 (C-5), 56.7 (C-2'), 55.54 (OCH$_3$), 55.46 (OCH$_3$), 55.4 (OCH$_3$), 50.7 (C-6'); ESI-HRMS: m/z calcd. for C$_{50}$H$_{48}$N$_6$NaO$_{16}$S [M+Na]$^+$ 1043.2745; found, 1043.2717.

5-O-β-[2'''',6''''-Diazido-2''',5''',3''''4''''-tetra(4-methoxybenzoyl) paromobiosyl]-6,2'',3'',6''-tetra-O-acetyl-1,3,2',4''-tetraazido-6',7'-oxazolidino-apramycin (e). A suspension of donor d (140 mg, 0.14 mmol), acceptor 124 (150 mg, 0.18 mmol) and activated 4 Å MS in dry DCM (2 mL) was stirred at rt for 1 h before addition of freshly distilled triflic anhydride (33 μL, 0.2 mmol). After 5 h of stirring at rt, the reaction was quenched with triethylamine (0.1 mL) and filtered through Celite® then concentrated in vacuo. The crude product was purified by flash column chromatography on silica gel (20% EtOAc/toluene) to afford e (113 mg, 48%) as a white foam; $[\alpha]_D^{25}$=+84.9 (c 0.3, DCM);$^1$H NMR (600 MHz, CDCl$_3$): δ 8.10-8.04 (m, 4H, ArH), 8.02 (d, J=8.9 Hz, 2H, ArH), 7.83 (d, J=8.9 Hz, 2H, ArH), 7.01-6.94 (m, 4H, ArH), 6.92 (d, J=8.9 Hz, 2H, ArH), 6.82 (d, J=9.0 Hz, 2H, ArH), 5.58 (d, J=3.5 Hz, 1H, H-1'), 5.44 (d, J=1.7 Hz, 1H, H-1'''), 5.39 (t, J=10.0 Hz, 1H, H-3''), 5.33 (d, J=3.8 Hz, 1H, H-1''), 5.24-5.18 (m, 2H, H-2''', H-3''''), 5.14 (d, J=1.5 Hz, 1H, H-1''''), 5.07-5.04 (m, 1H, H-4'''), 4.89-4.80 (m, 4H, H-2', H-5''', H-6, H-8'), 4.77-4.72 (m, 2H, H-3''', H-6'), 4.50-4.44 (m, 2H, H-4''', H-5'''), 4.43 (dd, J=10.4, 3.3 Hz, 1H, H-5'), 4.32-4.26 (m, 2H, H-5'''', H-6''), 4.20 (dd, J=12.2, 5.4 Hz, 1H, H-6''), 3.87 (s, 3H, OCH$_3$), 3.85 (s, 3H, OCH$_3$), 3.83 (s, 3H, OCH$_3$), 3.81 (s, 3H, OCH$_3$), 3.75-3.68 (m, 3H, H-5, H-5'', H-7'), 3.64-3.49 (m, 4H, H-3, H-4', H-4'', H-6''''), 3.41-3.30 (m, 4H, H-1, H-2'''', H-4, H-6''''), 3.12 (dt, J=12.9, 4.1 Hz, 1H, H-2'), 2.92 (s, 3H, NCH$_3$), 2.38 (dt, J=12.9, 4.4 Hz, 1H, H-2), 2.17-2.12 (m, 1H, H-3'), 2.11-2.07 (m, 9H, 3COCH$_3$), 2.03 (s, 3H, COCH$_3$), 1.88-1.81 (m, 1H, H-3'), 1.44 (q, J=12.6 Hz, 1H, H-2); $^{13}$C NMR (151 MHz, CDCl$_3$): δ 170.4 (C=O), 170.1 (C=O), 169.9 (C=O), 169.6 (C=O), 165.9 (C=O), 165.5 (C=O), 165.0 (C=O), 164.1 (C=O), 164.0 (Ar—C), 163.9 (Ar—C), 163.8 (Ar—C), 163.6 (Ar—C), 157.1 (C=O), 132.3 (Ar—C), 132.1 (Ar—C), 131.8 (Ar—C), 122.2 (Ar—C), 121.1 (Ar—C), 121.0 (Ar—C), 120.7 (Ar—C), 113.9 (Ar—C), 113.9 (Ar—C), 113.9 (Ar—C), 113.8 (Ar—C), 106.8 (C-1''''), 99.3 (C-1''''), 96.9 (C-1'), 96.6 (C-8'), 94.1 (C-1''), 81.4 (C-5), 79.9 (C-4'''), 78.0 (C-4), 75.7 (C-3''), 74.9 (C-6), 74.5 (C-5''''), 74.2 (C-3''), 70.8 (C-3''''), 70.5 (C-6), 69.9 (C-2''), 69.2 (C-2''''), 69.0 (C-5''), 65.7 (C-4''''), 65.6 (C-5'), 63.0 (C-5''''), 62.9 (C-6''), 60.1 (C-7', C-3), 58.8 (C-4''), 58.1 (C-1), 56.8 (C-2''''), 56.6 (C-2'), 55.5 (OCH$_3$), 55.5 (OCH$_3$), 50.7 (C-6''''), 31.2 (C-2'), 30.4 (C-3'), 30.0 (NCH$_3$), 21.0 (COCH$_3$), 20.8 (COCH$_3$), 20.8 (COCH$_3$), 20.7 (COCH$_3$); ESI-HRMS: m/z calcd. for C$_{73}$H$_{79}$N$_{19}$NaO$_{31}$ [M+Na]$^+$ 1740.5087; found, 1740.5109.

5-O-β-(Paromobiosyl) apramycin heptaacetate salt (DCWSU138). A stirred solution of compound e (40 mg, 0.02 mmol) in dioxane (0.5 mL) was treated with 3N NaOH (0.5 mL) and heated at 120° C. for 2 h. The reaction mixture was cooled to rt and neutralized with glacial acetic acid before it was concentrated in vacuo. The crude product was purified with silica gel column chromatography (eluent: 5%-15% methanol/DCM) to give a residue that was directly subjected to Staudinger reaction by dissolving in THF (0.6 mL) followed by the addition of 0.3N NaOH (0.3 mL) and 1M P(CH$_3$)$_3$ in THF (0.3 mL). The reaction mixture was stirred at 55° C. for 2 h, then concentrated and purified by column chromatography (eluent: 5% to 50% ammonia/MeOH). The product-containing fractions were concentrated and dissolved in D.I. water (1 mL), acidified by glacial acetic acid till pH=3-4 and loaded to a Sephadex column (CM Sephadex C-25) from which the product was flushed with D.I. water (20 mL), then gradient elution of 0.1%-1.0% NH$_4$OH in D.I. water. The fractions containing the product were combined, acidified with glacial acetic acid and lyophilized to afford DCWSU138 (8 mg, 35%) as a peracetate salt in the form of a white foam; $[\alpha]_D^{25}$=+54.4 (c 0.5, H$_2$O);$^1$H NMR (600 MHz, D$_2$O): δ 5.68 (d, J=3.9 Hz, 1H, H-1'), 5.32 (d, J=3.9 Hz, 1H, H-1''), 5.22 (d, J=2.4 Hz, 1H, H-1'''), 5.10 (d, J=1.4 Hz, 1H, H-1''''), 5.03 (d, J=8.5 Hz, 1H, H-8'), 4.41 (s, 1H, H-6'), 4.31 (t, J=5.7 Hz, 1H, H-3'''), 4.21 (dd, J=3.8, 2.8 Hz, 1H, H-2'''), 4.15-4.09 (m, 1H, H-5''''), 4.08-4.00 (m, 2H, H-3'''', H-4''''), 3.83 (t, J=9.7 Hz, 1H, H-4), 3.79 (dt, J=10.2, 3.9 Hz, 1H, H-5''), 3.77-3.65 (m, 5H, H-5''', H-3'', H-4', H-5, H-6''), 3.65-3.58 (m, 2H, H-4'''', H-6''), 3.58-3.44 (m, 5H, H-6, H-6-2', H-5', H-2'', H-5'''), 3.39 (s, 1H, H-2''), 3.32-3.25 (m, 1H, H-3), 3.25-3.19 (m, 2H, H-7', H-6''''), 3.19-3.12 (m, 2H, H-1, H-6''''), 3.09 (t, J=10.3 Hz, 1H, H-4''), 2.60 (s, 3H, NCH$_3$), 2.27 (dt, J=11.8, 3.1 Hz, 1H, H-2), 2.22-2.13 (m, 1H, H-3'), 1.87 (dd, J=24.1, 11.8 Hz, 1H, H-3'), 1.64 (q, J=13.0 Hz, 1H, H-2); $^{13}$C NMR (151 MHz, D$_2$O): δ 110.1 (C-1'''), 95.3 (C-1''''), 94.5 (C-1'), 94.4 (C-1''), 92.8 (C-8'), 84.9 (C-5), 81.3 (C-4'''), 76.0 (C-4), 75.2 (C-3'''), 73.4 (C-2'''), 72.5 (C-2''), 70.2 (C-5''''), 70.1 (C-5''), 69.7 (C-6), 69.5 (C-5'), 68.4 (C-3''), 67.5 (C-3''''), 67.2 (C-4''''), 65.9 (C-4'), 62.6 (C-6'), 60.2 (C-5'''), 60.0 (C-6''), 59.3 (C-7'), 52.0 (C-4''), 50.7 (C-2''''), 49.8 (C-1), 48.4 (C-3), 47.8 (C-2'), 40.3 (C-6''''), 30.0 (NCH$_3$), 28.6 (C-2), 26.7 (C-3); ESI-HRMS: m/z calcd. for C$_{32}$H$_{62}$N$_7$O$_{18}$ [M+H]$^+$ 832.4151; found, 832.4131.

Example 6

DCWSU146

Figure 4:
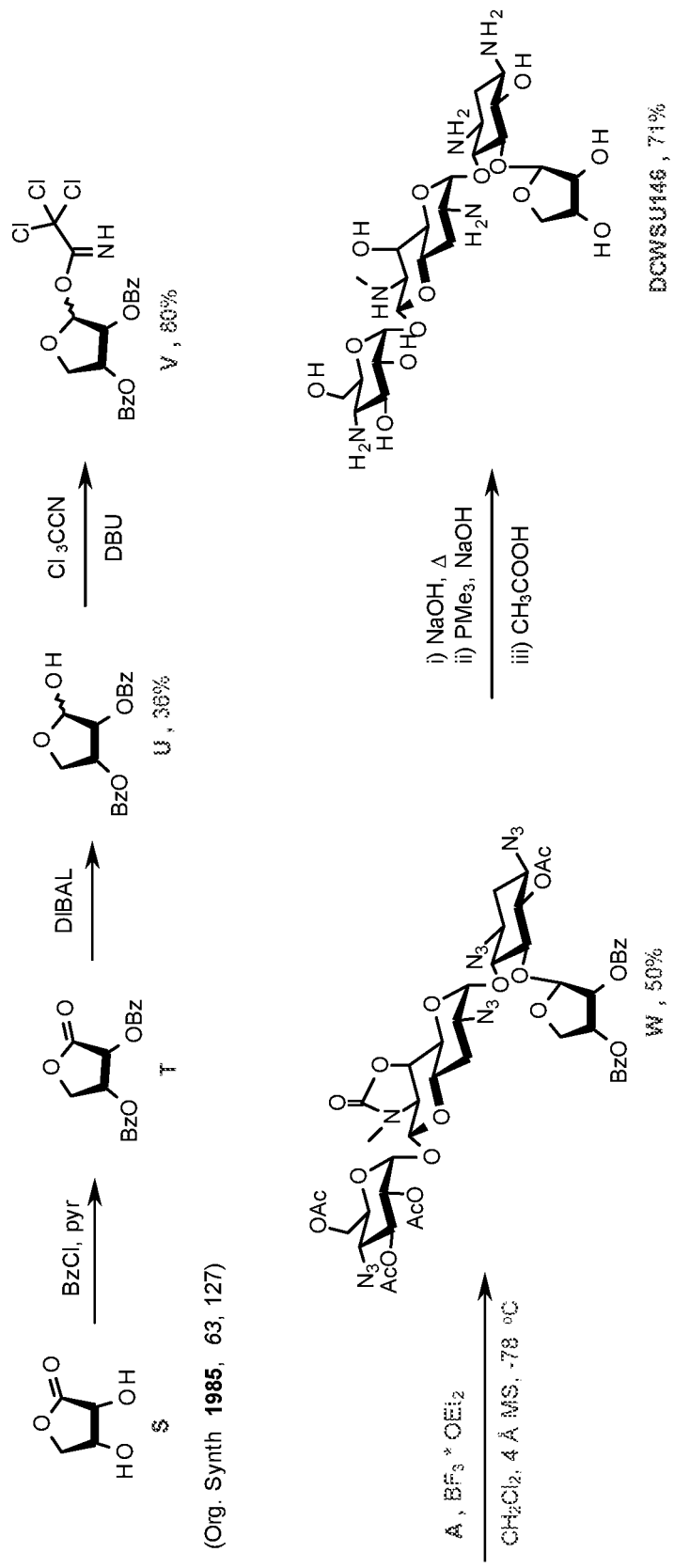

See the synthetic scheme of FIG. 4.

Erythrolactone 2,3-di-O-benzoate (T). An aqueous solution of isoascorbic acid (7.04 g, 40 mmol) in water (100 mL)

was ice-cooled and $Na_2CO_3$ (8.48 g, 80 mmol) was added slowly followed by aqueous solution of $H_2O_2$ (30%, 9.2 mL). The reaction mixture was stirred at 42° C. for 30 min after which charcoal (2 g) was added and the mixture stirred at 75° C. for 30 min to destroy excess $H_2O_2$. The reaction mixture was filtered while hot and neutralized with 6 N HCl then concentrated till dryness. The resulting residue was dissolved in dry pyridine (50 mL) and cooled to 0° C. before addition of benzoyl chloride dropwise (11.6 mL, 100 mmol). The reaction mixture was stirred at rt for 12 h before it was diluted with EtOAc and washed with aqueous $NaHCO_3$ and brine. The organic layer was dried over $Na_2SO_4$ and concentrated. The residue was purified by gradient chromatography over silica gel (eluent: 10% to 35% EtOAc in hexanes) to give T (9.0 g, 69%) as a white solid; $[\alpha]_D^{25}=-145.78$ (c 1.2, DCM); $^1$H NMR (400 MHz, $CDCl_3$): δ 7.97 (m, 4H), 7.65-7.50 (m, 2H, ArH), 7.41 (m, 2H, ArH), 7.35 (m, 2H, ArH), 6.07-5.95 (m, 2H, H-2, H-3), 4.73 (dd, J=11.4, 3.1 Hz, 1H, H-4), 4.65 (d, J=11.4 Hz, 1H, H-4); $^{13}$C NMR (101 MHz, CDCL3): δ 170.3 (C=O), 165.3 (ArC), 164.9 (ArC), 133.9 (ArC), 130.1 (ArC), 129.8 (ArC), 128.6 (ArC), 128.5 (ArC), 128.5 (ArC), 128.0 (ArC), 69.9 (C-4), 69.7 (C-2), 67.7(C-3); ESI-HRMS: m/z calcd. for $C_{18}H_{14}NaO_6$ $[M+Na]^+$ 349.0688; found, 349.0691.

2,3-Di-O-benzoyl-α/β-D-erythrofuranose (U). A stirred solution of erythrolactone 2,3-di-O-benzoate T (1.00 g, 3.06 mmol) in dry THF was cooled to −78° C. and DIBAL (1 M in hexanes, 6 mL) was added. The mixture was stirred for 4 h before it was quenched with methanol (20 mL). The so-formed residue was filtered through Celite® and the filtrate was concentrated and dissolved in EtOAc. The organic layer was washed with aqueous $NaHCO_3$ and brine. The organic layer was dried over $Na_2SO_4$ and concentrated. The residue was purified by gradient chromatography over silica gel (eluent: 10% to 25% EtOAc in hexanes) to give U (360 mg, 36%) as an α/β mixture (0.5:1) in the form of a gum; $[\alpha]_D^{25}=-29.1$ (c 0.3, DCM); $^1$H NMR (400 MHz, $CDCl_3$): δ 8.18-8.01 (m, 2H, ArH), 8.00-7.93 (m, 2H, ArH), 7.92-7.84 (m, 2H, ArH), 7.57-7.42 (m, 2H, ArH), 7.42-7.24 (m, 7H, ArH), 5.90-5.78 (m, 1.5H, H-3b, H-3α), 5.74 (dd, J=7.2, 4.7 Hz, 0.5H, H-1α), 5.72-5.67 (m, 1H, H-1β), 5.59 (dd, J=5.3, 1.6 Hz, 1H, H-2β), 5.33 (dd, J=5.9, 4.7 Hz, 0.5H, H-2β), 4.72-4.63 (m, 1H, OH), 4.58 (dd, J=10.0, 6.0 Hz, 1H, H-4β), 4.37-4.26 (m, 1H, H-4α), 4.13 (dd, J=10.0, 4.2 Hz, 1H, H-4β); $^{13}$C NMR (101 MHz, $CDCl_3$): δ 165.8 (C=O), 165.7 (C=O), 133.5 (ArC), 133.5 (ArC), 133.4 (ArC), 133.4 (ArC), 133.3 (ArC), 130.00 (ArC), 139.95 (ArC), 129.9 (ArC), 129.83 (ArC), 129.79 (ArC), 129.7 (ArC), 129.18 (ArC), 129.15 (ArC), 128.6 (ArC), 128.51 (ArC), 128.45 (ArC), 128.41 (ArC), 128.36 (ArC), 100.4 (C-1β), 94.9 (C-1α), 77.0 (C-2β), 76.9 (C-2α), 72.3 (C-3β), 72.2 (C-3α), 69.9 (C-4β), 69.8 (C-4α); ESI-HRMS: m/z calcd. for $C_{18}H_{16}NaO_6$ $[M+Na]^+$ 349.0688; found, 349.0691.

2,3-Di-O-benzoyl-β-D-erythrofuranosyl trichloroacetimidate (V). 2,3-O-Dibenzoyl-α-β-D-erythrofuranose (U) (360 mg, 1.10 mmol) and trichloroacetonitrile (2 mL) were dissolved in dry DCM (2 mL) and ice-cooled before addition of DBU (2 drops). The reaction mixture was stirred at rt for 5 min and concentrated. The crude mixture was passed through a silica gel column that had been basified with 0.5% triethylamine/hexanes, eluting with 0.5% triethylamine in EtOAc/hexanes to give compound V (458 mg, 88%) as a gum; $[\alpha]_D^{25}=-78.9$ (c 1.6, DCM); $^1$H NMR (400 MHz, $CDCl_3$): δ 8.69 (s, 1H, NH), 8.05-7.97 (m, 2H, ArH), 7.93-7.86 (m, 2H, ArH), 7.54 (m, 2H, ArH), 7.40 (m, 2H, ArH), 7.32 (m, 2H, ArH), 6.58 (s, 1H, H-1), 5.94-5.84 (m, 2H, H-2, H-3), 4.66-4.58 (m, 1H, H-4), 4.30 (dd, J=9.8, 3.4 Hz, 1H, H-4); $^{13}$C NMR (101 MHz, $CDCl_3$): δ 165.6 (ArC), 165.1 (ArC), 160.8 (C=N), 133.6 (ArC), 133.4 (ArC), 129.9 (ArC), 129.7 (ArC), 128.9 (ArC), 128.8 (ArC), 128.5 (ArC), 128.4 (ArC), 103.2 (C-1), 77.2 ($CCl_3$), 75.5 (C-2), 71.8 (C-4), 71.5 (C-3); ESI-HRMS: m/z calcd. for $C_{20}H_{16}Cl_3NaO_6$ $[M+Na]^+$ 493.9941; found, 493.9945.

5-O-β-[2''',3'''-Di-O-benzoyl-D-eryth rofu ranosyl]-6,2'',3'',6''-tetra-O-acetyl-1,3,2',4''-tetraazido-6',7'-oxazolidino-apramycin (W). Donor V (109 mg, 0.36 mmol), acceptor A (100 mg, 0.12 mmol) and activated 4 Å MS were stirred in dry DCM (2.5 mL) at rt for 1 h before cooling to −78° C. $BF_3.OEt_2$(200 μL, 0.54 mmol) was added and reaction mixture was stirred for 3 h at −78° C. The reaction was quenched at −78° C. with triethylamine (0.5 mL) and filtered through Celite® before it was diluted with EtOAc. The organic layer was washed with $NaHCO_3$ and brine then concentrated. The crude product was purified using silica gel column chromatography (eluent: 0.4%-0.8% Methanol/DCM) to give the β anomer W (68 mg, 50%) in the form of a white solid; $[\alpha]_D^{25}=+64.1$ (c 4.5, DCM); $^1$H NMR (400 MHz, $CDCl_3$): δ 7.90 (m, 4H, ArH), 7.53 (m, 2H, ArH), 7.35 (m, 4H, ArH), 5.63 (m, 2H, H-3''', H-1'''), 5.54 (d, J=3.5 Hz, 1H, H-1'), 5.51 (dd, J=5.0, 1.4 Hz, 1H, H-2'''), 5.44 (t, J=10.0 Hz, 1H, H-3''), 5.39 (d, J=3.8 Hz, 1H, H-1''), 5.02 (t, J=9.9 Hz, 1H, H-6), 4.93-4.86 (m, 2H, H-2'', H-8'), 4.82 (dd, J=7.7, 3.3 Hz, 1H, H-6'), 4.62-4.50 (m, 2H, H-5', H-4'''), 4.33 (dd, J=12.1, 1.9 Hz, 1H, H-6''), 4.23 (dd, J=12.2, 5.3 Hz, 1H, H-6''), 4.16 (dd, J=9.9, 4.9 Hz, 1H, H-4''''), 3.93 (t, J=9.2 Hz, 1H, H-5), 3.84-3.70 (m, 4H, H-4, H-4', H-5'', H-7'), 3.70-3.54 (m, 2H, H-3, H-4''), 3.49 (ddd, J=12.5, 10.5, 4.3 Hz, 1H, H-1), 3.34 (dt, J=12.9, 4.1 Hz, 1H, H-2'), 2.94 (s, 3H, $NCH_3$), 2.47 (dt, J=12.9, 4.5 Hz, 1H, H-2), 2.33-2.23 (m, 1H, H-3'), 2.11 (m, 12H, $4COCH_3$), 1.97 (q, J=11.8 Hz, 1H, H-3'), 1.65 (q, J=12.5 Hz, 1H, H-2); $^{13}$C NMR (101 MHz, $CDCl_3$): δ 170.4 (C=O), 170.2 (C=O), 169.8 (C=O), 169.6 (C=O), 165.5 (Ar—C), 165.3 (Ar—C), 157.0 (Ar—C), 133.6 (Ar—C), 133.4 (Ar—C), 129.6 (Ar—C), 129.0 (Ar—C), 128.9 (Ar—C), 128.5 (Ar—C), 128.4 (Ar—C), 106.4 (C-1'''), 97.4 (C-1'), 96.8 (C-8'), 94.1 (C-1''), 79.2 (C-5), 78.1 (C-4), 75.8 (C-2'''), 74.8 (C-6), 71.6 (C-3'''), 70.8 (C-6'), 70.6 (C-2''), 70.4 (C-4'''), 69.9 (C-3''), 69.1 (C-5''), 66.0 (C-5'), 65.6 (C-4'), 62.9 (C-6''), 60.2 (C-7'), 60.1 (C-3), 59.0 (C-4''), 58.2 (C-1), 56.5 (C-2'), 31.5 (C-2), 30.1 ($NCH_3$), 29.7(C-3') 20.9 ($2COCH_3$), 20.8 ($COCH_3$), 20.7 ($COCH_3$); ESI-HRMS: m/z calcd. for $C_{48}H_{53}N_{13}NaO_{21}6$ $[M+Na]^+$ 1170.3377; found, 1170.3353.

5-O-β-D—(Erythrofuranosyl) apramycin pentaacetate salt (DCWSU146). A stirred solution of compound W (60 mg, 0.02 mmol) in dioxane (1 mL) was treated with 3N NaOH (1 mL) and heated at 100° C. for 2 h. The reaction mixture was cooled to 55° C. and 1M $P(CH_3)_3$ in THF (0.3 mL) was added and stirring continued for 2 h. The reaction mixture was neutralized with glacial acetic acid, concentrated in vacuo, the residue dissolved in aqueous acetic acid solution (pH 4, 1 mL) and was charged to a Sephadex column (CM Sephadex C-25). The column was flushed with D.I. water (20 mL), then gradient eluted with 0.1%-1.0% $NH_4OH$ in D.I. water. The fractions containing the product were combined, acidified with glacial acetic acid, and lyophilized to afford compound DCWSU146 (35 mg, 71%) as the peracetate salt in the form of a white solid; $[\alpha]_D^{25}=+58.71$ (c 2.3, $H_2O$); $^1$H NMR (600 MHz, $D_2O$): δ 5.67 (d, J=4.1 Hz, 1H, H-1'), 5.28 (d, J=3.9 Hz, 1H, H-1''), 5.18 (d, J=3.8 Hz, 1H, H-1'''), 5.00 (d, J=8.5 Hz, 1H, H-8'), 4.38 (s, 1H, H-6'), 4.16 (q, J=4.4 Hz, 1H, H-3'''), 4.04 (dd, J=9.6, 4.9 Hz, 1H, H-4'''), 3.98 (t, J=4.2 Hz, 1H, H-2'''), 3.85 (t, J=9.7 Hz, 1H, H-4), 3.77 (dt, J=10.2, 3.9 Hz, 1H, H-5''), 3.74-3.65

(m, 3H, H-4', H-5, H-3"), 3.74-3.65 (m, 2H, H-4''', H-6"), 3.57 (dd, J=12.5, 4.5 Hz, 1H, H-6"), 3.54-3.43 (m, 4H, H-2', H-2", H-5', H-6), 3.34-3.27 (m, 1H, H-3), 3.18 (dd, J=8.5, 2.7 Hz, 1H, H-7'), 3.13 (td, J=12.0, 4.2 Hz, 1H, H-1), 3.08 (t, J=10.4 Hz, 1H, H-4"), 2.57 (s, 3H, NCH$_3$), 2.26 (dt, J=12.5, 4.1 Hz, 1H, H-2), 2.16 (dt, J=9.7, 4.4 Hz, 1H, H-3'), 1.86-1.80 (m, 1H, H-3'), 1.65 (q, J=12.6 Hz, 1H, H-2); $^{13}$C NMR (151 MHz, D$_2$O): δ 110.0 (C-1"), 94.3 (C-1'), 93.9 (C-1"), 92.7 (C-8'), 84.4 (C-5), 75.6 (C-2'''), 75.1 (C-4), 72.4 (C-6), 71.4 (C-4'''), 70.1 (C-5"), 69.6 (C-2"), 69.6 (C-4'), 69.3 (C-3"), 68.1 (C-3'''), 65.7 (C-5'), 62.5 (C-6'), 60.2 (C-6"), 59.2 (C-7'), 51.9 (C-4"), 49.4 (C-3), 48.4 (C-1), 47.4 (C-2'), 29.9 (NCH$_3$), 28.0 (C-2), 26.8 (C-3'); ESI-HRMS: m/z calcd. for C$_{25}$H$_{48}$N$_5$O$_{14}$ [M+H]$^+$ 642.3198; found, 642.3182.

Example 7

DCWSU 161, 170, 168, and 169

Figure 12:
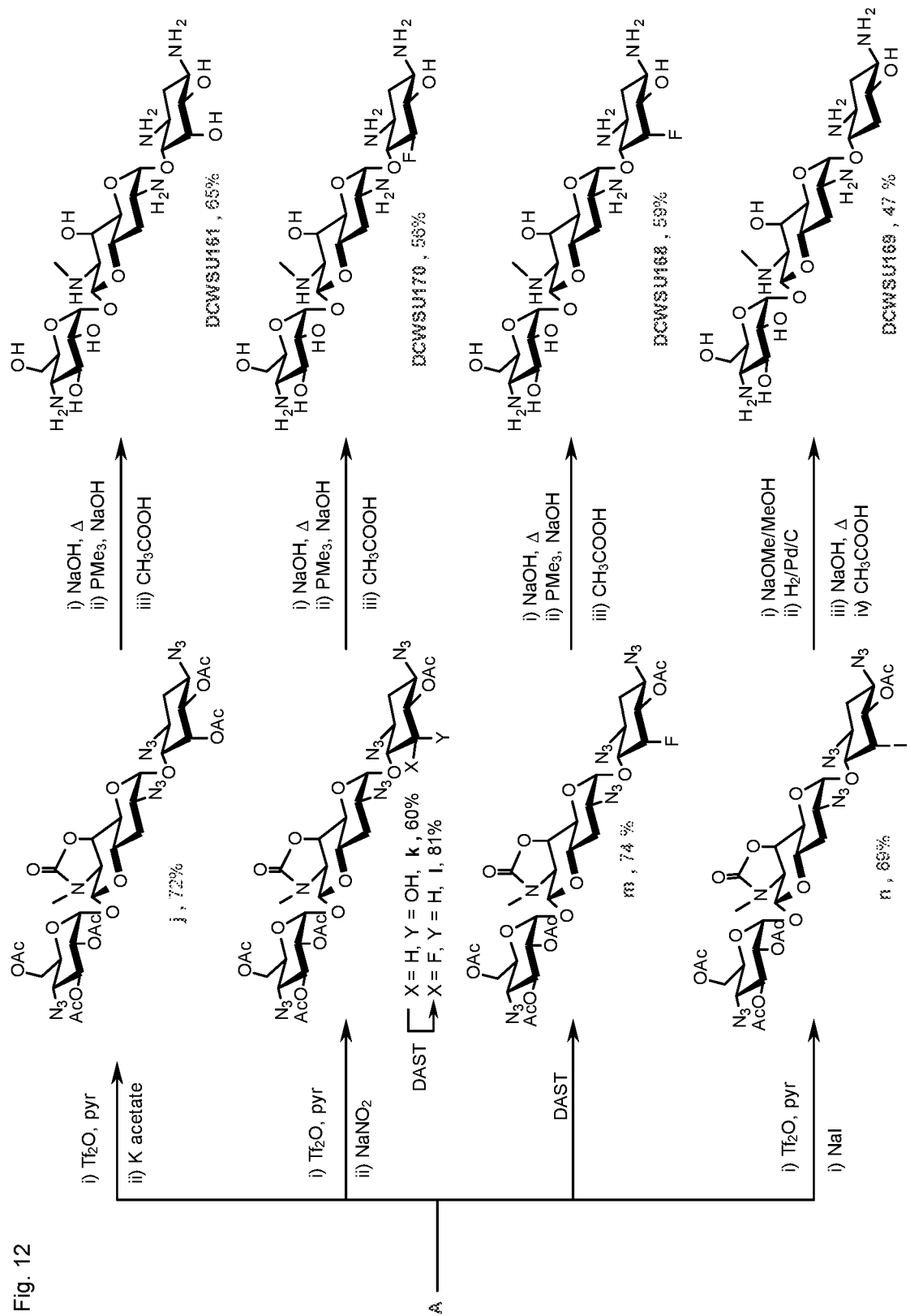
FIGS. 12 to 14 show the synthesis of exemplary compounds of the invention that are modified at position 5.
Figure 13:
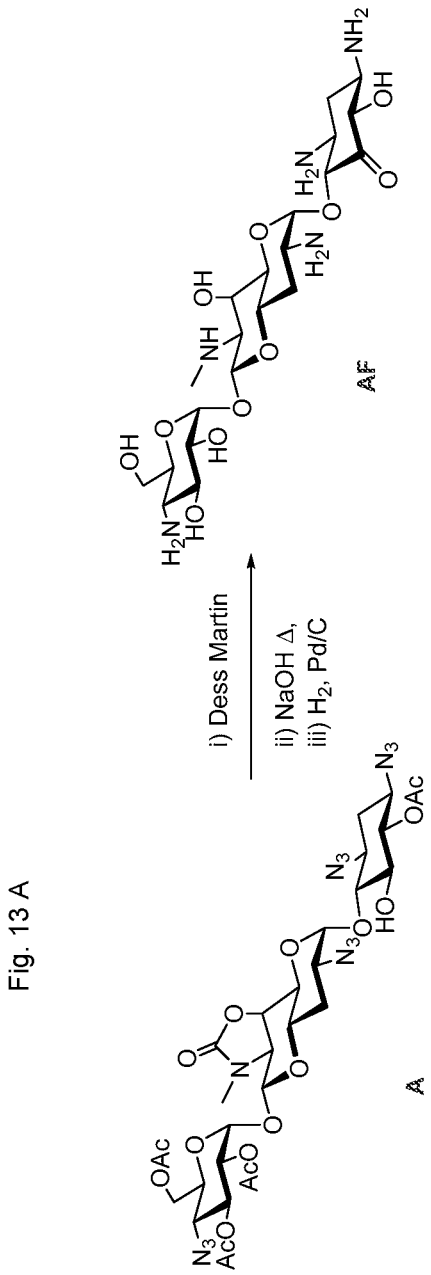
Figure 13:
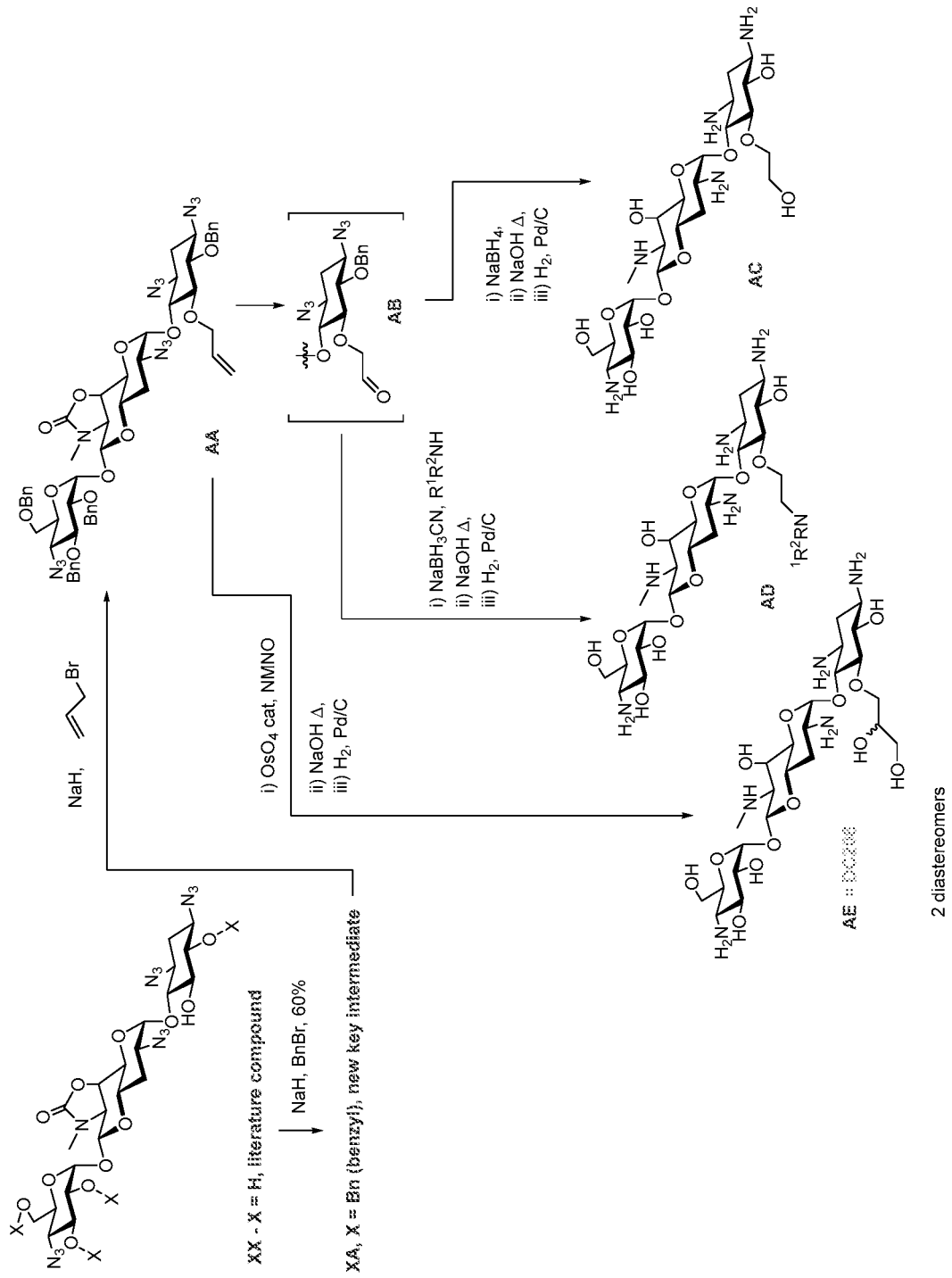
Figure 13:
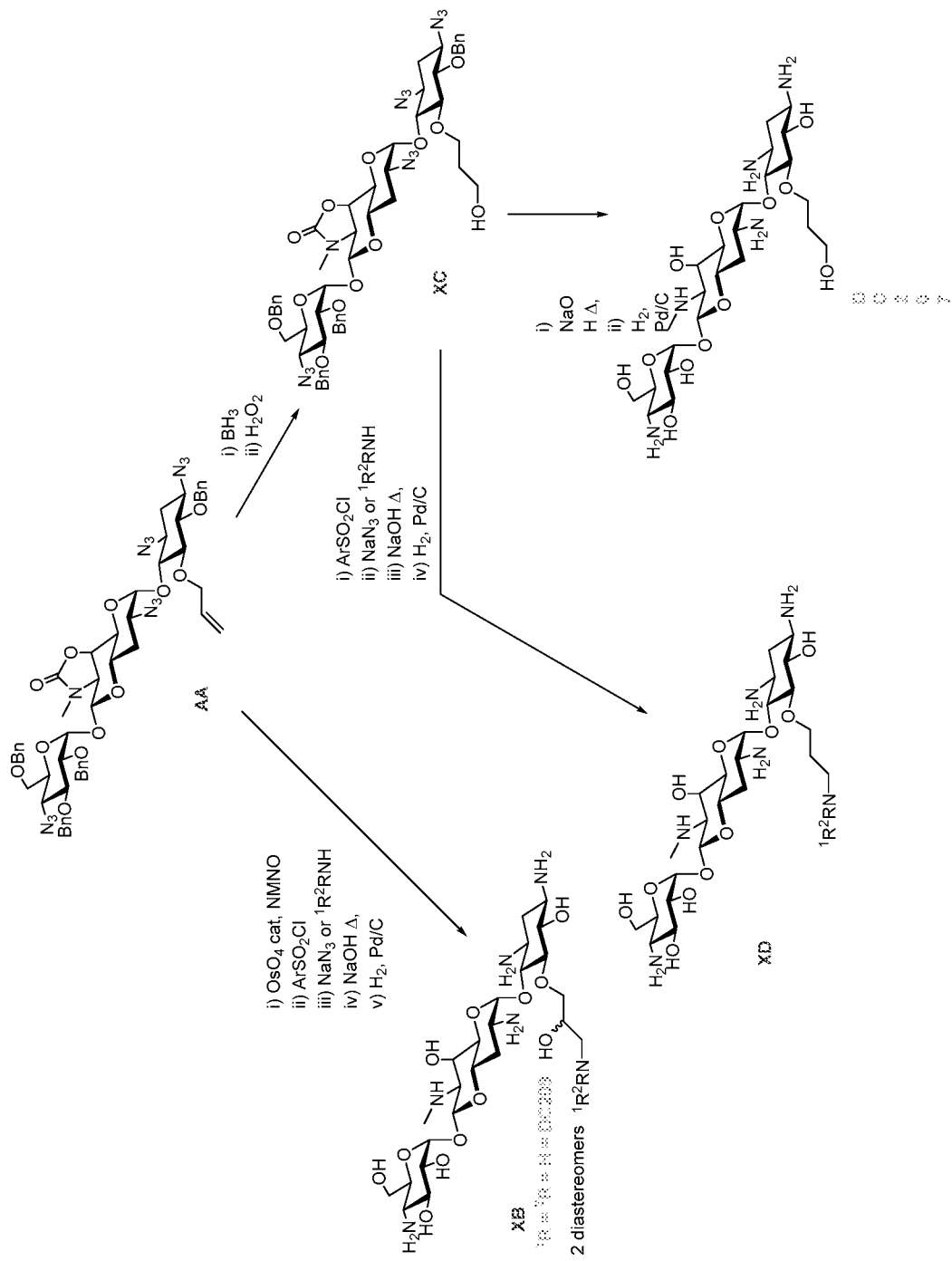
Figure 14:
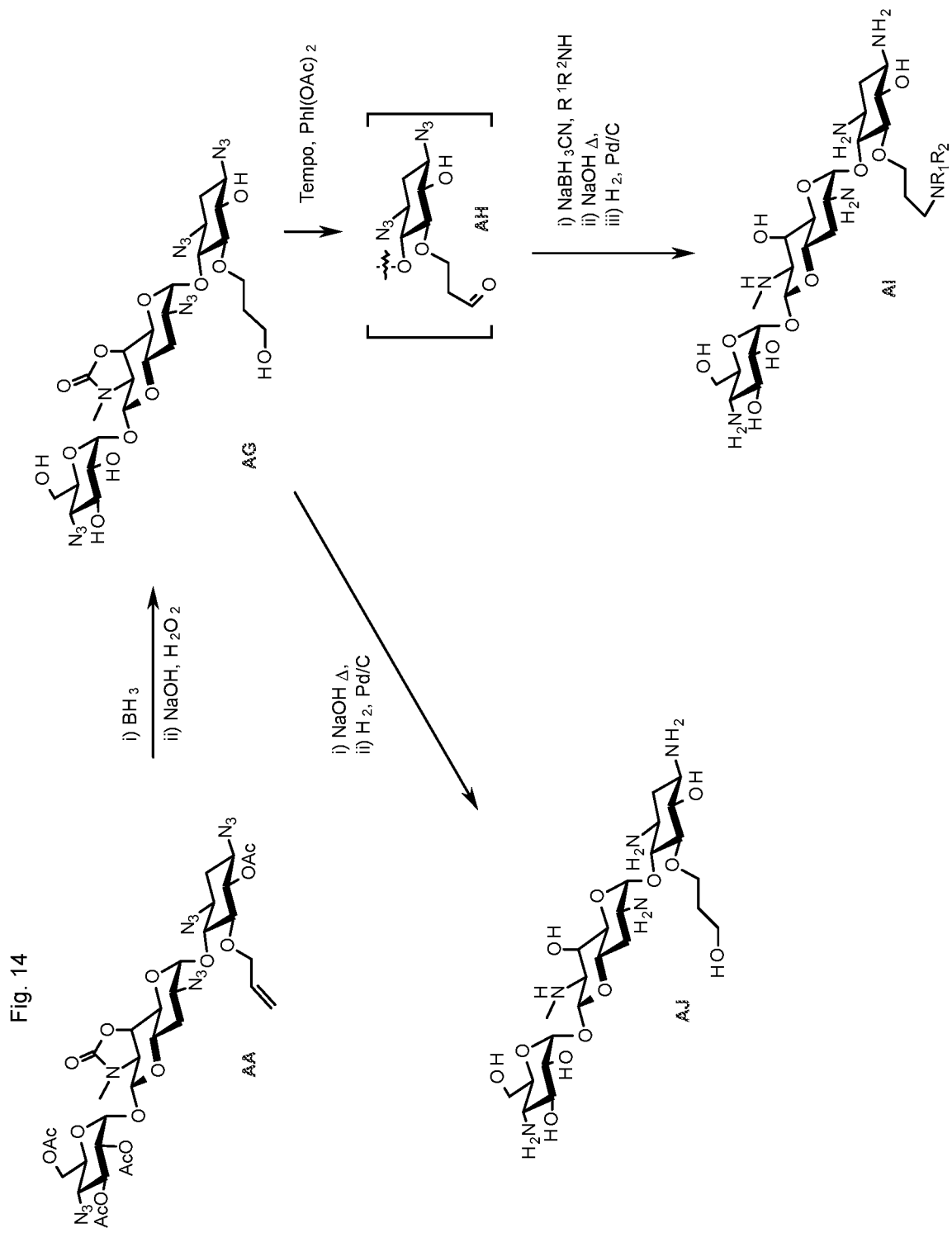
Figure 15:
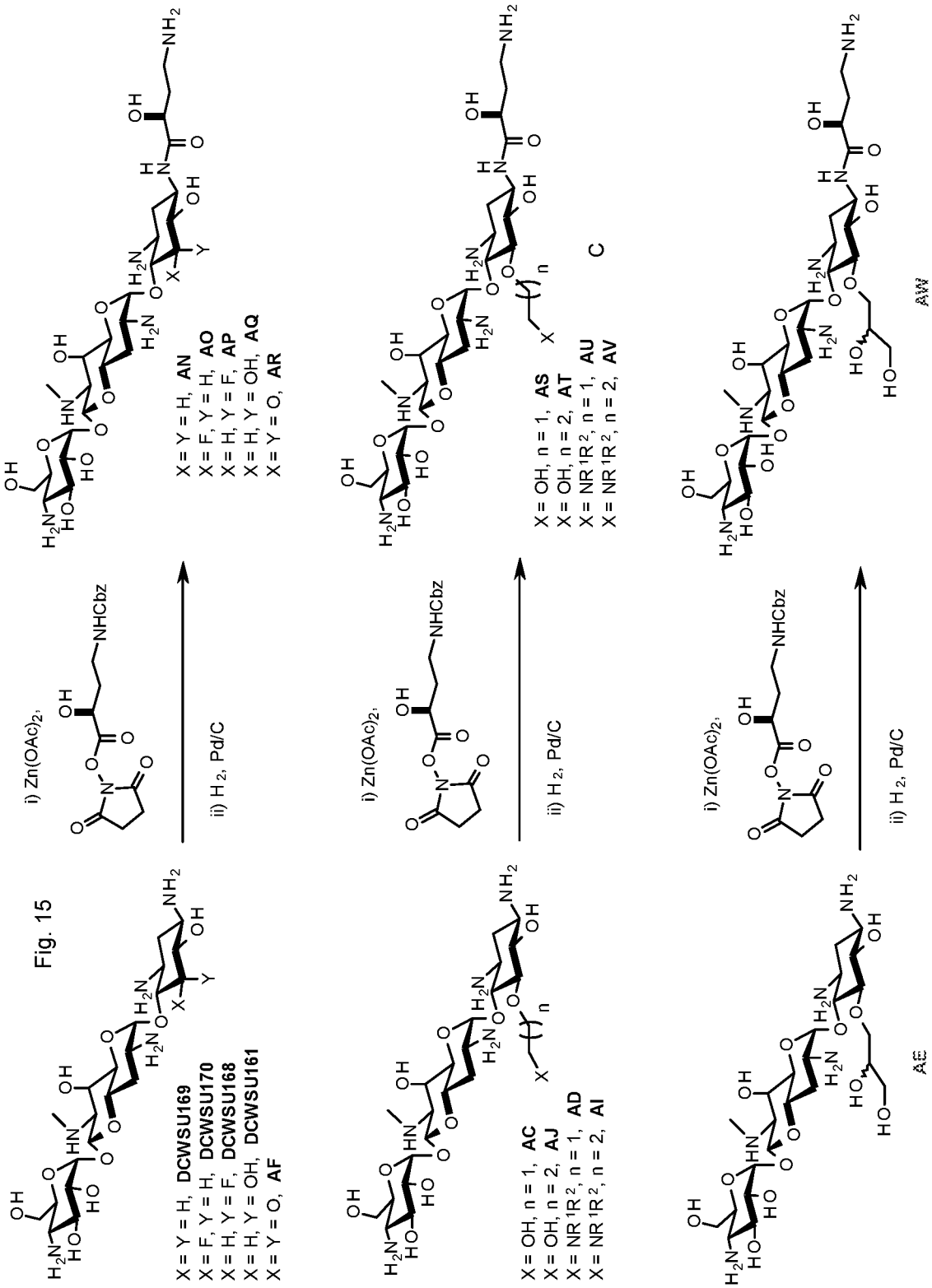
FIG. 15 shows the synthesis of exemplary compounds of the invention that are modified at position 5 and at position 1-N.

See the synthetic scheme of FIG. 12.

5,6,2",3",6"-Penta-O-acetyl-1,3,2',4"-tetraazido-5-epi-6',7'-oxazolidino-apramycin (j). To a stirred solution of compound A (100 mg, 0.12 mmol) in dry DCM (1.5 mL), pyridine (0.1 mL) was added and reaction mixture was cooled to 0° C. before triflic anhydride (40 μL, 0.24 mmol) was added. The reaction mixture was stirred for 1 h and additional triflic anhydride (40 μL, 0.24 mmol) was added. After 2 h, the reaction mixture was poured into an iced aqueous solution of NaHCO$_3$ and extracted with EtOAc. The organic layer was washed with brine and dried over Na$_2$SO$_4$ and concentrated in vacuo. The crude was dissolved in dry DMF (1 mL), treated with potassium acetate (174 mg, 1.78 mmol) and stirred at 50° C. for 1 h. After completion, the reaction was diluted with EtOAc and washed with NaHCO$_3$ and brine then concentrated. The crude was purified using silica gel column chromatography (eluent: 0.6%-1.0% methanol/DCM) to give compound j (75 mg, 72%) as a white solid; [α]$_D^{25}$=+154.25 (c 1.2, DCM); $^1$H NMR (400 MHz, CDCl$_3$): δ 5.75 (t, J=2.7 Hz, 1H, H-5), 5.51-5.38 (m, 2H, H-1", H-3"), 5.06 (d, J=3.5 Hz, 1H, H-1'), 4.87-4.68 (m, 4H, H-6, H-6', H-8', H-2'), 4.34 (dd, J=12.3, 2.2 Hz, 1H, H-6"), 4.22 (dd, J=12.2, 5.4 Hz, 1H, H-6"), 3.97 (dd, J=10.2, 3.7 Hz, 1H, H-5'), 3.91-3.83 (m, 2H, H-1, H-3), 3.80 (dd, J=10.2, 2.6 Hz, 1H, H-4), 3.78-3.71 (m, 2H, H-7', H-5"), 3.66 (td, J=10.8, 4.4 Hz, 1H, H-4'), 3.56 (t, J=10.1 Hz, 1H, H-4"), 3.20 (dt, J=12.7, 4.0 Hz, 1H, H-2'), 2.97 (s, 3H, NCH$_3$), 2.38 (dt, J=13.5, 4.7 Hz, 1H, H-2), 2.27 (dt, J=11.4, 4.4 Hz, 1H, H-3'), 2.17 (s, 3H, COCH$_3$), 2.12 (d, J=6.5 Hz, 6H, 2*COCH$_3$), 2.08-1.94 (m, 7H, H-3', 2*COCH$_3$), 1.41 (q, J=12.6 Hz, 1H, H-2); $^{13}$C NMR (101 MHz, CDCl$_3$): δ 170.4 (C=O), 170.2 (C=O), 169.7 (C=O), 169.6 (C=O), 169.5 (C=O), 156.9 (C=O), 99.9 (C-8'), 94.1 (C-1"), 93.8 (C-1'), 74.6 (C-4), 72.9 (C-6), 71.8, (C-6') 69.9 (C-3",2"), 69.4 (C-5"), 66.9 (C-5'), 66.1 (C-5), 65.9 (C-4'), 62.8 (C-6"), 60.2 (C-4"), 60.1 (C-7'), 58.0 (C-1), 56.2 (C-3), 55.5 (C-2'), 32.2 (C-2), 30.5 (NCH$_3$), 28.1 (C-3'), 20.7 (COCH$_3$), 20.6 (COCH$_3$), 20.5 (COCH$_3$); ESI-HRMS: m/z calcd. for C$_{32}$H$_{41}$N$_{13}$NaO$_{17}$ [M+H]$^+$ 902.2641; found, 902.2639.

5-Epi-apramycin pentaacetate salt (DCWSU161). A stirred solution of compound (j) (60 mg, 0.057 mmol) in dioxane (0.2 mL) was treated with 3N NaOH (0.2 mL) and heated at 100° C. for 2 h. The reaction mixture was treated with 1M P(CH$_3$)$_3$ in THF (0.15 mL) and stirred at 55° C. for 2 h. The reaction mixture was then concentrated and dissolved in aqueous acetic acid solution (pH 4, 1 mL) before it was charged to a Sephadex column (CM Sephadex C-25). The column was flushed with D.I. water (20 mL), then gradient eluted with 0.1%-1.0% NH$_4$OH in D.I. water. The fractions containing the product were combined, acidified with glacial acetic acid, and lyophilized to afford DCWSU161 (39 mg, 65%) as the peracetate salt in the form of a white solid; [α]$_D^{25}$=+90.0 (c 0.7, H$_2$O); $^1$H NMR (600 MHz, D$_2$O): δ 5.29 (d, J=4.0 Hz, 1H, H-1"), 5.21 (d, J=3.8 Hz, 1H, H-1'), 5.02 (d, J=8.5 Hz, 1H, H-8'), 4.34 (s, 1H, H-6'), 4.29 (s, 1H, H-5), 3.82-3.69 (m, 4H, H-4, H-4', H-3", H-5"), 3.65 (dd, J=12.5, 3.5 Hz, 1H, H-6"), 3.58 (dd, J=13.0, 4.5 Hz, 1H, H-6"), 3.56-3.47 (m, 4H, H-3, H-6, H-2', H-2"), 3.44 (dd, J=10.0, 2.6 Hz, 1H, H-5'), 3.34 (ddd, J=12.3, 10.6, 4.5 Hz, 1H, H-1), 3.15 (dd, J=8.5, 2.8 Hz, 1H, H-7'), 3.09 (t, J=10.4 Hz, 1H, H-4"), 2.58 (s, 3H, NCH$_3$), 2.27 (dt, J=12.5, 4.4 Hz, 1H, H-2), 2.20 (dt, J=11.4, 4.6 Hz, 1H, H-3'), 1.92-1.86 (m, 1H, H-3'), 1.55 (q, J=12.5 Hz, 1H, H-2); $^{13}$C NMR (151 MHz, D$_2$O): δ 94.3 (C-1"), 92.7 (C-8'), 89.9 (C-1'), 72.9 (C-4), 70.1 (C-6), 69.8 (C-2"), 69.4 (C-5'), 69.3 (C-5"), 68.2 (C-3"), 66.0 (C-5), 65.8 (C-4'), 62.5 (C-6'), 60.2 (C-6"), 59.4 (C-7'), 52.0 (C-4"), 48.1 (C-1), 47.4 (C-2'), 46.7 (C-3), 29.9 (NCH$_3$), 28.1 (C-2), 26.9 (C-3'); ESI-HRMS: m/z calcd. for C$_{21}$H$_{42}$N$_5$O$_{11}$ [M+H]$^+$ 540.2881; found, 540.2855.

6,2",3",6"-Tetra-O-acetyl-1,3,2',4"-tetraazido-5-epi-6',7'-oxazolidino-apramycin (k). To a stirred solution of compound A (100 mg, 0.12 mmol) in dry DCM (1.5 mL), pyridine (0.1 mL) was added and reaction mixture was cooled to 0° C. before triflic anhydride (40 μL, 0.24 mmol) was added. The reaction mixture was stirred for 1 h and additional triflic anhydride (40 μL, 0.24 mmol) was added. After 2 h, the reaction mixture was poured into an iced aqueous solution of NaHCO$_3$ and extracted with EtOAc. The organic layer was washed with brine and dried over Na$_2$SO$_4$ and concentrated in vacuo. The crude product was dissolved in dry DMF (1 mL), treated with sodium nitrite (40 mg, 0.60 mmol) and stirred at 50° C. for 1 h. After completion, the reaction was diluted with EtOAc and washed with brine then concentrated. The crude product was purified using silica gel column chromatography (eluent: 0.6%-1.0% Methanol/DCM) to give compound k (60 mg, 60%) as a white solid; [α]$_D^{25}$=+100.5 (c 0.6, DCM); $^1$H NMR (600 MHz, CDCl$_3$): δ 5.43 (t, J=10.1 Hz, 1H, H-3"), 5.39 (d, J=3.8 Hz, 1H, H-1"), 4.99 (d, J=3.5 Hz, 1H, H-1'), 4.83 (dd. J=10.4. 3.8 Hz, 1H, H-2"), 4.81-4.76 (m, 2H, H-6', H-8'), 4.64 (dd, J=10.4, 2.6 Hz, 1H, H-6), 4.39 (q, J=2.7 Hz, 1H, H-5), 4.32 (dd, J=12.2, 2.2 Hz, 1H, H-6"), 4.25-4.19 (m, 2H, H-6", H-5'), 4.01 (ddd, J=12.3, 10.4, 4.7 Hz, 1H, H-1), 3.92 (ddd, J=12.4, 9.9, 4.9 Hz, 1H, H-3), 3.77 (dd, J=7.3, 5.0 Hz, 1H, H-7'), 3.72 (ddd, J=10.6, 5.3, 2.2 Hz, 1H, H-5"), 3.67 (td, J=10.9, 4.4 Hz, 1H, H-4'), 3.61 (dd, J=9.9, 2.7 Hz, 1H, H-4), 3.57 (t, J=10.2 Hz, 1H, H-4"), 3.45 (dt, J=12.6, 4.1 Hz, 1H, H-2'), 3.13 (d, J=2.7 Hz, 1H, OH), 2.94 (s, 3H, NCH$_3$), 2.36-2.26 (m, 2H, H-2, H-3'), 2.16 (s, 3H, COCH$_3$), 2.15-2.05 (m, 6H, 2*COCH$_3$), 1.99 (dd, J=23.9, 12.0 Hz, 1H, H-3'), 1.33 (q, J=12.7 Hz, 1H, H-2); $^{13}$C NMR (151 MHz, CDCl$_3$): δ 170.4 (C=O), 170.2 (C=O), 169.7 (C=O), 157.1 (C=O), 98.0 (C-8'), 94.5 (C-1'), 94.2 (C-1"), 78.6 (C-4), 74.8 (C-6), 71.3 (C-6'), 70.1 (C-2"), 69.9 (C-3"), 69.3 (C-5"), 66.7 (C-5), 66.6 (C-5'), 65.6 (C-4'), 62.8 (C-6"), 60.2 (C-7'), 60.1 (C-4"), 57.15 (C-3), 57.07 (C-2'), 55.7 (C-1), 32.0 (C-2), 30.2 (NCH$_3$), 29.4 (C-3'), 20.9 (COCH$_3$), 20.7 (COCH$_3$), 20.7 (COCH$_3$); ESI-HRMS: m/z calcd. for C$_{30}$H$_{39}$N$_{13}$NaO$_{16}$ [M+Na]$^+$ 860.2535; found, 860.2530.

6,2",3",6"-Tetra-O-acetyl-1,3,2',4"-tetraazido-5-deoxy-5-fluoro-6', 7'-oxazolidino-apramycin (I). A stirred ice-cooled solution of compound k (36 mg, 0.04 mmol) in dry DCM (0.2 mL), was treated with diethylaminosulfur trifluoride (45

µL, 0.34 mmol) and stirred at 0° C. for 1 h and at rt for 30 min. After completion, the reaction mixture was purified by gradient chromatography over silica gel (eluent: 0.7% to 0.8% MeOH in DCM) to give I (29 mg, 81%) as a white solid; $[\alpha]_D^{25}$=+127.76 (c 1.9, DCM); $^1$H NMR (400 MHz, CDCl$_3$): δ 5.40 (t, J=10.0 Hz, 1H, H-3"), 5.35 (d, J=3.8 Hz, 1H, H-1"), 5.21-5.07 (m, 2H, H-6, H-1'), 4.96-4.86 (m, 2H, H-8', H-2"), 4.82 (dd, J=8.2, 3.4 Hz, 1H, H-6'), 4.57 (dd, J=10.4, 3.3 Hz, 1H, H-5'), 4.45 (dt, J=50.3, 9.1 Hz, 1H, H-5), 4.34 (dd, J=12.2, 2.4 Hz, 1H, H-6"), 4.23 (dd, J=12.2, 5.1 Hz, 1H, H-6"), 3.86-3.66 (m, 5H, H-3, H-4, H-4', H-7', H-5"), 3.65-3.58 (m, 1H, H-4"), 3.53 (ddd, J=12.3, 10.2, 4.4 Hz, 1H, H-1), 3.30 (dt, J=12.9, 4.1 Hz, 1H, H-2'), 2.94 (s, 3H, NCH$_3$), 2.47 (dt, J=13.2, 4.4 Hz, 1H, H-2), 2.27 (dt, J=11.4, 4.4 Hz, 1H, H-3'), 2.20-2.06 (m, 12H, 4*COCH$_3$), 1.94 (q, J=11.5 Hz, 1H, H-3'), 1.67 (q, J=12.5 Hz, 1H, H-2); $^{13}$C NMR (101 MHz, CDCl$_3$): δ 170.3 (C=O), 170.0 (C=O), 169.9 (C=O), 169.5 (C=O), 156.9 (C=O), 98.6 (C-1'), 96.1 (C-8'), 94.6 (C-1"), 93.34 (d, J=187.8 Hz, C-5), 79.78 (d, J=17.1 Hz, C-4), 73.05 (d, J=18.5 Hz, C-6), 70.6 (C-3"), 70.2 (C-2"), 70.0 (C-6'), 69.0 (C-5"), 65.8 (C-5'), 65.4 (C-4'), 62.8 (C-6"), 60.2 (C-7'), 60.1 (C-4"), 57.58 (d, J=10.6 Hz, C-3), 57.00 (d, J=9.3 Hz, C-1), 56.4 (C-2'), 31.7 (C-2), 30.0 (NCH$_3$), 29.7 (C-3'), 20.9 (COCH$_3$), 20.8 (COCH$_3$), 20.7 (COCH$_3$), 20.7 (COCH$_3$); $^{19}$F NMR (376 MHz, CDCl3): δ−196.30 (dt, J=50.4, 11.5 Hz); ESI-HRMS: m/z calcd. for C$_{30}$H$_{38}$FN$_{13}$NaO$_{15}$ [M+Na]$^+$ 862.2492; found, 862.2511.

5-Deoxy-5-fluoro apramycin pentaacetate salt (DCWSU170). A stirred solution of compound 1 (29 mg, 0.035 mmol) in dioxane (0.2 mL) was treated with 3N NaOH (0.2 mL) and heated at 100° C. for 2 h. 1M P(CH$_3$)$_3$ in THF (0.3 mL) was added and the reaction mixture was stirred at 55° C. for 2 h. The reaction mixture was then concentrated and dissolved in aqueous acetic acid solution (pH 4, 1 mL) then charged to a Sephadex column (CM Sephadex C-25). The column was flushed with D.I. water (20 mL), then gradient eluted with 0.1%-1.0% NH$_4$OH in D.I. water. The fractions containing the product were combined, acidified with glacial acetic acid, and lyophilized to afford DCWSU170 (16 mg, 56%) as the peracetate salt in the form of a white solid; $[\alpha]_D^{25}$=+89.91 (c 1.1, H$_2$O); $^1$H NMR (600 MHz, D$_2$O): δ 5.35 (d, J=3.4 Hz, 1H, H-1'), 5.28 (d, J=3.8 Hz, 1H, H-1"), 5.00 (d, J=8.5 Hz, 1H, H-8'), 4.43 (dt, J=50.8, 9.0 Hz, 1H, H-5), 4.35 (s, 1H, H-6'), 4.04 (q, J=9.6 Hz, 1H, H-4), 3.79-3.69 (m, 4H, H-6, H-4', H-3", H-5"), 3.63 (dd, J=12.3, 2.9 Hz, 1H, H-6"), 3.56 (dd, J=12.5, 4.5 Hz, 1H, H-6"), 3.52 (d, J=10.3 Hz, 1H, H-5'), 3.49 (dd, J=9.8, 3.9 Hz, 1H, H-2"), 3.44 (dt, J=12.3, 3.9 Hz, 1H, H-2'), 3.34 (td, J=11.7, 10.9, 4.0 Hz, 1H, H-3), 3.21-3.14 (m, 2H, H-1, H-7'), 3.07 (t, J=10.4 Hz, 1H, H-4"), 2.57 (s, 3H, NCH$_3$), 2.29 (dt, J=12.8, 4.3 Hz, 1H, H-2), 2.15 (dt, J=10.1, 4.5 Hz, 1H, H-3'), 1.87-1.83 (m, 1H, H-3'), 1.73-1.66 (m, 1H, H-2); $^{13}$C NMR (151 MHz, D$_2$O): δ 95.33 (d, J=190.2 Hz, C-5), 94.8 (C-1'), 94.3 (C-1"), 92.7 (C-8'), 75.72 (d, J=16.8 Hz, C-4), 70.27 (d, J=20.5 Hz, C-6), 70.2 (C-2"), 69.5 (C-5'), 69.3 (C-5"), 68.2 (C-3"), 65.8 (C-4'), 62.6 (C-6'), 60.2 (C-6"), 59.3 (C-7'), 52.0 (C-4"), 48.67 (d, J=11.5 Hz, C-1), 47.6 (C-2'), 47.34 (d, J=11.3 Hz, C-3), 29.9 (NCH$_3$), 28.0 (C-2), 26.6 (C-3'). $^{19}$F NMR (376 MHz, D$_2$O): δ −195.08 (dt, J=50.9, 11.7 Hz); ESI-HRMS: m/z calcd. for C$_{21}$H$_{41}$FN$_5$O$_{10}$ [M+H]$^+$ 542.2837; found, 542.2838.

6,2",3",6"-Tetra-O-acetyl-1,3,2',4"-tetraazido-5-deoxy-5-epifluoro-6',7'-oxazolidino-apramycin (m). To a stirred ice-cooled solution of compound 124 (50 mg, 0.06 mmol) in dry DCM (0.2 mL), diethylaminosulfur trifluoride (65 µl, 0.48 mmol) was added, and the reaction mixture was stirred at rt for 3 h. After completion, the reaction mixture was purified by gradient chromatography over silica gel (eluent: 0.7% to 0.8% MeOH in DCM) to give m (37 mg, 74%) as a white solid; $[\alpha]_D^{25}$=+104.39 (c 2.5, DCM); $^1$H NMR (600 MHz, CDCl$_3$): δ 5.42 (t, J=10.0 Hz, 1H, H-3"), 5.38 (d, J=3.8 Hz, 1H, H-1"), 5.09-4.96 (m, 2H, H-5, H-1'), 4.90-4.84 (m, 2H, H-8', H-2"), 4.80 (dd, J=7.7, 3.5 Hz, 1H, H-6'), 4.70 (ddd, J=27.3, 10.5, 1.8 Hz, 1H, H-6), 4.35 (dd, J=10.4, 3.4 Hz, 1H, H-5'), 4.32 (dd, J=12.2, 2.2 Hz, 1H, H-6"), 4.21 (dd, J=12.2, 5.3 Hz, 1H, H-6"), 4.02-3.92 (m, 2H, H-1, H-3), 3.80 (dd, J=7.6, 4.3 Hz, 1H, H-7'), 3.78-3.69 (m, 2H, H-4', H-5"), 3.67-3.55 (m, 2H, H-4, H-4"), 3.34 (dt, J=12.8, 4.0 Hz, 1H, H-2'), 2.94 (s, 3H, NCH$_3$), 2.45 (dt, J=13.5, 4.9 Hz, 1H, H-2), 2.29 (dt, J=11.3, 4.4 Hz, 1H, H-3'), 2.17 (s, 3H, COCH$_3$), 2.10 (d, J=10.8 Hz, 6H, 2*COCH$_3$), 2.06 (s, 3H, COCH$_3$), 2.01-1.94 (m, 1H, H-3'), 1.42 (q, J=12.7 Hz, 1H, H-2); $^{13}$C NMR (151 MHz, CDCl$_3$): δ 170.4 (C=O), 169.9 (C=O), 169.7 (C=O), 156.9 (C=O), 96.7 (C-8'), 96.2 (C-1'), 94.1 (C-1"), 87.65 (d, J=184.1 Hz, C-5), 77.55 (d, J=17.9 Hz, C-4), 73.45 (d, J=17.1 Hz, C-6), 70.6 (C-6'), 70.3 (C-3"), 69.8 (C-2"), 69.1 (C-5"), 66.4 (C-5'), 65.5 (C-4'), 62.9 (C-6"), 60.2 (C-4"), 60.0 (C-7'), 57.03 (d, J=3.8 Hz, C-3), 56.0 (C-2'), 55.76 (d, J=4.1 Hz, C-1), 32.0 (C-2), 30.1 (NCH$_3$), 29.2 (C-3'), 20.7 (COCH$_3$), 20.7 (COCH$_3$), 20.7 (COCH$_3$); $^{19}$F NMR (376 MHz, CDCl$_3$): δ −213.48 (dt, J=52.6, 26.8 Hz); ESI-HRMS: m/z calcd. for C$_{30}$H$_{38}$FN$_{13}$NaO$_{15}$ [M+Na]$^+$ 862.2492; found, 862.2502.

5-Deoxy-5-epi-fluoro apramycin pentaacetate salt (DCWSU168). A stirred solution of compound m (37 mg, 0.044 mmol) in dioxane (0.2 mL) was treated with 3 N NaOH (0.2 mL) and heated at 100° C. for 2 h. 1 M P(CH$_3$)$_3$ in THF (0.3 mL) was added and the reaction mixture stirred at 55° C. for 2h. The reaction mixture was then concentrated and dissolved in aqueous acetic acid solution (pH 4, 1 mL) before it was charged to a Sephadex column (CM Sephadex C-25). The column was flushed with D.I. water (20 mL), then gradient eluted with 0.1%-1.0% NH$_4$OH in D.I. water. The fractions containing the product were combined, acidified with glacial acetic acid, and lyophilized to afford DCWSU168 (22 mg, 59%) as the peracetate salt in the form of a white solid; $[\alpha]_D^{25}$=+152.0 (c 0.1, H$_2$O); $^1$H NMR (600 MHz, D$_2$O): δ 5.25 (d, J=3.9 Hz, 1H, H-1"), 5.24 (d, J=3.8 Hz, 1H, H-1'), 5.13 (d, J=51.7 Hz, 1H, H-5), 4.98 (d, J=8.5 Hz, 1H, H-8'), 4.31 (s, 1H, H-6'), 3.94 (dd, J=26.1, 10.7 Hz, 1H, H-4), 3.78-3.63 (m, 4H, H-6, H-4', H-3", H-5"), 3.61 (dd, J=12.5, 3.5 Hz, 1H, H-6"), 3.57-3.50 (m, 2H, H-3, H-6"), 3.49-3.44 (m, 2H, H-2', H-2"), 3.42 (dd, J=10.1, 2.6 Hz, 1H, H-5'), 3.33 (td, J=11.7, 4.3 Hz, 1H, H-1), 3.12 (dd, J=8.5, 2.8 Hz, 1H, H-7'), 3.05 (t, J=10.4 Hz, 1H, H-4"), 2.54 (s, 3H, NCH$_3$), 2.29 (dt, J=12.6, 4.4 Hz, 1H, H-2), 2.19-2.10 (m, 1H, H-3'), 1.90-1.82 (m, 1H, H-3'), 1.59 (q, J=12.6 Hz, 1H, H-2); $^{13}$C NMR (151 MHz, D$_2$O): δ 94.3 (C-1"), 92.7 (C-8'), 90.3 (C-1'), 87.37 (d, J=181.7 Hz, C-5), 72.01 (d, J=17.8 Hz, C-4), 70.1 (C-2"), 69.5 (C-5'), 69.2 (C-5"), 68.55 (d, J=17.2 Hz, C-6), 68.1 (C-3"), 65.7 (C-4'), 62.5 (C-6'), 60.2 (C-6"), 59.3 (C-7'), 52.0 (C-4"), 48.09 (d, J=4.4 Hz, C-1), 47.3 (C-2'), 46.61 (d, J=4.2 Hz, C-3), 29.9 (NCH$_3$), 27.9 (C-2), 26.7 (C-3'); $^{19}$F NMR (376 MHz, D$_2$O): δ −217.88 (dt, J=51.8, 27.2 Hz); ESI-HRMS: m/z calcd. for C$_{21}$H$_{41}$FN$_5$O$_{10}$ [M+H]$^+$ 542.2837; found, 542.2825.

6,2",3",6"-Tetra-O-acetyl-1,3,2',4"-tetraazido-5-deoxy-5-epiiodo-6',7'-oxazolidino-apramycin (n). To a stirred solution of compound A (100 mg, 0.12 mmol) in dry DCM (1.5 mL), pyridine (0.1 mL) was added and reaction mixture was cooled to 0° C. before triflic anhydride (40 µL, 0.24 mmol) was added. The reaction mixture was stirred for 1 h and additional triflic anhydride (40 µL, 0.24 mmol) was added.

After 2 h, the reaction mixture was poured into an iced aqueous solution of NaHCO$_3$ and extracted with EtOAc. The organic layer was washed with brine and dried over Na$_2$SO$_4$ and concentrated in vacuo. The crude product was dissolved in dry acetone (25 mL), heated to reflux under stirring with sodium iodide (266 mg, 1.78 mmol) for 12 h. After completion, the reaction mixture was concentrated, diluted with EtOAc and washed with brine then concentrated. The crude product was purified using silica gel column chromatography (eluent: 0.6%-1.0% Methanol/DCM) to give compound n (93 mg, 89%) as a white solid; $[\alpha]_D^{25}$=+172.23 (c 6.2, DCM); $^1$H NMR (600 MHz, CDCl$_3$): δ 5.46-5.38 (m, 2H, H-1", H-3"), 4.92 (d, J=3.4 Hz, 1H, H-1'), 4.84 (t, J=3.2 Hz, 1H, H-5), 4.80-4.72 (m, 3H, H-6', H-8', H-2"), 4.31 (dd, J=12.3. 2.2 Hz. 1H. H-6"), 4.20 (dd, J=12.2, 5.4 Hz, 1H, H-6"), 4.04-3.98 (m, 2H, H-3, H-4), 3.98-3.90 (m, 2H, H-1, H-5'), 3.80-3.70 (m, 2H, H-7', H-5"), 3.66 (td, J=10.8, 4.5 Hz, 1H, H-4'), 3.55 (t, J=10.2 Hz, 1H, H-4"), 3.25 (dt, J=12.8, 3.9 Hz, 1H, H-2'), 3.06 (dd, J=9.7, 3.6 Hz, 1H, H-6), 2.94 (s, 3H, NCH$_3$), 2.28 (ddt, J=12.6, 8.7, 4.6 Hz, 2H, H-2, H-3'), 2.15 (s, 3H, COCH$_3$), 2.13-2.03 (m, 7H, H-3', 2*COCH$_3$), 2.01 (s, 3H, COCH$_3$), 1.41-1.29 (m, 1H, H-2); $^{13}$C NMR (151 MHz, CDCl$_3$): δ 170.4 (C=O), 170.2 (C=O), 169.6 (C=O), 169.6 (C=O), 156.8 (C=O), 99.8 (C-8'), 94.3 (C-1"), 93.9 (C-1'), 74.1 (C-6), 72.6 (C-4), 71.7 (C-6'), 69.9 (C-2"), 69.8 (C-3"), 69.4 (C-5"), 67.2 (C-5'), 65.8 (C-4'), 62.8 (C-6"), 60.6 (C-1), 60.2 (C-4"), 60.1 (C-7'), 59.2 (C-3), 55.4 (C-2'), 32.8 (C-5), 32.6 (C-2), 30.4 (NCH$_3$), 28.0 (C-3'), 20.9 (COCH$_3$), 20.8 (COCH$_3$), 20.7 (COCH$_3$), 20.7 (COCH$_3$); ESI-HRMS: m/z calcd. for C$_{30}$H$_{36}$IN$_{13}$NaO$_{15}$ [M+Na]$^+$ 970.1553; found, 970.1571.

5-Deoxy-apramycin pentaacetate salt (DCWSU169). To a solution of compound n (45 mg, 0.05 mmol) in dry methanol (5 mL), sodium methoxide (10 mg, 0.06 mmol) was added and the reaction mixture was stirred for 30 min. The reaction was quenched with Amberlyst®, filtered and the solvent was evaporated in vacuo. The crude product was dissolved in dioxane:water:glacial acetic acid=1:2:0.2 (0.3 mL) and 10% Pd/C (60 mg, 1.1 equiv.) was added. The reaction was stirred at room temperature under 1 atm of hydrogen (balloon) for 12 h. After completion, the reaction mixture was filtered over Celite® and filtrate concentrated to dryness. The residue was dissolved in dioxane (0.5 mL) and treated with 3N NaOH (0.25 mL) and heated at 100° C. for 30 min. The reaction mixture was cooled to rt and neutralized with glacial acetic acid before concentration in vacuo. The crude product was dissolved in aqueous acetic acid solution (pH 4, 1 mL) before it was charged to a Sephadex column (CM Sephadex C-25). The column was flushed with D.I. water (20 mL), then gradient eluted with 0.1%-1.0% NH$_4$OH in D.I. water. The fractions containing the product were combined, acidified with glacial acetic acid and lyophilized to afford the peracetate salt of DCWSU169 (18.5 mg, 47%) as a white solid; $[\alpha]_D^{25}$=+105.0 (c 0.2, H$_2$O); 1H NMR (600 MHz, D$_2$O): δ 5.35 (d, J=4.0 Hz, 1H, H-1"), 5.23 (d, J=3.8 Hz, 1H, H-1'), 5.07 (d, J=8.5 Hz, 1H, H-8'), 4.40 (s, 1H, H-6'), 3.87-3.73 (m, 4H, H-4, H-4', H-3", H-5"), 3.70 (dd, J=12.5, 3.3 Hz, 1H, H-6"), 3.63 (dd, J=12.5, 4.7 Hz, 1H, H-6"), 3.62-3.52 (m, 2H, H-6, H-2"), 3.52 (dt, J=12.8, 4.3 Hz, 1H, H-2'), 3.48 (dd, J=10.0, 3.0 Hz, 1H, H-5'), 3.34 (ddd, J=12.4, 10.1, 4.1 Hz, 1H, H-3), 3.21 (dd, J=8.5, 2.9 Hz, 1H, H-7'), 3.17-3.10 (m, 2H, H-1, H-4"), 2.63 (s, 3H, NCH$_3$), 2.55 (dt, J=12.2, 4.3 Hz, 1H, H-5), 2.33 (dt, J=12.6, 4.3 Hz, 1H, H-2), 2.23 (dt, J=10.8, 4.5 Hz, 1H, H-3'), 1.90 (q, J=11.8, 11.0 Hz, 1H, H-3'), 1.61 (q, J=12.5 Hz, 1H, H-2), 1.34 (q, J=11.7 Hz, 1H, H-5); $^{13}$C NMR (151 MHz, D$_2$O): δ 94.3 (C-1"), 92.7 (C-8'), 90.1 (C-1'), 70.8 (C-4), 70.2 (C-6), 69.4 (C-2"), 69.3 (C-5'), 68.2 (C-5"), 67.2 (C-3"), 65.8 (C-4'), 62.6 (C-6'), 60.2 (C-6"), 59.4 (C-7'), 52.5 (C-1), 52.0 (C-4"), 50.8 (C-3), 47.3 (C-2'), 33.8 (C-5), 30.0 (NCH$_3$), 28.5 (C-2), 26.9 (C-3'); ESI-HRMS: m/z calcd. for C$_{21}$H$_{42}$N$_5$O$_{10}$ [M+H]$^+$ 524.2932; found, 524.2924.

Example 8

DCWSU 164 and 167

Figure 16:
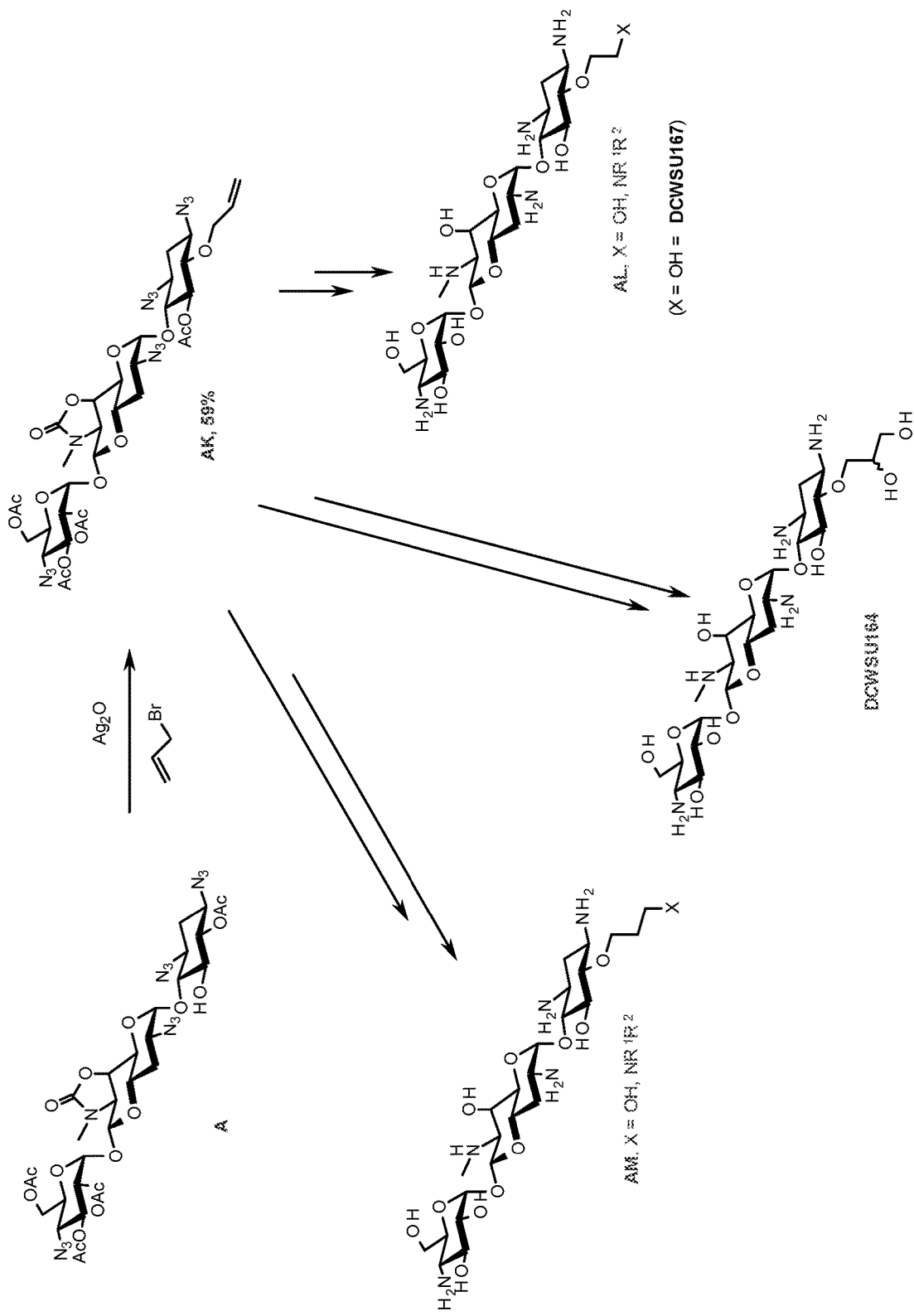
FIG. 16 shows the synthesis of exemplary compounds of the invention that are modified at position 6.

See the synthetic scheme of FIG. 16.

Note intermediates AK-1 and AK-2 are not drawn in the scheme for these two compounds 5,2",3",6"-Tetra-O-acetyl-6-O-allyl-1,3,2',4"-tetraazido-6',7'-oxazolidino-apramycin (AK). 6,2",3",6"-Tetra-O-acetyl-1,3,2',4"-tetraazido-6',7'-oxazolidino-apramycin A (100 mg, 0.12 mmol) was dissolved in dry DCM (0.5 mL) and treated with allyl bromide (0.5 mL, 5.9 mmol) and silver oxide (400 mg, 1.7 mmol). The reaction mixture was covered with aluminium foil and stirred at rt for 12 h. After completion, the reaction was filtered through Celite® and concentrated to dryness. The crude product was purified by column chromatography (eluent: 5% to 30% EtOAc/hexanes) to give AK (60 mg, 59%) as a white solid; $[\alpha]_D^{25}$=+60.0 (c 0.2, DCM); $^1$H NMR (400 MHz, CDCl$_3$): δ 5.86 (ddt, J=16.3, 10.3, 5.9 Hz, 1H, CH$_2$CHCH$_2$O), 5.45-5.34 (m, 1H, H-3"), 5.32 (d, J=3.8 Hz, 1H, H-1"), 5.25 (dd, J=17.2, 1.5 Hz, 1H, CH$_2$CHCH$_2$O), 5.22-5.16 (m, 1H, CH$_2$CHCH$_2$O), 5.05 (t, J=9.9 Hz, 1H, H-5), 4.99-4.90 (m, 2H, H-8', H-2"), 4.87 (d, J=3.6 Hz, 1H, H-1'), 4.81 (dd, J=8.6, 3.2 Hz, 1H, H-6'), 4.74 (dd, J=10.5, 3.2 Hz, 1H, H-5'), 4.36-4.17 (m, 3H, H-6", CH$_2$CHCH$_2$O), 4.09 (dd, J=12.2, 6.1 Hz, 1H, CH$_2$CHCH$_2$O), 3.92-3.82 (m, 2H, H-4', H-7'), 3.82-3.76 (m, 1H, H-3), 3.76-3.67 (m, 1H, H-5"), 3.66-3.52 (m, 2H, H-1, H-4"), 3.48 (t, J=9.9 Hz, 1H, H-4), 3.39 (dt, J=12.7, 4.1 Hz, 1H, H-2'), 3.19 (t, J=9.8 Hz, 1H, H-6), 2.92 (s, 3H, NCH$_3$), 2.46 (dt, J=13.1, 4.6 Hz, 1H, H-2), 2.26 (dt, J=10.7, 4.1 Hz, 1H, H-3'), 2.21-2.02 (m, 12H, 4*COCH$_3$), 1.85 (q, J=11.4 Hz, 1H, H-3'), 1.49 (q, J=12.5 Hz, 1H, H-2); $^{13}$C NMR (101 MHz, CDCl$_3$): δ 170.3 (C=O), 170.3 (C=O), 170.0 (C=O), 169.4 (C=O), 156.9 (C=O), 133.6 (CH$_2$CHCH$_2$O), 118.1 (CH$_2$CHCH$_2$O), 99.1 (C-1'), 94.2 (C-8', C-1"), 81.9 (C-6), 80.3 (C-4), 74.3 (CH$_2$CHCH$_2$O), 74.0 (C-5), 70.7 (C-3"), 69.9 (C-2"), 69.7 (C-6'), 68.8 (C-5"), 65.4 (C-5'), 65.2 (C-4'), 62.9 (C-6"), 60.2 (C-4"), 60.0 (C-7'), 59.7 (C-1), 58.4 (C-3), 56.6 (C-2'), 32.1 (C-2), 30.0 (NCH$_3$), 29.8 (C-3'), 21.1 (COCH$_3$), 21.0 (COCH$_3$), 20.8 (COCH$_3$), 20.7 (COCH$_3$); ESI-HRMS: m/z calcd. for C$_{33}$H$_{43}$N$_{13}$NaO$_{16}$ [M+Na]$^+$ 900.2848; found, 900.2841.

5,2",3",6"-Tetra-O-acetyl-1,3,2',4"-tetraazido-6-O—(2,3-dihydroxypropyl)-6',7'-oxazolidino-apramycin (AK-1). A stirred solution of compound AK (20 mg, 0.02 mmol) in THF (0.4 mL) and water (0.1 mL) was treated with N-methylmorpholine-N-oxide (8 mg, 0.07 mmol) and 2.5% OsO$_4$ in tert-butanol (60 μL mg, 0.005 mmol). The reaction mixture was stirred at rt for 4 h. After completion, the reaction mixture was diluted with EtOAc and the organic layer was washed with aqueous NaHCO$_3$ followed by brine, dried with Na$_2$SO$_4$, and concentrated. The crude product was purified via silica gel chromatography eluting with 0.7% to 3% methanol in DCM to give AK-1 (15 mg, 71%) as a white solid; $[\alpha]_D^{25}$=+63.75 (c 1.3, DCM); $^1$H NMR (400 MHz, CDCl$_3$): δ 5.38 (t, J=9.9 Hz, 1H, H-3'), 5.32 (d, J=3.8 Hz, 1H, H-1"), 5.08-5.01 (m, 1H, H-5), 4.98-4.91 (m, 2H, H-8', H-2"), 4.88 (d, J=3.0 Hz, 1H, H-1'), 4.80 (dd, J=8.6, 3.1 Hz, 1H H-6'), 4.71 (dd, J=10.5, 3.1 Hz, 1H, H-5'), 4.36-4.27 (m, 1H, H-6''), 4.22 (dd, J=12.2, 5.0 Hz, 1H, H-6''), 3.90-3.68 (m, 6H, H-3, H-4', H-7', H-5'', $CH_2OHCHOHCH_2O$, $CH_2OHCHOHCH_2O$), 3.66-3.43 (m, 6H, H-1, H-4, H-4'', $CH_2OHCHOHCH_2O$, $CH_2OHCHOHCH_2O$), 3.37 (dt, J=12.6, 3.6 Hz, 1H, H-2'), 3.19 (t, J=9.8 Hz, 1H, H-6), 2.91 (s, 3H, $NCH_3$), 2.48 (dt, J=12.7, 4.2 Hz, 1H, H-2), 2.29-2.23 (m, 1H, H-3'), 2.17-2.07 (m, 12H, 4*$COCH_3$), 1.90-1.80 (m, 1H, H-3'), 1.59-1.46 (m, 1H, H-2); $^{13}C$ NMR (101 MHz, $CDCl_3$): δ 170.4 (C=O), 170.2 (C=O), 170.0 (C=O), 157.0 (C=O), 99.1 (C-1'), 94.5 (C-8'), 94.3 (C-1''), 82.9 (C-6), 80.0 (C-4), 74.8 (C-5), 74.4 ($CH_2OHCHOHCH_2O$), 70.7 (C-3''), 70.6 (C-2''), 69.9 ($CH_2OHCHOHCH_2O$), 69.7 (C-6'), 68.8 (C-5''), 65.4 (C-5'), 65.2 (C-4'), 63.1 ($CH_2OHCHOHCH_2O$), 62.9 (C-6''), 60.1 (C-4''), 60.0 (C-7'), 59.6 (C-1), 58.2 (C-3), 56.4 (C-2'), 31.8 (C-2), 29.9 ($NCH_3$), 29.8 (C-3'), 21.1 ($COCH_3$), 20.9 ($COCH_3$), 20.9 ($COCH_3$), 20.7 ($COCH_3$); ESI-HRMS: m/z calcd. for $C_{33}H_{45}N_{13}NaO_{18}$ [M+Na]$^+$ 934.2903; found, 934.2905.

6-O—(2,3-Dihydroxypropyl)-apramycin pentaacetate salt (DCWSU164). A stirred solution of compound AK-1 (14 mg, 0.015 mmol) in dioxane (0.2 mL) was treated with 3N NaOH (0.2 mL) and heated at 100° C. for 2 h. 1M $P(CH_3)_3$ in THF (0.15 mL) was added and the reaction mixture was stirred at 55° C. for 2 h. The reaction mixture was cooled to 0° C., neutralized with glacial acetic acid and concentrated. The crude product was dissolved in aqueous acetic acid solution (pH 4, 1 mL) then charged to a Sephadex column (CM Sephadex C-25). The column was flushed with D.I. water (20 mL), then gradient eluted with 0.1%-1.0% $NH_4OH$ in D.I. water. The fractions containing the product were combined, acidified with glacial acetic acid, and lyophilized to afford DCWSU164 (5.5 mg, 39%) as the peracetate salt in the form of a white solid; $[\alpha]_D^{25}$=+100.96 (c 0.2, $H_2O$); $^1H$ NMR (600 MHz, $D_2O$): δ 5.51 (s, 1H, H-1'), 5.28 (d, J=4.0 Hz, 1H, H-1''), 5.00 (dd, J=8.4, 1.5 Hz, 1H, H-8'), 4.35 (s, 1H, H-6'), 3.86-3.66 (m, 6H, H-4, H-4', H-3'', H-5'', $CH_2OHCHOHCH_2O$, $CH_2OHCHOHCH_2O$), 3.66-3.52 (m, 5H, H-5, H-5', H-6'', $CH_2OHCHOHCH_2O$), 3.50 (dd, J=9.3, 3.9 Hz, 1 H, H-2''), 3.48-3.34 (m, 4H, H-2', $CH_2OHCHOHCH_2O$), 3.32-3.22 (m, 2H, H-3, H-6), 3.23-3.14 (m, 2H, H-1, H-7'), 3.08 (t, J=10.2 Hz, 1H, H-4''), 2.57 (s, 3H, $NCH_3$), 2.31-2.23 (m, 1H, H-2), 2.19-2.10 (m, 1H, H-3'), 1.66 (q, J=12.6 Hz, 1H, H-2); $^{13}C$ NMR (151 MHz, $D_2O$) δ 95.4 (C-1'), 94.3 (C-1''), 92.7 (C-8'), 81.3 (C-6), 77.7 (C-4), 75.2 (C-5), 73.7 ($CH_2OHCHOHCH_2O$), 70.3 ($CH_2OHCHOHCH_2O$), 70.1 (C-2''), 69.6 (C-5'), 69.2 (C-5''), 68.2 (C-3''), 65.9 (C-4'), 62.6 (C-6'), 62.1 ($CH_2OHCHOHCH_2O$), 60.2 (C-6''), 59.3 (C-7'), 52.0 (C-4''), 48.8 (C-1), 48.2 (C-3), 47.8 (C-2'), 29.9 ($NCH_3$), 28.1 (C-2), 26.6 (C-3'); ESI-HRMS: m/z calcd. for $C_{24}H_{48}N_5O_{13}$ [M+H]$^+$ 614.3249; found, 614.3242.

5,2'',3'',6''-Tetra-O-acetyl-1,3,2',4''-tetraazido-6-O-(2-hydroxyethyl)-6',7'-oxazolidino-apramycin (AK-2). To a stirred solution of compound AK-1 (22 mg, 0.024 mmol) in THF (0.4 mL) and water (0.1 mL), $NaIO_4$ (15.5 mg, 0.07 mmol) was added and the reaction mixture was stirred at rt for 12 h. The reaction mixture was diluted with EtOAc and washed with aqueous $NaHCO_3$ and brine. The organic layer was dried over $Na_2SO_4$ and concentrated. To a solution of the residue in in THF (0.4 mL) and water (0.1 mL), $NaBH_4$ (1.8 mg, 0.048 mmol) and the reaction mixture was stirred at rt for 45 min. The reaction mixture was diluted with EtOAc and washed with aqueous $NaHCO_3$, brine, dried with $Na_2SO_4$ and concentrated. The crude product was purified using silica gel column chromatography (eluent: 0.75%-3% methanol/DCM) to give AK-2 (11 g, 52%) as a white solid;

$[\alpha]_D^{25}$=+60.6 (c 0.3, DCM); $^1H$ NMR (600 MHz, $CD_3OD$): δ 5.47-5.40 (m, 1H, H-3''), 5.38 (d, J=3.8 Hz, 1H, H-1''), 5.13 (d, J=2.1 Hz, 1H, H-8'), 5.02 (t, J=9.7 Hz, 1H, H-5), 4.97 (dd, J=10.3, 3.8 Hz, 1H, H-2''), 4.92-4.86 (m, 3H, H-1', H-5', H-6'), 4.35 (d, J=12.1 Hz, 1H, H-6''), 4.25 (dd, J=12.3, 4.1 Hz, 1H, H-6''), 4.10 (dd, J=8.9, 2.1 Hz, 1H, H-7'), 3.89-3.79 (m, 4H, H-4', H-4'', H-5'', $CH_2OHCH_2O$), 3.79-3.73 (m, 1H, H-3), 3.72-3.63 (m, 2H, H-4, $CH_2OHCH_2O$), 3.63-3.54 (m, 3H, H-1, $CH_2OHCH_2O$), 3.57-3.49 (m, 1H, H-2'), 3.37 (t, J=9.8 Hz, 1H, H-6), 2.91 (s, 3H, $NCH_3$), 2.44 (dt, J=12.7, 4.6 Hz, 1H, H-2), 2.28 (dt, J=8.8, 4.2 Hz, 1H, H-3'), 2.18-2.04 (m, 12H, 4*$COCH_3$), 1.85-1.79 (m, 1H, H-3'), 1.61 (q, J=12.5 Hz, 1H, H-2); $^{13}C$ NMR (151 MHz, $CD_3OD$): δ 170.9 (C=O), 170.5 (C=O), 170.4 (C=O), 158.2 (C=O), 99.1 (C-1'), 93.9 (C-1''), 93.0 (C-8'), 82.5 (C-6), 80.2 (C-4), 74.5 (C-5), 74.1 ($CH_2OHCH_2O$), 70.9 (C-3''), 70.2 (C-2''), 70.0 (C-6'), 68.7 (C-5''), 65.1 (C-5'), 65.1 (C-4'), 62.9 (C-6''), 60.8 ($CH_2OHCH_2O$), 60.1 (C-4''), 59.9 (C-7'), 59.8 (C-1), 58.2 (C-3), 56.6 (C-2'), 31.1 (C-2), 30.1 (C-3'), 28.6 ($NCH_3$), 20.1 ($COCH_3$), 20.0 ($COCH_3$), 19.4 ($COCH_3$), 19.2 ($COCH_3$); ESI-HRMS: m/z calcd. for $C_{32}H_{43}N_{13}NaO_{17}$ [M+Na]$^+$ 904.2798; found, 904.2801.

6-O-(2-Hydroxyethyl)-apramycin pentaacetate salt (DCWSU167). A stirred solution of compound 176 (10 mg, 0.011 mmol) in dioxane (0.2 mL) was treated with 3N NaOH (0.2 mL) and heated at 100° C. for 1 h. 1M $P(CH_3)_3$ in THF (0.15 mL) was added and the reaction mixture was stirred at 55° C. for 2 h. The reaction mixture was cooled to 0° C., neutralized with glacial acetic acid and concentrated. The crude product was dissolved in aqueous acetic acid solution (pH 4, 1 mL) then charged to a Sephadex column (CM Sephadex C-25). The column was flushed with D.I. water (20 mL), then gradient eluted with 0.1%-1.0% $NH_4OH$ in D.I. water. The fractions containing the product were combined, acidified with glacial acetic acid, and lyophilized to afford DCWSU167 (6.3 mg, 63%) as the peracetate salt in the form of a white solid; $[\alpha]_D^{25}$=+107.38 (c 0.4, $H_2O$); $^1H$ NMR (600 MHz, $D_2O$): δ 5.52 (d, J=3.8 Hz, 1H, H-1'), 5.32 (d, J=4.0 Hz, 1H, H-1''), 5.04 (d, J=8.5 Hz, 1H, H-8'), 4.38 (s, 1H, H-6'), 3.90-3.84 (m, 1H, $CH_2OHCH_2O$), 3.80-3.66 (m, 5H, H-4, H-4', H-3'', H-5'', H-6''), 3.66-3.55 (m, 6H, H-5, H-5', H-6'', $CH_2OHCH_2O$, $CH_2OHCH_2O$), 3.54 (dd, J=9.7, 4.0 Hz, 1H, H-2''), 3.47 (dt, J=13.0, 4.1 Hz, 1H, H-2'), 3.33 (t, J=9.7 Hz, 1H, H-6), 3.27-3.15 (m, 3H, H-1, H-3, H-7'), 3.08 (t, J=10.3 Hz, 1H, H-4''), 2.61 (s, 3H, $NCH_3$), 2.31-2.24 (m, 1H, H-2), 2.20 (dt, J=8.7, 3.9 Hz, 1H, H-3'), 1.86 (q, J=11.6 Hz, 1H, H-3'), 1.64 (q, J=11.7, 11.0 Hz, 1H, H-2); $^{13}C$ NMR (151 MHz, $D_2O$): δ 95.6 (C-1'), 94.4 (C-1''), 92.9 (C-8'), 81.5 (C-6), 79.0 (C-4), 75.3 (C-5), 74.0 ($CH_2OHCH_2O$), 70.2 (C-2''), 69.7 (C-5'), 69.6 (C-5''), 68.6 (C-3''), 66.0 (C-4'), 62.8 (C-6'), 60.8 ($CH_2OHCH_2O$), 60.3 (C-6''), 59.4 (C-7'), 52.0 (C-4''), 49.1 (C-1), 48.3 (C-3), 47.9 (C-2'), 30.0 ($NCH_3$), 28.9 (C-2), 26.8 (C-3'); ESI-HRMS: m/z calcd. for $C_{24}H_{48}N_5O_{13}$ [M+H]$^+$ 584.3143; found, 584.3129.

Example 9

DCWSU177

Figure 5:
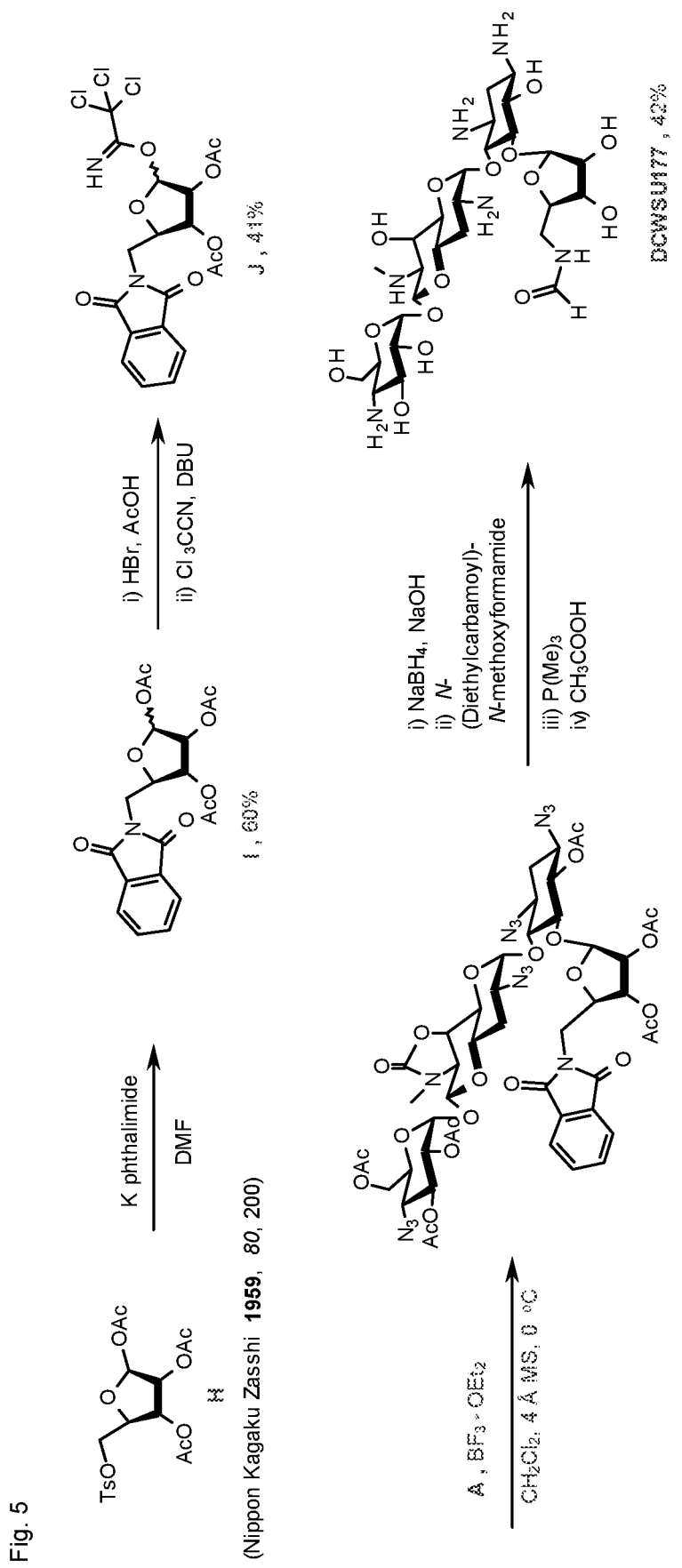

See the synthetic scheme of FIG. 5.

1,2,3-Tri-O-acetyl-5-deoxy-5-phthalimido-α-D-ribofuranose (I). 1,2,3-Tri-O-acetyl-5-O-p-tolylsulfonyl-D-ribofuranose H (1.00 g, 2.3 mmol) was dissolved in dry DMF (20 mL) and treated with potassium phthalimide (1.00 g, 5.4 mmol). The reaction mixture was stirred at 50° C. for 12 h before it was diluted with water and extracted with DCM three times. The organic layer wash then washed with 5% aqueous NaOH and brine, dried over $Na_2SO_4$, and concentrated. The residue was purified using silica gel column chromatography (eluent: 15% –35% EtOAc/hexanes) to give I (566 mg, 60%) as a white solid; $[\alpha]_D^{25}$=+49.66 (c 1.3, DCM); $^1$H NMR (400 MHz, CDCl$_3$): δ 7.80-7.73 (m, 2H, ArH), 7.70-7.62 (dd, J=5.4, 3.1 Hz, 2H, ArH), 6.34 (d, J=4.5 Hz, 1H, H-1), 5.23 (dd, J=6.8, 4.5 Hz, 1H, H-2), 5.15 (dd, J=6.7, 3.4 Hz, 1H, H-3), 4.48 (td, J=6.8, 3.4 Hz, 1H, H-4), 3.86 (dd, J=6.8, 5.2 Hz, 2H, H-5), 2.03-1.95 (m, 9H, COCH$_3$);$^{13}$C NMR (101 MHz, CDCl$_3$): δ 169.9 (C=O), 169.4 (C=O), 169.2 (C=O), 168.0 (C=O), 134.1 (ArC), 131.8 (ArC), 123.4 (ArC), 93.7 (C-1), 80.4 (C-4), 70.7 (C-3), 69.6 (C-2), 39.3 (C-5), 20.9 (COCH$_3$), 20.5 (COCH$_3$), 20.2 (COCH$_3$); ESI-HRMS: m/z calcd. for $C_{19}H_{19}NNaO_9$ [M+Na]$^+$ 428.0958; found, 428.0964.

2,3-Di-O-acetyl-5-deoxy-5-phthalimido-D-ribofuranosyl trichloroacetimidate (J). To an ice-cooled solution of I (550 mg, 1.36 mmol) in DCM (5 mL), 33% HBr/acetic acid (0.7 mL, 4.07 mmol) was added followed by stirring for 45 min. After completion, solid NaHCO$_3$ was added to neutralize the reaction, then water was added and the aqueous layer was extracted with DCM three times. The organic layer was washed with brine, dried over $Na_2SO_4$ and concentrated. The residue was purified using silica gel column chromatography (eluent: 20% –60% EtOAc/hexanes) to give 2,3-di-O-acetyl-5-deoxy-5-phthalimido-α/β-D-ribofuranose as a mixture of anomers α:β=1:3 (200 mg, 41%) that was used directly in the next step. 2,3-Di-O-acetyl-5-deoxy-5-phthalimido-α/β-D-ribofuranose (190 mg, 0.53 mmol) and trichloroacetonitrile (2 mL) were dissolved in dry DCM (2 mL) and ice-cooled before addition of DBU (2 drops). The reaction mixture was stirred at rt for 5 min and concentrated. The crude product was passed through a silica gel column, basified with 0.5% triethylamine/hexanes, eluting with 0.5% triethylamine in EtOAc/hexanes to give compound J (270 mg, quant) which was used in the next step without further purification.

5-O-β-(2''', 3'''-Di-O-acetyl-5'''-deoxy-5'''-phthalimido-D-ribofuranosyl)-6,2'',3'',6''-tetra-O-acetyl-1,3,2',4''-tetraazido-6',7'-oxazolidino-apramycin (K). Donor I (190 mg, 0.52 mmol), acceptor A (701 mg, 0.84 mmol) and activated 4 Å MS were stirred in dry DCM (3 mL) at rt for 1 h before cooling to 0° C. BF$_3$.OEt$_2$ (400 μL, 1.08 mmol) was added and reaction mixture was stirred for 2 h at 0° C. The reaction was quenched with triethylamine (0.5 mL) and filtered through Celite® before it was diluted with EtOAc and washed with aqueous NaHCO$_3$ and brine. The organic layer was dried over $Na_2SO_4$ and concentrated. The crude product was purified using silica gel column chromatography (eluent: 0.6%-1.5% methanol/DCM) to give the glycoside K (470 mg, 76%) as the β anomer in the form of a white solid; $[\alpha]_D^{25}$=+131.96 (c 5.3, DCM); $^1$H NMR (400 MHz, CDCl$_3$): δ 7.95-7.88 (m, 2H, ArH), 7.77-7.70 (m, 2H, ArH), 5.39 (t, J=9.9 Hz, 1H, H-3''), 5.34 (d, J=3.8 Hz, 2H, H-1', H-1''), 5.30 (s, 1H, H-1'''), 5.12 (d, J=4.9 Hz, 1H, H-2'''), 5.06 (dd, J=7.2, 4.8 Hz, 1H, H-3'''), 4.95-4.88 (m, 2H, H-8', H-2''), 4.83 (dd, J=8.2, 2.9 Hz, 1H, H-6'), 4.66 (dd, J=10.5, 2.9 Hz, 1H, H-5'), 4.46 (t, J=9.9 Hz, 1H, H-6), 4.42-4.29 (m, 2H, H-6'', H-4'''), 4.22 (dd, J=12.2, 5.2 Hz, 1H, H-6''), 3.96 (d, J=5.0 Hz, 2H, H-5'''), 3.84-3.68 (m, 3H, H-4', H-6', H-5''), 3.65-3.53 (m, 3H, H-3, H-4, H-4''), 3.46-3.28 (m, 3H, H-1, H-5, H-2'), 2.94 (s, 3H, NCH$_3$), 2.41 (dt, J=12.6, 4.3 Hz, 1H, H-2), 2.23 (s, 4H, COCH$_3$), 2.13-1.98 (m, 15H, 5*COCH$_3$), 1.78 (q, J=11.7 Hz, 1H, H-3'), 1.43 (q, J=12.6 Hz, 1H, H-2);$^{13}$C NMR (101 MHz, CDCl$_3$): δ 170.3 (C=O), 170.2 (C=O), 169.9 (C=O), 169.8 (C=O), 169.5 (C=O), 168.2 (C=O), 157.2 (C=O), 134.1 (ArC), 132.0 (ArC), 123.7 (ArC), 106.9 (C-1'''), 97.0 (C-1'), 94.8 (C-8'), 93.8 (C-1''), 79.8 (C-5), 79.1 (C-4'''), 78.9 (C-4), 74.0 (2''), 73.4 (C-6), 72.6 (C-3'''), 70.7 (C-6'), 70.3 (C-3''), 69.9 (C-2''), 68.9 (C-5''), 65.4 (C-5'), 65.3 (C-4'), 62.9 (C-6''), 60.21 (C-7'), 60.16 (C-4''), 58.4 (C-3), 58.2 (C-1), 57.7 (C-2'), 39.5 (C-5'''), 31.4 (C-2), 31.3 (C-3'), 29.9 (NCH$_3$), 20.9 (COCH$_3$), 20.8 (COCH$_3$), 20.8 (COCH$_3$), 20.7 (COCH$_3$), 20.6 (COCH$_3$), 20.4 (COCH$_3$); ESI-HRMS: m/z calcd. for $C_{47}H_{54}N_{14}NaO_{23}$ [M+Na]$^+$ 1205.3384; found, 1205.3359.

5-O-β-(5'''-Formamido-5'''-deoxy-D-ribefuranosyl) apramycin pentaacetate salt (DCWSU177). To a stirred solution of compound K (50 mg, 0.04 mmol) in an IPA:water mixture (7:3, 1.5 mL), NaBH$_4$ (90 mg, 2.4 mmol) was added followed by stirring for 2 h. The reaction mixture was diluted with methanol and glacial acetic acid was added dropwise until effervescence stopped. The reaction mixture was concentrated in vacuo followed by the addition of 3 N NaOH (0.5 mL) and water (0.5 mL). The reaction mixture was heated at 100° C. for 1 h before it was cooled, neutralized with glacial acetic acid and concentrated. The crude mixture was desalted using a Sephadex column and the product-containing fractions were concentrated. A part of the solid residue (8.2 mg, 0.009 mmol) was dissolved in water (0.2 mL) and treated with N-(diethylcarbamoyl)-N-methoxyformamide (2.4 μL, 0.014 mmol) and triethylamine (1 μL). The reaction mixture was stirred for 2 h and quenched with ammonium hydroxide (0.25 mL) followed by addition of 1M P(CH$_3$)$_3$ in THF (0.3 mL) and stirring at 60° C. for 3 h. The reaction mixture was then concentrated to dryness and dissolved in aqueous acetic acid solution (pH 4, 1 mL) before it was charged to a Sephadex column (CM Sephadex C-25). The column was flushed with D.I. water (20 mL), then gradient eluted with 0.1%-1.0% NH$_4$OH in D.I. water. The fractions containing the product were combined, acidified with acetic acid and lyophilized to afford DCWSU177 in (4.5 mg, 42%) as the peracetate salt in the form of a white solid; $[\alpha]_D^{25}$=+82.2 (c 0.2, H$_2$O);$^1$H NMR (600 MHz, D$_2$O): δ 7.98 (s, 1H, CHO), 5.67 (d, J=3.9 Hz, 1H, H-1'), 5.34 (d, J=3.9 Hz, 1H, H-1''), 5.14 (d, J=2.9 Hz, 1H, H-1'''), 5.06 (d, J=8.5 Hz, 1H, H-8'), 4.46-4.39 (m, 1H, H-6'), 4.02 (dd, J=4.4, 3.2 Hz, 1 H, H-2''), 3.94 (t, J=5.3 Hz, 1H, H-3'''), 3.90 (q, J=5.7 Hz, 1H, H-3''), 3.85-3.67 (m, 6H, H-4, H-5, H-4', H-3'', H-5'', H-6), 3.63 (dd, J=12.5, 4.6 Hz, 1H, H-6''), 3.56 (dd, J=9.8, 3.8 Hz, 1H, H-2''), 3.54-3.50 (m, 3H, H-6, H-2', H-5'), 3.42 (dd, J=14.6, 4.2 Hz, 1H, H-5'''), 3.32 (dd, J=14.6, 6.2 Hz, 1H, H-5'''), 3.29-3.23 (m, 1H, H-3), 3.22 (dd, J=8.5, 2.7 Hz, 1H, H-7'), 3.16 (td, J=11.6, 10.9, 4.3 Hz, 1H, H-1), 3.10 (t, J=10.3 Hz, 1H, H-4''), 2.63 (s, 3H, NCH$_3$), 2.30-2.16 (m, 2H, H-2, H-3'), 1.94-1.83 (m, 1H, H-3'), 1.68-1.55 (m, 1H, H-2); $^{13}$C NMR (151 MHz, D$_2$O): δ 164.7(CHO), 110.0 (C-1'''), 94.4 (C-1''), 94.0 (C-1'), 92.9 (C-8'), 85.1 (C-5), 80.9 (C-4'''), 76.4 (C-4), 74.7 (C-2'''), 72.5 (C-6), 70.8 (C-3'''), 70.2 (C-2''), 69.7 (C-5''), 69.7 (C-4'), 68.6 (C-3''), 65.9 (C-5'), 62.7 (C-6'), 60.3 (C-6''), 59.4 (C-7'), 52.0 (C-4''), 49.8 (C-3), 48.5 (C-1), 47.7 (C-2'), 40.0 (C-5'''), 30.0 (NCH$_3$), 28.9 (C-2), 26.8 (C-3'); ESI-HRMS: m/z calcd. for $C_{27}H_{51}N_6O_{15}$ [M+H]$^+$ 699.3412; found, 699.3410.

Example 10

DCWSU 178

Figure 6:
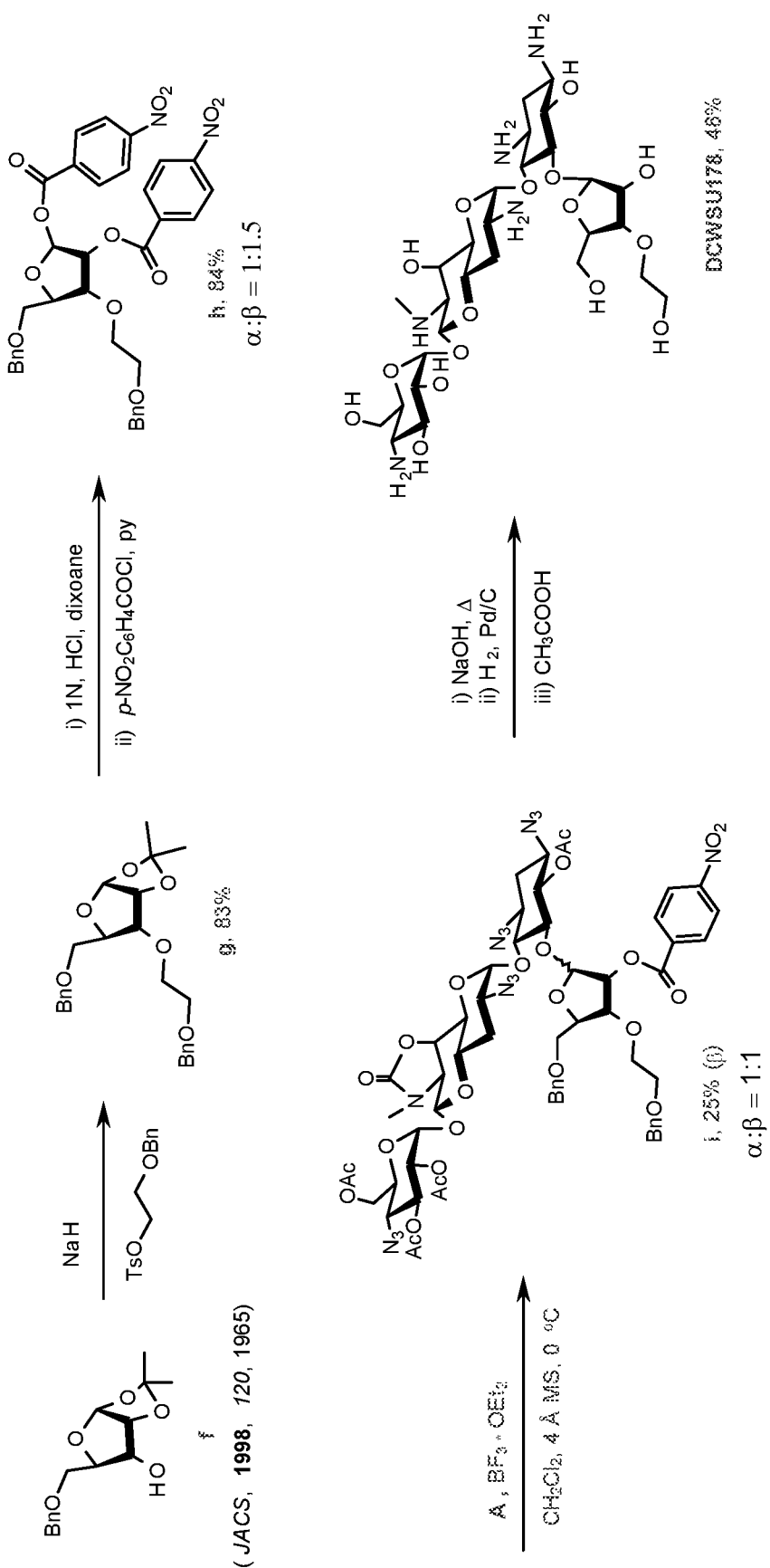

See the synthetic scheme of FIG. 6.

5-O-Benzyl-3-O-(2-benzyloxyethyl)-1,2-O-isopropylidene-α-D-ribofuranose (g). 5-O-benzyl-1,2-O-isopropylidene-α-D-ribofuranose f (1.00 g, 3.57 mmol) was dissolved in dry THF (20 mL) and NaH (185 mg, 4.64 mmol) was added under argon. After stirring for 15 min, 2-benzyloxyethyl tosylate (1.31 g, 4.29 mmol) was added and stirring continued for 12 h. More NaH (185 mg, 4.64 mmol) and 2-benzyloxyethyl tosylate (1.31 g, 4.29 mmol) were added and the mixture stirred for 24 h. After completion, the reaction was quenched with methanol, diluted with EtOAc and washed with aqueous NaHCO$_3$ and brine. The organic layer was dried over Na$_2$SO$_4$ and concentrated. The crude product was purified using silica gel column chromatography (eluent: 5% to 12% EtOAc/hexanes) to give g (1.24 g, 83%) in the form of a colorless oil; $[\alpha]_D^{25}$=+42.22 (c 2.2, DCM); $^1$H NMR (400 MHz, CDCl$_3$): δ 7.39-7.26 (m, 10H, ArH), 5.77 (d, J=3.7 Hz, 1H, H-1), 4.63 (d, J=4.1 Hz, 1H, H-2), 4.61 (d, J=4.1 Hz, 1H, CH$_2$Ph), 4.58-4.52 (m, 3H, CH$_2$Ph), 4.14 (ddd, J=9.1, 4.1, 2.0 Hz, 1H, H-4), 3.92-3.76 (m, 3H, H-3, H-5, CH$_2$CH$_2$), 3.76-3.56 (m, 4H, H-5, 3H—CH$_2$CH$_2$), 1.57 (s, 3H, CH$_3$), 1.35 (s, 3H, CH$_3$); $^{13}$C NMR (101 MHz, CDCl$_3$): δ 138.2 (ArC), 138.1 (ArC), 128.4 (ArC), 128.3 (ArC), 127.73 (ArC), 127.69 (ArC), 127.67 (ArC), 127.63 (ArC), 127.59 (ArC), 112.8(C(CH$_3$)$_2$), 104.0 (C-1), 79.0 (C-3), 77.9 (C-4), 77.5 (C-2), 73.5 (CH$_2$Ph), 73.2 (CH$_2$Ph), 70.7 (CH$_2$CH$_2$), 70.1 (CH$_2$CH$_2$), 68.2 (C-5), 26.8 (CH$_3$), 26.5 (CH$_3$); ESI-HRMS: m/z calcd. for C$_{24}$H$_{30}$NaO$_6$ [M+Na]$^+$ 437.1940; found, 437.1939.

5-O-Benzyl-3-O-(2-benzyloxyethyl)-1,2-di-O-(4-nitrobenzoyl)-α-D-ribofuranose (hα) and 5-O-Benzyl-3-O-(2-benzyloxyethyl)-1,2-di-O-(4-nitrobenzoyl)-β-D-ribofuranose (hβ). To a stirred solution of compound g (600 mg, 1.45 mmol) in dioxane (10 mL), 1 N HCl (5 mL) was added and the reaction mixture was heated at 80° C. for 45 min. The reaction mixture was cooled, neutralized with solid NaHCO$_3$ then the solvent was evaporated. The residue was dissolved in EtOAc and washed with water and brine. The organic layer was dried over Na$_2$SO$_4$ and concentrated. To a solution of the residue in dry pyridine (10 mL), p-nitrobenzoyl chloride (672 mg, 3.6 mmol) and a catalytic amount of DMAP were added followed by stirring overnight. The reaction mixture was concentrated then diluted with EtOAc and washed with aqueous NaHCO$_3$, brine, dried with Na$_2$SO$_4$ and concentrated. The crude product was purified using silica gel column chromatography (eluent: 5%-25% EtOAc/hexanes) to give h α:β=1:1.5 (820 g, 84%, yellow oil). Further purification was done to separate analytical sample of anomers: hα (86 mg, 9%, yellow oil), hβ (63 mg, 6%, yellow oil); α anomer: $[\alpha]_D^{25}$=+74.69 (c 5.7, DCM); $^1$H NMR (400 MHz, CDCl$_3$): δ 8.26-8.21 (m, 2H, ArH), 8.19-8.14 (m, 2H, ArH), 8.11-8.07 (m, 4H, ArH), 7.42-7.27 (m, 5H, ArH), 7.27-7.22 (m, 3H, ArH), 7.20-7.06 (m, 2H, ArH), 6.81 (d, J=4.4 Hz, 1H, H-1), 5.47 (dd, J=6.3, 4.4 Hz, 1H, H-2), 4.66-4.53 (m, 3H, H-4, CH$_2$Ph), 4.49-4.41 (m, 2H, CH$_2$Ph), 4.38 (dd, J=6.3, 2.8 Hz, 1H, H-3), 3.81-3.73 (m, 2H, CH$_2$CH$_2$), 3.71-3.65 (m, 2H, H-5), 3.66-3.56 (m, 2H, CH$_2$CH$_2$); $^{13}$C NMR (101 MHz, CDCl$_3$): δ 163.7 (C=O), 163.6 (C=O), 150.7 (ArC), 150.7 (ArC), 137.8 (ArC), 137.6 (ArC), 135.1 (ArC), 134.5 (ArC), 131.0 (ArC), 130.7 (ArC), 128.5 (ArC), 128.4 (ArC), 127.9 (ArC), 127.7 (ArC), 127.3 (ArC), 123.6 (ArC), 96.0 (C-1), 85.0 (C-4), 76.9 (C-3), 73.7 (CH$_2$Ph), 73.4 (CH$_2$Ph), 73.2 (C-2), 71.2 (CH$_2$CH$_2$), 69.9 (CH$_2$CH$_2$), 69.5 (C-5); ESI-HRMS: m/z calcd. for C$_{35}$H$_{32}$N$_2$NaO$_{12}$ [M+Na]$^+$ 695.1853; found, 695.1859; β anomer: $[\alpha]_D^{25}$=−11.33 (c 0.042, DCM); $^1$H NMR (400 MHz, CDCl$_3$): δ 8.22 (m, 4H, ArH), 8.12-8.05 (m, 2H, ArH), 8.05-7.99 (m, 2H, ArH), 7.29-7.16 (m, 10H, ArH), 6.55 (s, 1H, H-1), 5.74 (d, J=4.4 Hz, 1H, H-2), 4.66 (dd, J=7.7, 4.4 Hz, 1H, H-3), 4.51 (s, 2H, CH$_2$Ph), 4.46-4.39 (m, 3H, H-4, CH$_2$Ph), 3.85 (dd, J=11.0, 2.7 Hz, 1H, H-5), 3.83-3.75 (m, 2H, CH$_2$CH$_2$), 3.72 (dd, J=11.1, 3.5 Hz, 1H, H-5), 3.64-3.53 (m, 2H, CH$_2$CH$_2$); $^{13}$C NMR (101 MHz, CDCl$_3$): δ 163.6 (C=O), 163.0 (C=O), 150.7 (ArC), 150.6 (ArC), 137.9 (ArC), 137.8 (ArC), 134.6 (ArC), 131.0 (ArC), 130.9 (ArC), 128.4 (ArC), 128.3 (ArC), 127.7 (ArC), 127.6 (ArC), 127.5 (ArC), 123.6 (ArC), 123.5 (ArC), 99.5 (C-1), 82.2 (C-4), 77.3 (C-3), 75.2 (C-2), 73.5 (CH$_2$Ph), 73.2 (CH$_2$Ph), 71.1 (CH$_2$CH$_2$), 69.7 (CH$_2$CH$_2$), 68.8 (C-5); ESI-HRMS: m/z calcd. for C$_{35}$H$_{32}$N$_2$NaO$_{12}$ [M+Na]$^+$ 695.1853; found, 695.1846.

5-O-β-[5'''-O-Benzyl-3'''-O-(2-benzyloxyethyl)-1''',2'''-di-O-(4-nitrobenzoyl)-D-ribefuranosyl]-6,2'',3'',6''-tetra-O-acetyl-1,3,2',4''-tetraazido-6',7'-oxazolidino-apramycin (i). Donor h (161 mg, 0.24 mmol), acceptor A (67 mg, 0.08 mmol) and activated 4 Å MS were stirred in dry DCM at rt for 1 h before cooling to 0° C. BF$_3$.OEt$_2$(100 μL, 0.27 mmol) was added and reaction mixture was stirred for 48 h at 0° C. The reaction was quenched with triethylamine (0.5 mL) and filtered through Celite® before dilution with EtOAc and washing with aqueous NaHCO$_3$ and brine and concentration. The crude product was purified using silica gel column chromatography (eluent: 0.6%-1.5% methanol/DCM) to give the β anomer i (14 mg, 13%) as a white solid. An approximately equal amount of the α-anomer was also obtained but not charwcterized. $[\alpha]_D^{25}$=+56.85 (c 0.7, DCM); $^1$H NMR (600 MHz, CDCl$_3$): δ 8.20-8.11 (m, 4H, ArH), 7.40-7.30 (m, 5H, ArH), 7.24-7.10 (m, 5H, ArH), 5.80 (d, J=3.6 Hz, 1H, H-1'), 5.43 (t, J=10.0 Hz, 1H, H-3''), 5.39-5.34 (m, 2H, H-1'', H-1'''), 5.26 (d, J=4.3 Hz, 1H, H-2'''), 4.91 (t, J=9.7 Hz, 1H, H-6), 4.87 (dd, J=10.3, 3.9 Hz, 1H, H-2''), 4.81 (d, J=4.5 Hz, 1H, H-8'), 4.76 (dd, J=7.4, 3.3 Hz, 1H, H-6'), 4.57 (d, J=12.0 Hz, 1H, CH$_2$Ph), 4.51 (d, J=12.0 Hz, 1H, CH$_2$Ph), 4.39 (dd, J=10.3, 3.4 Hz, 1H, H-5'), 4.37-4.31 (m, 3H, CH$_2$Ph, H-6''), 4.27-4.19 (m, 2H, H-6'', H-4'''), 4.14 (dd, J=7.5, 4.4 Hz, 1H, H-3'''), 3.87-3.71 (m, 4H, H-5, H-7', H-5'', H-5'''), 3.71-3.63 (m, 3H, H-4, CH$_2$CH$_2$), 3.63-3.52 (m, 4H, H-3, H-5'' H-4', H-4''), 3.51-3.37 (m, 3H, H-1, CH$_2$CH$_2$), 3.08 (dt, J=12.9, 4.2 Hz, 1H, H-2'), 2.95 (s, 3H, NHCH$_3$), 2.41 (dt, J=13.1, 4.5 Hz, 1H, H-2), 2.23-1.97 (m, 13H, 4COCH$_3$, H-3'), 1.87 (q, J=11.7 Hz, 1H, H-3'), 1.57 (q, J=12.6 Hz, 1H, H-2); $^{13}$C NMR (151 MHz, CDCl$_3$): δ 170.3 (C=O), 170.1 (C=O), 169.8 (C=O), 169.7 (C=O), 163.8 (C=O), 157.1 (ArC), 150.7 (ArC), 137.9 (ArC), 137.9 (ArC), 134.7 (ArC), 130.8 (ArC), 128.5 (ArC), 128.2 (ArC), 127.7 (ArC), 127.6 (ArC), 127.5 (ArC), 127.4 (ArC), 123.6 (ArC), 107.2 (C-1'''), 97.3 (C-8'), 96.4 (C-1'), 94.2 (C-1''), 82.0 (C-5), 80.7 (C-4'''), 77.8 (C-4), 77.7 (C-3'''), 75.7 (C-2''), 75.0 (C-6), 73.4 (CH$_2$Ph), 73.0 (CH$_2$Ph), 71.0 (C-6'), 70.8 (C-3''), 70.4 (CH$_2$CH$_2$), 70.3 (C-5'''), 69.9 (C-2''), 69.2 (C-5''), 69.1 (CH$_2$CH$_2$), 65.9 (C-5'), 65.7 (C-4'), 62.9 (C-6''), 60.20 (C-4''), 60.17 (C-7'), 59.1 (C-3), 58.1 (C-1), 56.5 (C-2'), 31.3 (C-2), 30.1 (C-3'), 29.7 (NCH$_3$), 20.9 (COCH$_3$), 20.8 (COCH$_3$), 20.7 (COCH$_3$); ESI-HRMS: m/z calcd. for C$_{58}$H$_{66}$N$_{14}$NaO$_{24}$ [M+Na]$^+$ 1365.4272; found, 1365.4260.

5-O-β-[3'''-O-(2-Hydroxyethyl)-D-ribofuranosyl] apramycin pentaacetate salt (DCWSU178). A stirred solution of compound i (10 mg, 0.01 mmol) in dioxane (0.5 mL) was treated with 3N NaOH (0.25 mL) and heated at 100° C.

for 3 h. The reaction mixture was cooled to rt and neutralized with Amberlyst® before concentration in vacuo. The crude product was dissolved in dioxane:water:glacial acetic acid=1:2:0.2 (0.3 mL) and Pd(OH)$_2$/C (0.5 equiv) was added. The reaction mixture was stirred at room temperature under 50 psi of hydrogen for 12 h. After completion, the reaction mixture was filtered through Celite® and concentrated to dryness. The residue was then dissolved in aqueous acetic acid solution (pH 4, 1 mL) before it was charged to a Sephadex column (CM Sephadex C-25). The column was flushed with D.I. water (20 mL), then gradient eluted with 0.1%-1.0% NH$_4$OH in D.I. water. The fractions containing the product were combined, acidified with glacial acetic acid and lyophilized to afford DCWSU178 (3.5 mg, 48%) as the peracetate salt in the form of a white solid; $[\alpha]_D^{25}$=+72.0 (c 0.1, H$_2$O); $^1$H NMR (600 MHz, D$_2$O): δ 5.72 (d, J=3.6 Hz, 1H, H-1'), 5.34 (d, J=3.8 Hz, 1H, H-1"), 5.20 (s, 1H, H-1'''), 5.06 (d, J=8.5 Hz, 1H, H-8'), 4.43 (s, 1H, H-6'), 4.21 (d, J=4.3 Hz, 1H, H-2'''), 3.97-3.92 (m, 1H, H-4'''), 3.91-3.86 (m, 1H, H-4), 3.86-3.79 (m, 2H, H-5", H-3'''), 3.78-3.66 (m, 7H, H-5, H-4', H-5''', H-6", H-3", CH$_2$CH$_2$), 3.63 (dd, J=12.4, 4.6 Hz, 1H, H-6"), 3.60-3.55 (m, 3H, H-2", CH$_2$CH$_2$), 3.55-3.45 (m, 4H, H-6, H-2', H-6', H-5'''), 3.42-3.33 (m, 1H, H-3), 3.24 (d, J=8.9 Hz, 1H, H-7'), 3.21-3.09 (m, 2H, H—, H-1, H-4"), 2.63 (s, 3H, NCH$_3$), 2.32 (dt, J=12.3, 3.8 Hz, 1H, H-2), 2.23-2.15 (m, 1H, H-3'), 1.94-1.90 (m, 1H, H-3'), 1.70 (q, J=12.8 Hz, 1H, H-2); $^{13}$C NMR (151 MHz, D$_2$O): δ 110.4 (C-1'''), 94.6 (C-1'), 94.4 (C-1"), 92.8 (C-8'), 84.8 (C-5), 81.1 (C-4'''), 77.0 (C-3'''), 75.2 (C-4), 73.4 (C-2"), 72.4 (C-6), 71.4 (CH$_2$CH$_2$), 70.2 (C-5"), 69.7 (C-2"), 69.3 (C-3"), 68.2 (C-4'), 66.0 (C-5'), 62.6 (C-6'), 60.9 (C-5'''), 60.5 (CH$_2$CH$_2$), 60.3 (C-6"), 59.3 (C-7'), 52.0 (C-4"), 49.7 (C-3), 48.3 (C-1), 47.8 (C-2'), 30.0 (NCH$_3$), 28.0 (C-2), 26.6 (C-3'); ESI-HRMS: m/z calcd. for C$_{28}$H$_{54}$N$_5$O$_{16}$ [M+H]$^+$ 716.3566; found, 716.3541.

Example 11

DCWSU 185 and 186

Figure 7:
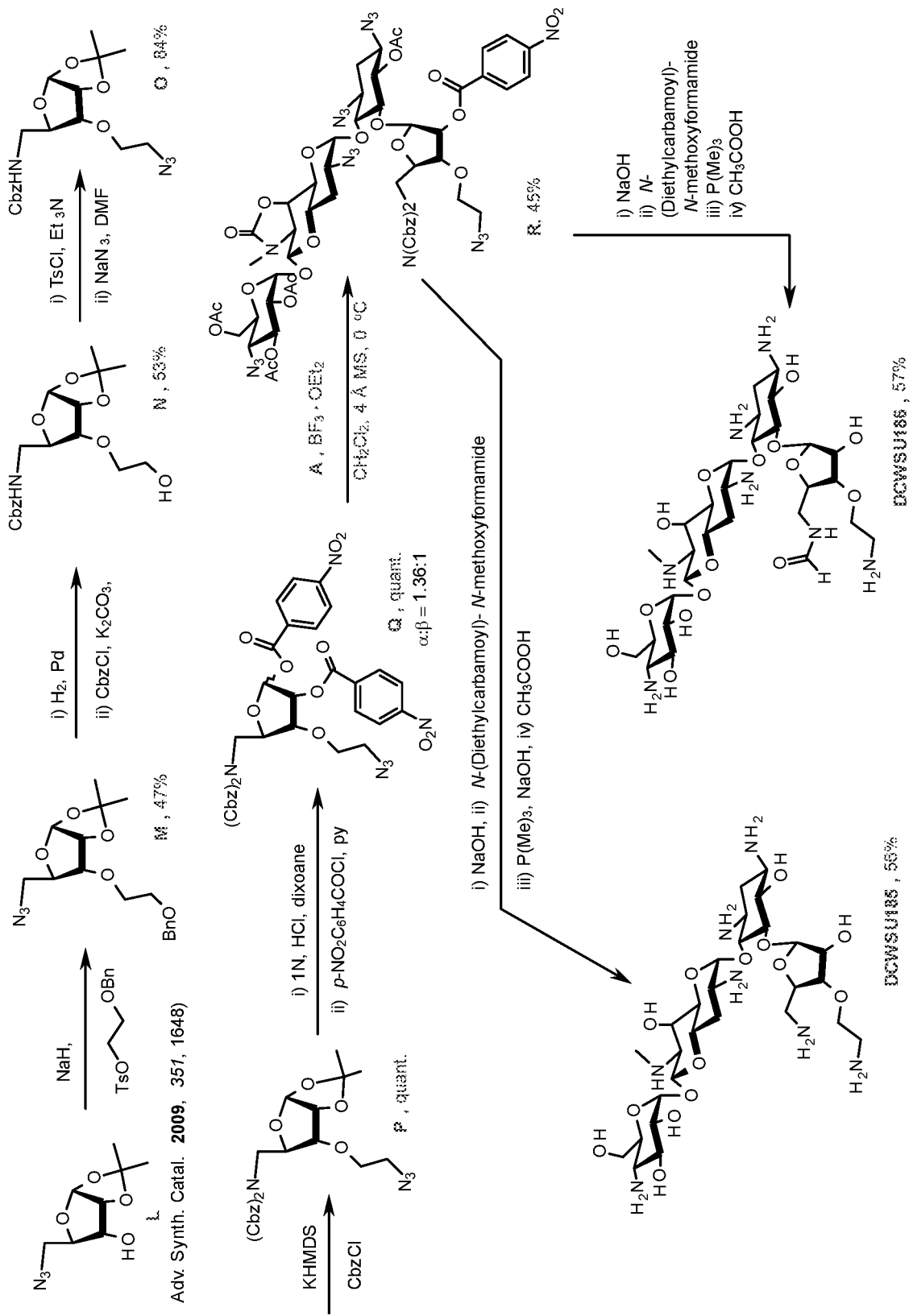
Figure 8:
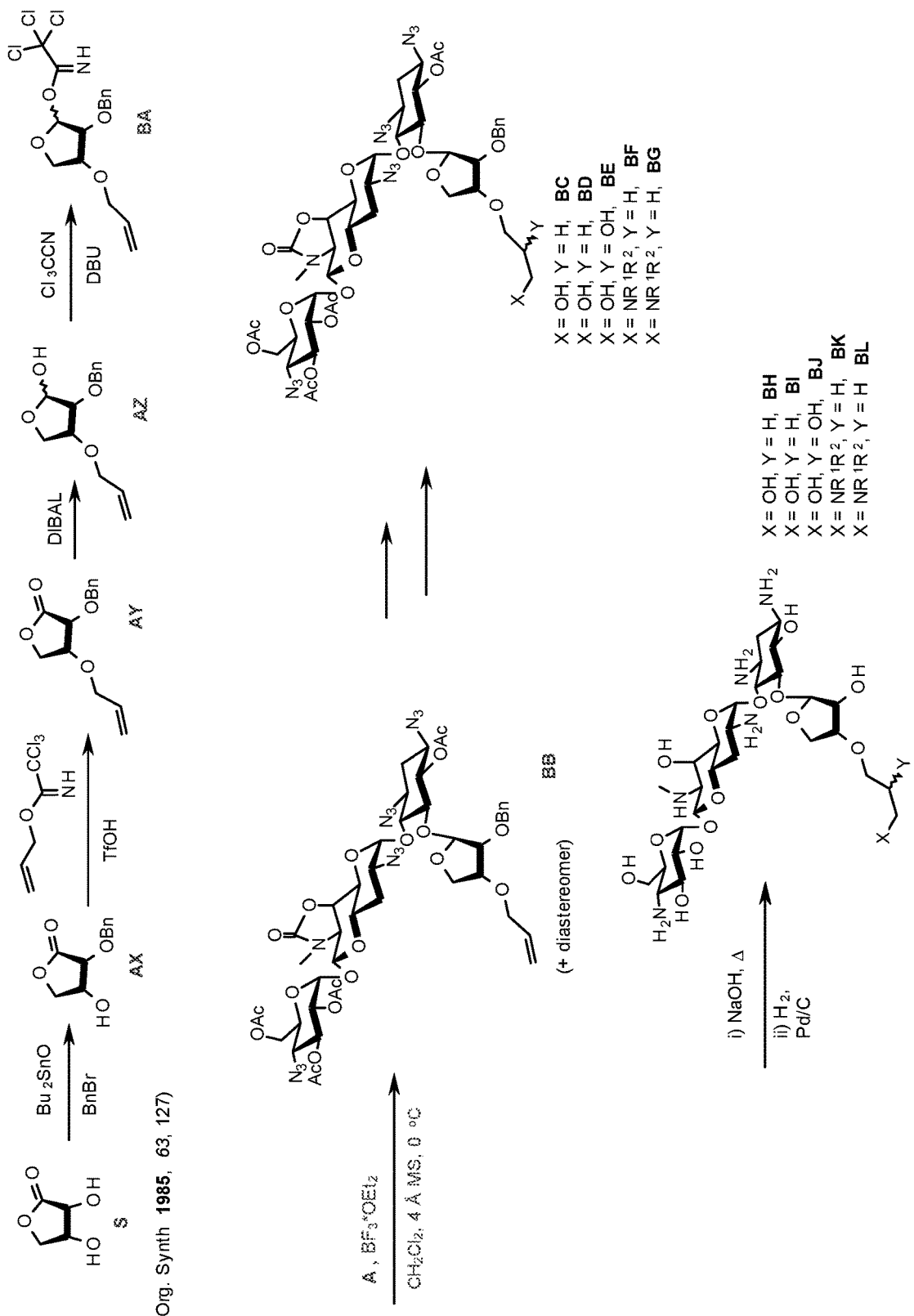
Figure 9:
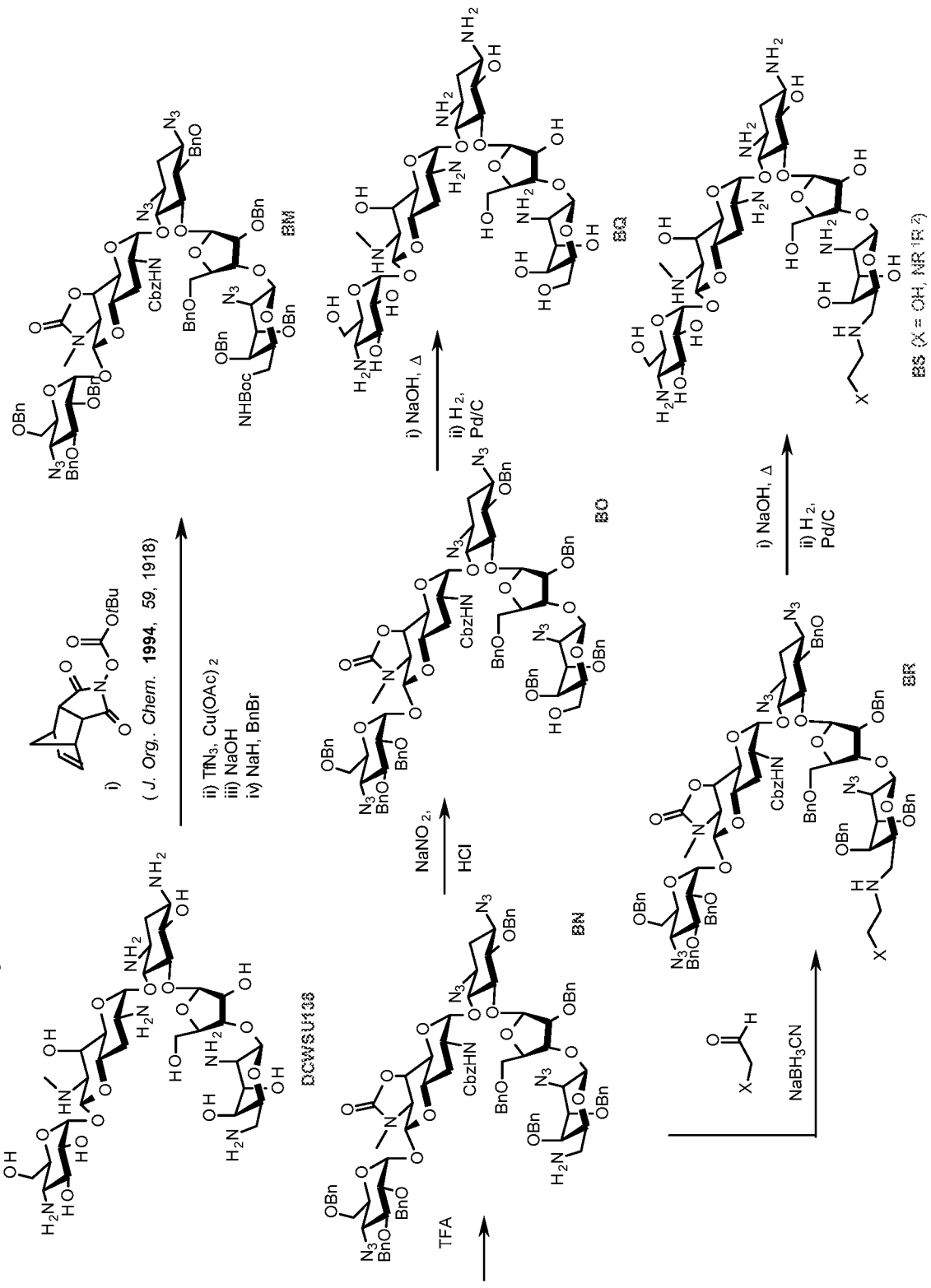
Figure 10:
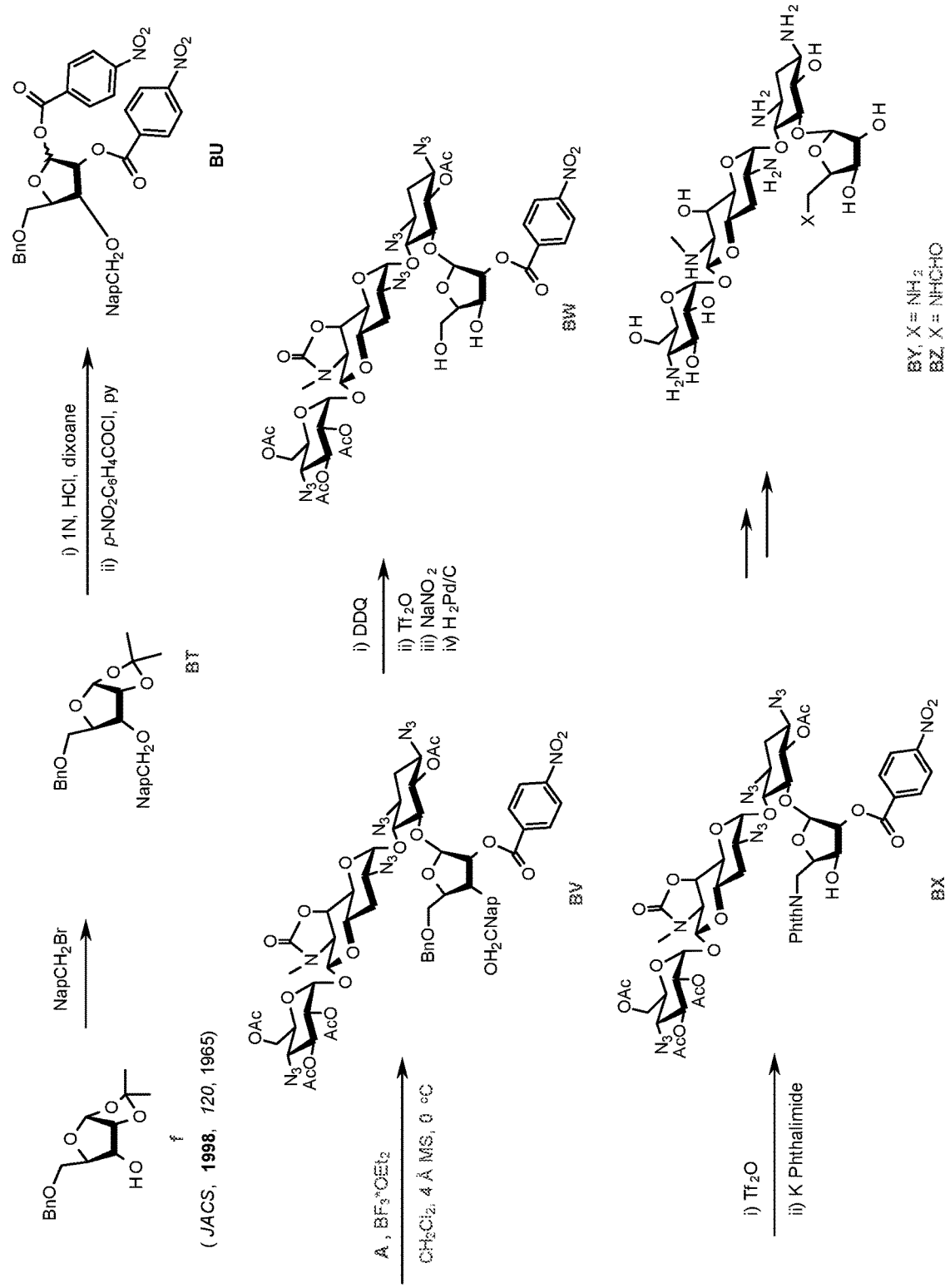
Figure 11:
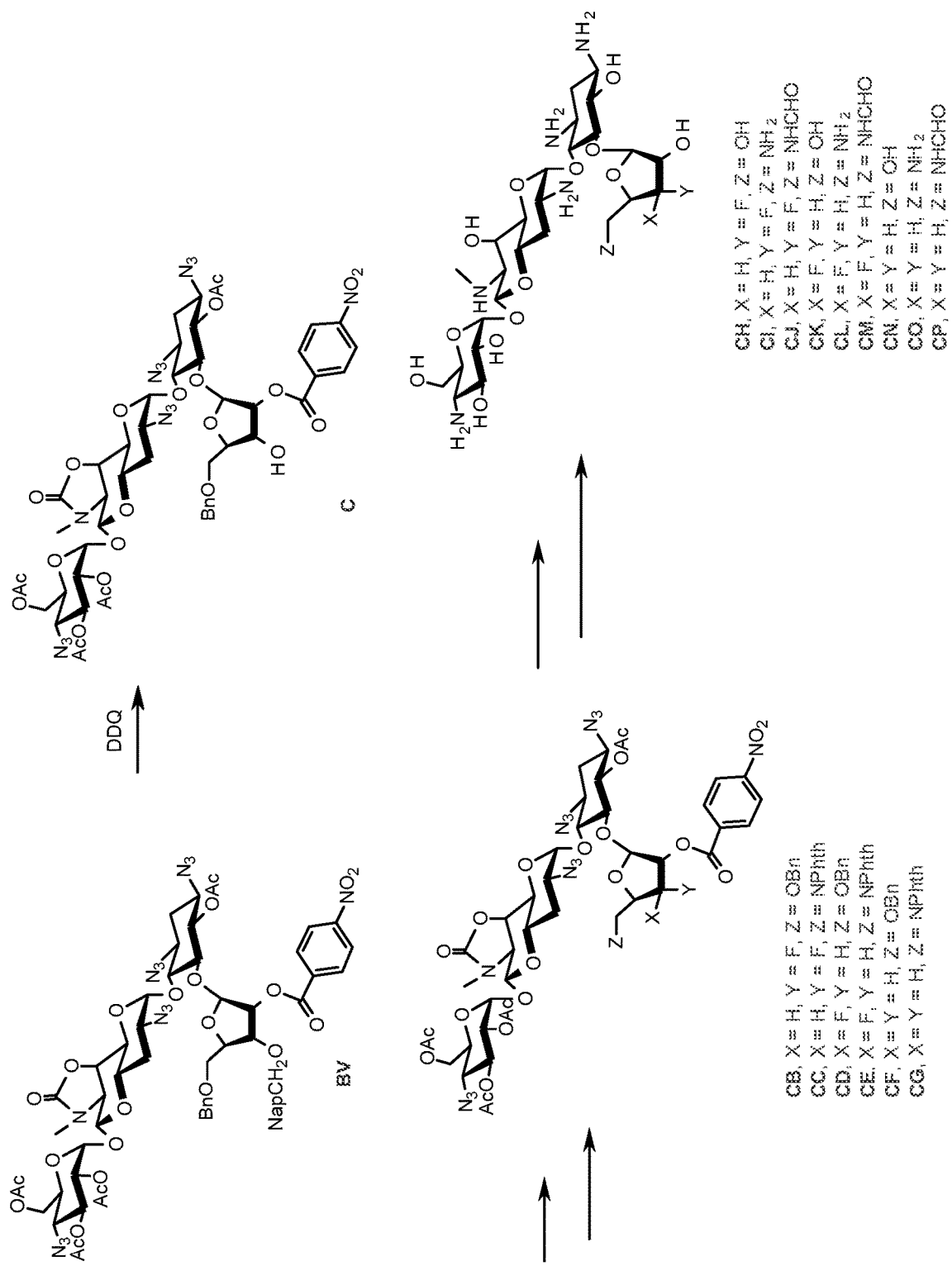

See the synthetic scheme of FIG. 7.

5-Azido-3-O-(2-benzyloxyethyl)-5-deoxy-1,2-O-isopropylidene-α-D-ribofuranose (M). 5-Azido-5-deoxy-1,2-O-isopropylidene-α-D-ribofuranose L (4.0 g, 18.6 mmol) was dissolved in dry THF (100 mL) and NaH (100 mg, 24.5 mmol) was added. After stirring for 15 min, 2-benzyloxyethyl tosylate (6.83 g, 22.3 mmol) was added and stirring continued for 36 h. After completion, the reaction was quenched with methanol, diluted with EtOAc and washed with aqueous NaHCO$_3$ and brine then concentrated. The crude product was purified using silica gel column chromatography (eluent: 10% to 20% EtOAc/hexanes) to give M (3.08 g, 47%) in the form of a colorless oil; $[\alpha]_D^{25}$=+119.83 (c 1.2, DCM); $^1$H NMR (400 MHz, CDCl$_3$): δ 7.45-7.21 (m, 5H, ArH), 5.76 (d, J=3.5 Hz, 1H, H-1), 4.64 (t, J=3.9 Hz, 1H, H-2), 4.56 (s, 2H, CH$_2$Ph), 4.14 (dt, J=8.5, 3.2 Hz, 1H, H-4), 3.91-3.71 (m, 2H, H-3, CH$_2$CH$_2$), 3.76-3.64 (m, 4H, H—, CH$_2$CH$_2$, CH$_2$CH$_2$, H-5), 3.32 (dd, J=13.5, 4.0 Hz, 1H, H-5), 1.57 (s, 3H, CH$_3$), 1.35 (s, 3H, CH$_3$); $^{13}$C NMR (101 MHz, CDCl$_3$): δ 138.0 (ArC), 128.4 (ArC), 127.7 (ArC), 113.2(C(CH$_3$)$_2$), 103.9 (C-1), 79.5 (C-3), 77.4 (C-4), 77.3 (C-2), 73.3 (CH$_2$Ph), 70.1 (CH$_2$CH$_2$), 69.7 (CH$_2$CH$_2$), 50.6 (C-5), 26.8(CH$_3$), 26.5(CH$_3$).; ESI-HRMS: m/z calcd. for C$_{17}$H$_{23}$N$_3$NaO$_5$ [M+Na]$^+$ 372.1535; found, 372.1538.

5-Benzyloxycarbonylamino-5-deoxy-3-O-(2-hydroxyethyl)-1,2-O-isopropylidene-α-D-ribofuranose (N). To a solution of compound (M) (3.0 g, 8.6 mmol) in dioxane: water=5:1 (30 mL), 20% Pd(OH)$_2$/C (3.0 g, 0.5 equiv) was added and the reaction mixture stirred at room temperature under 50 psi of hydrogen for 18 h. After completion, the reaction mixture was filtered over Celite®, concentrated to dryness and dissolved in dioxane:water=3:1 (50 mL). K$_2$CO$_3$ (6.0 g, 43.5 mmol) and benzyloxy chloroformate (2.5 mL, 17.2 mmol) were added and the reaction was stirred for 4 h. After completion, the reaction mixture was concentrated and purified using silica gel column chromatography (eluent: 0.8% to 1% methanol/DCM) to give N (1.67 g, 53%) as a colorless oil; $[\alpha]_D^{25}$=+35.47 (c 1.5, DCM); $^1$H NMR (400 MHz, CDCl$_3$): δ 7.41-7.28 (m, 5H, ArI-1), 5.73 (d, J=3.8 Hz, 1H, H-1), 5.10 (d, J=1.4 Hz, 2H (CH$_2$Ph), 4.60 (t, J=4.1 Hz, 1H, H-2), 4.03 (dt, J=9.0, 3.6 Hz, 1H, H-4), 3.77-3.61 (m, 5H, CH$_2$CH$_2$, CH$_2$CH$_2$, H-5), 3.55 (dd, J=9.0, 4.4 Hz, 1H, H-3), 3.45 (dt, J=14.6, 4.2 Hz, 1H, H-5), 3.04 (t, J=5.8 Hz, 1H, OH), 1.56 (s, 3H, CH$_3$), 1.35 (s, 3H, CH$_3$);$^{13}$C NMR (101 MHz, CDCl$_3$): δ 156.9 (C=O), 136.3 (ArC), 128.5 (ArC), 128.2 (ArC), 113.1(C (CH$_3$)$_2$), 104.1 (C-1), 79.3 (C-3), 77.1 (C-2), 77.0 (C-4), 72.0 (CH$_2$CH$_2$), 67.0 (CH$_2$Ph), 61.6 (CH$_2$CH$_2$), 40.6 (C-5), 26.6 (CH$_3$), 26.5 (CH$_3$); ESI-HRMS: m/z calcd. for C$_{18}$H$_{25}$NNaO$_7$ [M+Na]$^+$ 390.1529; found, 390.1537.

3-O-(2-Azidoethyl)-5-benzyloxycarbonylamino-5-deoxy-1,2-O-isopropylidene-α-D-ribofuranose (O). To a stirred solution of the alcohol N (1.0 g, 2.7 mmol) in dry THF (5 mL), triethylamine (2.8 mL, 20.4 mmol). The reaction mixture was ice-cooled before addition of p-tolylsulfonyl chloride (975 mg, 5.13 mmol) in dry THF (5 mL). The reaction mixture was stirred at 30° C. for 48 h before it was concentrated in vacuo. The crude product was dissolved in EtOAc and washed with aqueous NaHCO$_3$ and brine, dried over Na$_2$SO$_4$, and concentrated. The resulted solid was dissolved in dry DMF (10 mL) and treated with NaN$_3$ (1.05 g, 16.3 mmol) and stirred at 40° C. for 48 h. After completion, the reaction mixture was diluted with acetone and excess NaN$_3$ was filtered off. The solvent was partially removed under vacuum and the residue was diluted with EtOAc, washed with brine, dried over Na$_2$SO$_4$, and filtered. The solvent was removed under vacuum and the resulting product was purified using silica gel column chromatography (eluent: 10% to 25% EtOAc/hexanes) to give O (900 mg, 84% over two steps) as a viscous oil; $[\alpha]_D^{25}$=+35.38 (c 1.9, DCM); $^1$H NMR (400 MHz, CDCl$_3$): δ 739-7.27 (m, 5H, ArI-1), 5.73 (d, J=3.7 Hz, 1H, H-1), 5.10 (s, 2H, CH$_2$Ph), 4.60 (t, J=4.1 Hz, 1H, H-2), 4.05 (dt, J=8.6, 4.1 Hz, 1H, H-4), 3.82 (ddd, J=10.1, 6.0, 3.8 Hz, 1H, CH$_2$O), 3.67 (ddd, J=10.3, 6.5, 3.9 Hz, 1H, CH$_2$O), 3.63-3.47 (m, 3H, H-3, H-5), 3.47-3.32 (m, 2H, CH$_2$N$_3$), 1.56 (s, 3H, CH$_3$), 1.34 (s, 3H, CH$_3$);$^{13}$C NMR (101 MHz, CDCl$_3$): δ 156.5 (C=O), 136.4 (ArC), 128.5 (ArC), 128.1 (ArC), 113.3(C(CH$_3$)$_2$), 104.1 (C-1), 80.0 (C-3), 77.1 (C-2), 77.0 (C-4), 69.4 (CH$_2$O), 66.9 (CH$_2$Ph), 50.7 (CH$_2$N$_3$), 41.1 (C-5), 26.7 (CH$_3$), 26.6 (CH$_3$); ESI-HRMS: m/z calcd. for C$_{18}$H$_{24}$N$_4$NaO$_6$ [M+Na]$^+$415.1594; found, 415.1589.

3-O-(2-Azidoethyl)-5-di(benzyloxycarbonyl)amino-5-deoxy-1,2-O-isopropylidene-α-D-ribofuranose (P)

A stirred solution of the compound O (200 mg, 0.51 mmol) in dry THF (8 mL) and HMPA (2 mL), was cooled to -78° C. under argon before KHMDS (0.5 M in toluene, 1.5 mL, 0.66 mmol) and benzyloxychloroformate (0.3 mL, 2.1 mmol) were added. The reaction mixture was stirred at -78° C. for 2 h before additional KHMDS (0.5 M in toluene, 3 mL, 1.5 mmol) was added. The reaction was stirred for 30 min and quenched with NH$_4$Cl, diluted with EtOAc, and washed with aqueous NaHCO$_3$ and brine. The organic layer was dried over Na$_2$SO$_4$ and concentrated. The crude product was purified using silica gel column chromatography (eluent: 10% to 25% EtOAc/hexanes) to give P (272 mg, quant) [α]$_D^{25}$=+14.73 (c 1.5, DCM); $^1$H NMR (400 MHz, CDCl$_3$): δ 7.48-7.28 (m, 10H, ArH), 5.70 (d, J=3.8 Hz, 1H, H-1), 5.42-5.12 (m, 4H, CH$_2$Ph), 4.56 (t, J=4.1 Hz, 1H, H-2), 4.20 (dt, J=8.9, 5.4 Hz, 1H, H-4), 4.07 (dd, J=5.4, 1.2 Hz, 2H, H-5), 3.72 (ddd, J=9.9, 6.0, 4.0 Hz, 1H, CH$_2$O), 3.57 (dd, J=8.8, 4.4 Hz, 1H, H-3), 3.45 (ddd, J=10.1, 6.3, 4.2 Hz, 1H, CH$_2$O), 3.34-3.16 (m, 2H, CH$_2$N$_3$), 1.51 (s, 3H, CH$_3$), 1.33 (s, 3H, CH$_3$); $^{13}$C NMR (101 MHz, CDCl$_3$): δ 153.6 (C=O), 135.2 (ArC), 128.5 (ArC), 128.3 (ArC), 128.2 (ArC), 128.1 (ArC), 113.1(C(CH$_3$)$_2$), 104.2 (C-1), 81.3 (C-3), 77.4 (C-2), 77.1 (C-4), 68.9 (CH$_2$O), 68.8 (CH$_2$Ph), 66.9 (CH$_2$Ph), 50.5 (CH$_2$N$_3$), 47.1 (C-5), 26.7 (201-1$_3$); ESI-HRMS: m/z calcd. for C$_{26}$H$_{30}$N$_4$NaO$_8$ [M+Na]$^+$ 549.1961; found, 549.1962.

3-O-(2-Azidoethyl)-5-di(benzyloxycarbonyl)amino-5-deoxy-1,2-di-O-(p-nitrobenzoyl)-α/β-D-ribofuranose (Q). To a stirred solution of compound P (268 mg, 0.51 mmol) in dioxane (10 mL), 1 N HCl (4 mL) was added and the reaction mixture was heated at 80° C. for 2 h. The reaction mixture was cooled, neutralized with solid NaHCO$_3$ and the solvent was evaporated. The residue was dissolved in EtOAc and washed with water and brine, dried with Na$_2$SO$_4$ and evaporated. To a solution of the crude mixture in dry pyridine (10 mL), p-nitrobenzoyl chloride (672 mg, 3.6 mmol) and a catalytic amount of DMAP were added followed by stirring overnight. The reaction mixture was diluted with EtOAc and washed with NaHCO$_3$, brine, dried with Na$_2$SO$_4$ then concentrated. The crude product was purified using silica gel column chromatography (eluent: 15%-40% EtOAc/hexanes) to give the α isomer (235 mg, 59%) as a white solid and the β isomer (165 mg, 41%) as a white solid; α isomer: [α]$_D^{25}$=+13.85 (c 0.4, DCM); $^1$H NMR (400 MHz, CDCl$_3$): δ 8.31-8.17 (m, 6H, ArH), 8.12 (d, J=8.8 Hz, 2H, ArH), 7.48-7.17 (m, 10H, ArH), 6.64 (d, J=4.4 Hz, 1H, H-1), 5.36 (dd, J=6.6, 4.4 Hz, 1H, H-2), 5.34-5.21 (m, 4H, 2*CH$_2$Ph), 4.61 (td, J=6.2, 3.8 Hz, 1H, H-4), 4.18 (dd, J=6.6, 3.8 Hz, 1H, H-3), 4.15-3.99 (m, 2H, H-5), 3.47 (t, J=4.8 Hz, 2H, CH$_2$CH$_2$O), 3.20-3.12 (m, 2H, CH$_2$N$_3$). $^{13}$C NMR (101 MHz, CDCl$_3$): δ 163.6 (C=O), 163.3 (C=O), 153.5 (C=O), 150.9 (ArC), 150.8 (ArC), 148.4 (ArC), 137.3 (ArC), 134.9 (ArC), 134.8 (ArC), 134.1 (ArC), 131.0 (ArC), 130.9 (ArC), 130.8 (ArC), 128.6 (ArC), 128.4 (ArC), 123.7 (ArC), 123.4 (ArC), 95.4 (C-1), 82.6 (C-4), 77.3 (C-3), 72.4 (C-2), 70.1 (CH$_2$CH$_2$O), 69.3 (CH$_2$Ph), 50.9 (CH$_2$N$_3$), 47.7 (C-5); ESI-HRMS: m/z calcd. for C$_{37}$H$_{32}$N$_6$NaO$_{14}$ [M+Na]$^+$ 807.1874; found, 807.1852; β isomer: [α]$_D^{25}$=−32.63 (c 0.5, DCM); $^1$H NMR (400 MHz, CDCl$_3$): δ 8.53-7.91 (m, 8H, ArH), 7.29 (s, 10H, ArH), 6.52 (s, 1H, H-1), 5.71 (d, J=4.1 Hz, 1H, H-2), 5.19 (q, J=12.3 Hz, 4H, 2*CH$_2$Ph), 4.46 (dt, J=8.1, 4.9 Hz, 1H, H-4), 4.39 (dd, J=8.0, 4.2 Hz, 1H, H-3), 4.30-4.14 (m, 2H, H-5), 3.73 (ddd, J=9.9, 6.8, 3.3 Hz, 1H, CH$_2$CH$_2$O), 3.57 (ddd, J=9.5, 6.0, 3.3 Hz, 1H, CH$_2$O), 3.30-3.04 (m, 2H, CH$_2$N$_3$); $^{13}$C NMR (101 MHz, CDCl$_3$): δ 163.5 (C=O), 162.9 (C=O), 153.9 (C=O), 150.9 (ArC), 150.7 (ArC), 134.9 (ArC), 134.4 (ArC), 134.3 (ArC), 131.1 (ArC), 131.0 (ArC), 128.6 (ArC), 128.5 (ArC), 128.2 (ArC), 128.1 (ArC), 123.7 (ArC), 123.6 (ArC), 99.6 (C-1), 80.2 (C-4), 79.2 (C-3), 74.5 (C-2), 70.4 (CH$_2$CH$_2$O), 69.2 (CH$_2$Ph), 50.6 (CH$_2$N$_3$), 47.2 (C-5); ESI-HRMS: m/z calcd. for C$_{37}$H$_{32}$N$_6$NaO$_{14}$ [M+Na]$^+$ 807.1874; found, 807.1877.

5-O-β-[3-O-(2-Azidoethyl)-5-di(benzyloxycarbonyl) amino-5-deoxy-2-O-p-nitrobenzoyl-D-ribofuranose]-6,2", 3",6"-tetra-O-acetyl-1,3,2',4"-tetraazido-6',7'-oxazolidino-apramycin (R). Donor Q (β isomer, 165 mg, 0.21 mmol), acceptor A (440 mg, 0.52 mmol) and activated 4 A MS were stirred in dry DCM (3 mL) at rt for 1 h before cooling to 0° C. BF$_3$.OEt$_2$ (300 uL, 0.78 mmol) was added and reaction mixture was stirred for 48 h at 0° C. The reaction was quenched with triethylamine (0.5 mL) and filtered through Celite® before it was diluted with EtOAc. The organic layer was washed with aqueous NaHCO$_3$ and brine then concentrated. The crude product was purified using silica gel column chromatography (eluent: 0.6%-1.5°/O Methanol/DCM) to give the glycoside R (136 mg, 45%) as the β anomer in the form of a white solid; [α]$_D^{25}$=+46.26 (c 0.9, DCM); $^1$H NMR (600 MHz, CDCl$_3$): δ 8.29-8.21 (m, 2H, ArH), 8.19-8.09 (m, 2H, ArH), 7.39-7.32 (m, 4H, ArH), 7.32-7.25 (m, 6H, ArH), 5.43-5.35 (m, 3H, H-1', H-3", H-1"'), 5.32 (d, J=3.9 Hz, 1H, H-1"''), 5.31-5.26 (m, 4H, 2*CH$_2$Ph), 5.25 (d, J=4.1 Hz, 1H, H-2'''), 4.89 (dd, J=10.3, 3.9 Hz, 1H, H-2"), 4.87 (d, J=3.4 Hz, 1H, H-8'), 4.84 (t, J=9.8 Hz, 1H, H-6), 4.78 (dd, J=8.2, 3.2 Hz, 1H, H-6'), 4.60 (dd, J=10.5, 3.2 Hz, 1H, H-5'), 4.31 (dd, J=12.3, 2.3 Hz, 1H, H-6"), 4.28-4.18 (m, 2H, H-6", H-4"''), 4.18-4.10 (m, 2H, H-5"''), 4.08 (dd, J=7.8, 4.5 Hz, 1H, H-3"''), 3.79 (dd, J=8.2, 3.5 Hz, 1H, H-7'), 3.71 (ddd, J=10.7, 5.3, 2.3 Hz, 1H, H-5"), 3.66 (td, J=10.9, 4.3 Hz, 1H, H-4'), 3.63-3.52 (m, 4H, H-3, H-5, H-4", CH$_2$CH$_2$O), 3.49-3.43 (m, 2H, H-4, CH$_2$CH$_2$O), 3.39 (ddd, J=12.5, 10.2, 4.2 Hz, 1H, H-1), 3.27 (dt, J=12.8, 4.3 Hz, 1H, H-2'), 3.12 (ddd, J=13.3, 7.3, 3.2 Hz, 1H, CH$_2$N$_3$), 3.02 (ddd, J=13.3, 5.7, 3.2 Hz, 1H, CH$_2$N$_3$), 2.92 (s, 3H, NCH$_3$), 2.38 (dt, J=12.9, 4.5 Hz, 1H, H-2), 2.20 (s, 3H, COCH$_3$), 2.17-2.11 (m, 1H, H-3'), 2.08 (d, J=4.4 Hz, 6H, 2*COCH$_3$), 2.04 (s, 3H, COCH$_3$), 1.77 (q, J=11.8 Hz, 1H, H-3'), 1.41 (q, J=12.6 Hz, 1H, H-2); $^{13}$C NMR (151 MHz, CDCl$_3$): δ 170.3 (C=O), 170.0 (C=O), 169.9 (C=O), 169.4 (C=O), 163.9 (C=O), 157.0 (ArC), 153.7 (ArC), 150.8 (ArC), 135.3 (ArC), 134.4 (ArC), 130.9 (ArC), 128.5 (ArC), 128.2 (ArC), 127.9 (ArC), 123.7 (ArC), 106.7 (C-1"''), 96.8 (C-1'), 95.4 (C-8'), 94.0 (C-1"), 80.4 (C-5), 79.5 (C-3"''), 79.3 (C-4), 79.1 (C-4"''), 74.8 (C-2"''), 74.3 (C-6), 70.6 (C-3"), 70.3 (C-6'), 70.0 (CH$_2$CH$_2$O), 69.9 (C-2"''), 68.9 (2*CH$_2$Ph), 65.6 (C-5'), 65.3 (C-4'), 62.9 (C-6"), 60.14 (C-7'), 60.11 (C-4"), 58.3 (C-3), 58.1 (C-1), 57.4 (C-2'), 50.6 (CH$_2$N$_3$), 48.2 (C-5"''), 31.3 (C-3'), 31.0 (C-2), 29.9 (NCH$_3$), 21.0 (COCH$_3$), 20.9 (COCH$_3$), 20.8 (COCH$_3$), 20.7 (COCH$_3$); ESI-HRMS: m/z calcd. for C$_{60}$H$_{66}$N$_{18}$NaO$_{26}$ [M+Na]$^+$ 1477.4293; found, 1477.4232.

5-O-β-[5-Amino-3-O-(2-aminoethyl)-5-deoxy-D-ribofuranosyl] apramycin heptaacetate salt (DCWSU185) A stirred solution of substrate R (67 mg, 0.046 mmol) in dioxane (1.5 mL) was treated with 3 N NaOH (1.5 mL) and heated at 100° C. for 18 h. The reaction mixture was cooled to 0° C. and neutralized with glacial acetic acid before it was concentrated in vacuo. The crude mixture was passed through a silica gel column (eluent: 25% methanol/DCM). The resulting solid (20 mg, 0.023 mmol) was dissolved in a water methanol:water mixture (1:1, 0.5 mL) and treated with N-(diethylcarbamoyl)-N-methoxyformamide (30 μL, 0.17 mmol) and triethylamine (2 μL). The reaction mixture was stirred for 2 h and quenched with aqueous ammonium hydroxide (0.25 mL) and concentrated. The crude product was purified using silica gel column chromatography (eluent: 5% to 15% ammonical MeOH in DCM). A part of the solid residue (12 mg, 0.014 mmol) dissolved in dioxane (3 mL) followed by the addition of 1 N NaOH (0.5 mL) and 1 M P(CH$_3$)$_3$ in THF (0.2 mL), and stirred at 50° C. for 45 min. The reaction mixture was then concentrated to dryness and dissolved in aqueous acetic acid (pH 4, 1 mL) before it was charged to a Sephadex column (CM Sephadex C-25). The column was flushed with D.I. water (20 mL), then gradient eluted of 0.1%-1.0% $NH_4OH$ in D.I. water. The fractions containing the products were combined, acidified with glacial acetic acid and lyophilized to afford the peracetate salt of DCWSU185 in (14.5 mg, 56%) as a white solid; $[\alpha]_D^{25}$=+72.53 (c 0.7, $H_2O$); $^1$H NMR (600 MHz, $D_2O$): δ 5.73 (d, J=4.0 Hz, 1H, H-1'), 5.31 (d, J=3.7 Hz, 1H, H-1"), 5.26 (s, 1H, H-1'''), 5.03 (d, J=8.6, 1H, H-8'), 4.40 (s, 1H, H-6'), 4.26 (d, J=4.4 Hz, 1H, H-2'''), 4.03 (td, J=7.5, 3.8 Hz, 1H, H-4'''), 3.93-3.86 (m, 2H, H-4, H-3'''), 3.83-3.71 (m, 4H, H-5, H-4', H-3", H-5"), 3.69-3.57 (m, 4H, $CH_2CH_2O$, H-6"), 3.56-3.44 (m, 4H, H-6, H-2', H-5', H-2"), 3.35-3.26 (m, 1H, H-3), 3.23-3.11 (m, 3H, H-1, H-7', H-5"), 3.11-2.99 (m, 4H, H-4", H-5, $CH_2CH_2O$), 2.59 (s, 3H, $NCH_3$), 2.24 (dt, J=13.1, 4.4 Hz, 1H, H-2), 2.20 (dt, J=10.1, 4.7 Hz, 1H, H-3'), 1.93-1.83 (m, 1H, H-3'), 1.68-1.59 (m, 1H, H-2); $^{13}$C NMR (151 MHz, $D_2O$): δ 108.9 (C-1'''), 94.4 (C-1'), 92.7 (C-1"), 92.5 (C-8'), 83.2 (C-5), 79.2 (C-3"), 77.0 (C-4'''), 73.6 (C-4), 72.7 (C-2"), 72.0 (C-6), 70.2 (C-2"), 69.5 (C-5", C-5'), 68.3 (C-3"), 65.9 (C-4'), 65.8 ($CH_2CH_2O$), 62.6 (C-6'), 60.2 (C-6"), 59.5 (C-7'), 52.0 (C-4"), 50.0 (C-1), 48.7 (C-3), 47.6 (C-2'), 42.1 (C-5'''), 39.2 ($CH_2CH_2O$), 30.0 ($NCH_3$), 28.2 (C-2), 27.0 (C-3'); ESI-HRMS: m/z calcd. for $C_{28}H_{56}N_7O_{14}$ $[M+H]^+$ 714.3885; found, 714.3868.

5-β-[3-O-(2-Aminoethyl)-5-deoxy-5-formamido-D-ribofuranosyl] apramycin hexaacetate salt (DCWSU186). A stirred solution of substrate R (67 mg, 0.046 mmol) in dioxane (1.5 mL) was treated with 3 N NaOH (1.5 mL) and heated at 100° C. for 18 h. The reaction mixture was cooled to 0° C. and neutralized with glacial acetic acid before it was concentrated in vacuo. The crude mixture was passed through a silica gel column (eluent: 25% methanol/DCM). The resulting solid (20 mg, 0.023 mmol) was dissolved in a water methanol:water mixture (1:1, 0.5 mL) and treated with N-(diethylcarbamoyl)-N-methoxyformamide (30 μL, 0.17 mmol) and triethylamine (2 μL). The reaction mixture was stirred for 2 h and quenched with aqueous ammonium hydroxide (0.25 mL) and concentrated. The crude product was purified using silica gel column chromatography (eluent: 5% to 15% ammonical MeOH in DCM). A part of the solid residue (20 mg, 0.022 mmol) was dissolved in dioxane: water (1:1, 0.6 mL) followed by the addition 1 M $P(CH_3)_3$ in THF (0.3 mL), and stirred at 50° C. for 45 min. The reaction mixture was then concentrated to dryness and dissolved in aqueous acetic acid solution (pH 4, 1 mL) before it was charged to a Sephadex column (CM Sephadex C-25). The column was flushed with D.I. water (20 mL), then gradient elution of 0.1%-1.0% $NH_4OH$ in D.I. water. The fractions containing the product were combined, acidified with acetic acid, and lyophilized to afford the peracetate salt of DCWSU186 in (13.9 mg, 57%) as a white solid; $[\alpha]_D^{25}$=+55.35 (c 0.2, $H_2O$); $^1$H NMR (600 MHz, $D_2O$): δ 7.94 (s, 1H, CHO), 5.69 (d, J=3.9 Hz, 1H, H-1'), 5.30 (d, J=4.0 Hz, 1H, H-1"), 5.15 (d, J=3.0 Hz, 1H, H-1'''), 5.03 (d, J=8.6 Hz, 1H, H-8'), 4.40 (t, J=2.7 Hz, 1H, H-6'), 4.16 (dd, J=4,9,3,0 Hz, 1H, H-2'''), 3.97 (q, J=5.6 Hz, 1H, H-4'''), 3.88 (t, J=9.6 Hz, 1H, H-4), 3.83-3.68 (m, 5H, H-5, H-4', H-3", H-5", H-3'''), 3.68-3.55 (m, 4H, H-6", $CH_2CH_2O$), 3.54-3.44 (m, 4H, H-6, H-2', H-5', H-2"), 3.40 (dd, J=14.5, 4.6 Hz, 1H, H-5'''), 3.33 (ddd, J=14.3, 10.4, 4.3 Hz, 1H, H-3), 3.29 (dd, J=14.5, 6.1 Hz, 1H, H-5'''), 3.20 (dd, J=8.6, 2.8 Hz, 1H, H-7'), 3.18-3.12 (m, 1H, H-1), 3.10 (t, J=10.3 Hz, 1H, H-4"), 3.05-2.98 (m, 2H, $CH_2CH_2O$), 2.59 (s, 3H, $NCH_3$), 2.28 (dt, J=12.6, 4.3 Hz, 1H, H-2), 2.18 (dt, J=11.2, 4.6 Hz, 1H, H-3'), 1.88 (d, J=11.8 Hz, 1H, H-3'), 1.72-1.63 (m, 1H, H-2); $^{13}$C NMR (151 MHz, $D_2O$): δ 164.8 (CHO), 110.3 (C-1'''), 94.4 (C-1'), 93.6 (C-1"), 92.8 (C-8'), 84.8 (C-5), 79.3 (C-4'''), 78.8 (C-3"), 74.8 (C-4), 73.1 (C-2'''), 72.3 (C-6), 70.2 (C-2"), 69.7 (C-5"), 69.3 (C-5'), 68.2 (C-3"), 65.9 (C-4'), 65.8 ($CH_2CH_2O$), 62.6 (C-6'), 60.2 (C-6"), 59.3 (C-7'), 52.0 (C-4"), 49.6 (C-1), 48.5 (C-3), 47.6 (C-2'), 40.1 (C-5'''), 39.2 ($CH_2CH_2O$), 30.0 ($NCH_3$), 27.9 (C-2), 26.7 (C-3'); ESI-HRMS: m/z calcd. for $C_{29}H_{56}N_7O_{15}$ $[M+H]^+$ 742.3834; found, 742.3861.

Example 12

Key Intermediate A

Figure 17:
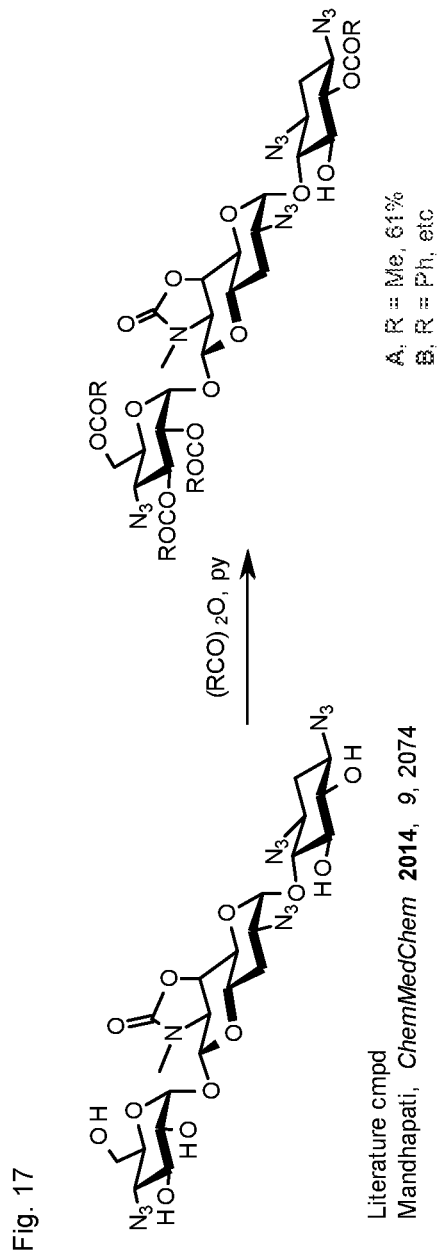
FIG. 17 shows the synthesis of key intermediate compound 5-OH apramycin.

See the synthetic scheme of FIG. 17.

6,2",3",6"-Tetra-O-acetyl-1,3,2',4"-tetraazido-6',7'-oxazolidino-apramycin (A). A stirred solution of 1,3,2',4"-tetraazido-6',7'-oxazolidino-apramycin (100 mg, 0.15 mmol) in dry pyridine (0.3 mL) was cooled to 0° C. and treated with acetic anhydride (60 μL, 0.62 mmol). The reaction mixture was allowed to warm up to rt and stirred overnight. The reaction progress was monitored by TLC and additional acetic anhydride (0.5-1 equiv) was added as needed. After completion, the reaction mixture was diluted with EtOAc and the organic layer was washed with aqueous $NaHCO_3$ followed by brine, dried with $Na_2SO_4$, and concentrated. The crude product was purified via silica gel chromatography eluting with 0.6% to 0.8% methanol in DCM to give A (76 mg, 61%) as a white solid; $[\alpha]_D^{25}$=+101.6 (c 3.1, DCM); $^1$H NMR (600 MHz, $CDCl_3$): δ 5.35 (t, J=9.9 Hz, 1H, H-3"), 5.30 (d, J=3.7 Hz, 1H, H-1"), 5.15 (d, J=3.5 Hz, 1H, H-1'), 4.93 (d, J=2.9 Hz, 1H, H-8'), 4.93-4.87 (m, 2H, H-6, H-2"), 4.81 (dd, J=8.6, 3.2 Hz, 1H, H-6'), 4.61 (dd, J=10.5, 3.2 Hz, 1H, H-5'), 4.31 (dd, J=12.3, 2.2 Hz, 1H, H-6"), 4.20 (dd, J=12.3, 5.1 Hz, 1H, H-6"), 3.84 (dd, J=8.7, 3.0 Hz, 1H, H-7), 3.80 (dt, J=10.9, 5.5 Hz, 1H, H-4'), 3.72 (ddd, J=10.7, 5.1, 2.3 Hz, 1H, H-5"), 3.66 (ddd, J=12.3, 9.9, 4.7 Hz, 1H, H-3), 3.62-3.53 (m, 3H, H-2', H-4", H-5), 3.49 (ddd, J=12.5, 10.0, 4.5 Hz, 1H, H-1), 3.45 (t, J=9.5 Hz, 1H, H-4), 2.89 (s, 3H, $NCH_3$), 2.41 (dt, J=13.3, 4.6 Hz, 1H, H-2), 2.29 (dt, J=10.9, 4.5 Hz, 1H, H-3), 2.13 (s, 3H, $COCH_3$), 2.10 (s, 3H, $COCH_3$), 2.10 (s, 3H, $COCH_3$), 2.07 (s, 3H, $COCH_3$), 1.89 (q, J=11.7 Hz, 1H, H-3), 1.60 (q, J=12.7 Hz, 1H, H-2); $^{13}$C NMR (151 MHz, $CDCl_3$): δ 170.37 (C=O), 170.34 (C=O), 169.91 (C=O), 169.88 (C=O), 157.0 (NC=O), 98.8 (C-1'), 94.9 (C-8), 94.5 (C-1"), 83.8 (C-4), 74.9 (C-6), 74.3 (C-5), 70.7 (C-3"), 70.1 (C-2"), 69.8 (C-6), 68.8 (C-5"), 65.5 (C-5), 65.1 (C-4), 62.8 (C-6"), 60.1 (C-2'), 59.9 (C-7'), 58.4 (C-3), 58.0 (C-1), 57.6 (C-4"), 32.0 (C-2), 30.6 (C-3), 29.8 (C—$NCH_3$), 20.9 ($COCH_3$), 20.7 ($COCH_3$); ESI-HRMS: m/z calcd. for $C_{30}H_{39}N_{13}NaO_{16}$ $[M+Na]^+$ 860.2535; found, 860.2522.

TABLE 1

O5-ribosylated apramycin derivatives

| Compound | 3''' | 5''' | MIC (μg/mL) | | | | | | IC50 (μM) | | |
|---|---|---|---|---|---|---|---|---|---|---|---|
| | | | WT | AAC(3)-IV | APH(3')-I | APH(3')-II | APH(3')-III | APH(3')-VI | Bac | Mit | Cyt |
| apramycin | — | — | 2-4 | >128 | 1-2 | 4 | 1 | 4 | 0.08 | 68 | 71 |
| DC146 | OH | — | 8 | 32 | 4 | 4 | 1 | 8 | 0.09 | 215 | 321 |
| DC131 | OH | OH | 4 | >32 | 64 | 8 | 4 | 4 | 0.11 | 295 | 319 |
| DC177 | OH | Form. | 8 | >32 | 4 | 8 | 2 | 8 | 0.23 | 399 | >500 |
| DC201 | OH | NH2 | 8 | 16 | 2-4 | 4 | 1 | 4 | 0.12 | 113 | 81 |
| DC214 | OH | N-NH2-ethyl | 4 | 8-16 | 2 | 4 | 1 | 4 | 0.09 | 178 | 85 |
| DC178 | OH-ethyl | OH | 8 | >32 | >64 | 8 | 2 | 16 | 0.22 | 647 | >500 |
| DC124 | NH2-ethyl | OH | 2 | >32 | 64 | 2 | 0.5 | 4 | 0.06 | 57 | 181 |
| DC185 | NH2-ethyl | NH2 | 1 | >32 | 1 | 1 | 0.25 | 2 | 0.03 | 34 | 26 |
| DC186 | NH2-ethyl | Form | 2 | >32 | 2 | 2 | 0.25 | 2 | 0.06 | 69 | 105 |
| DC138 | ring | OH | 2 | >32 | 16 | 2 | 1-2 | 4 | 0.10 | 2.2 | 18 |
| paromomycin | ring | OH | 1-2 | 128 | >128 | >128 | >128 | >128 | 0.02 | 86 | 19 |

Legend to Tables: GEN, gentamicin; AMK, amikacin; PLZ, plazomicin; APR, apramycin; AG212, Escherichia coli ATCC25922; AG215, Klebsiella pneumonia; AG220, Pseudomonas aeruginosa ATCC27853; AG225, Acinetobacter baumannii pittii; AG290, Enterobacter cloacae; AG192, SZ380, Mycobacterium smegmatis. MICs for AG192 have been determined in the presence of 0.5 μg/mL of ampicillin in the medium to mimic the synergistic effect of aminoglycoside and β-lactam antibiotics combination therapy in the treatment of Enterococcus infections in humans.

TABLE 2

5-modified apramycin derivatives

| Compound | Modification | MIC (μg/mL) | | | IC50 (μM) | | |
|---|---|---|---|---|---|---|---|
| | | WT | AAC(3)-IV | apmA | Bac | Mit | Cyt |
| Apramycin | — | 2-4 | >128 | 64 | 0.08 | 68 | 71 |
| DC176 | 1-N-LHABA | 2 | 4 | 16 | 0.11 | 166 | 326 |
| DC169 | 5-deoxy | 4 | >32 | 16 | 0.06 | 45 | 42 |
| DC161 | 5-epi | 2 | >32 | 2 | 0.05 | 20 | 17 |
| DC191 | 5-epi-1-N-LHABA | 2-4 | 4-8 | 8 | 0.20 | 98 | 87 |
| DC170 | 5-deoxy-5-F | 4 | >32 | 32 | 0.06 | 62 | 74 |
| DC168 | 5-deoxy-5-F epi | 2 | >32 | 4 | 0.05 | 30 | 28 |
| DC167 | 6-O-(2OH-ethyl) | 8 | >32 | >64 | 0.18 | 379 | 382 |
| DC207 | 5-O-(3-hydroxypropyl) | 8 | >128 | >128 | 0.60 | >1000 | >1000 |
| DC213 | 5-O-(3-aminopropyl) | 4 | 64 | 64-128 | 0.21 | 327 | 210 |
| DC208 | 5-O-(2,3-dihydroxypropyl) | 4-8 | 64 | >128 | 0.21 | 434 | >1000 |
| DC209 | 5-O-(3-amino-2-hydroxypropyl) | 2-4 | 8 | 64-128 | 0.04 | 146 | 105 |
| DC212 | 5-O-(3-amino-2-hydroxypropyl) | 4 | | | 0.10 | 158 | 112 |

TABLE 3

6-modified apramycin derivatives

| Compound | Modification | MIC (μg/mL) | | | IC50 (μM) | | |
|---|---|---|---|---|---|---|---|
| | | WT | AAC(3)-IV | apmA | Bac | Mit | Cyt |
| Apramycin | — | 2-4 | >128 | 64 | 0.08 | 68 | 71 |
| DC167 | 6-O-(2OH-ethyl) | 8 | >32 | >64 | 0.18 | 379 | 382 |

TABLE 4

Antibiotic potency against bacterial reference strains

| | MIC (μg/mL) | | | | | | | Disk diffusion |
|---|---|---|---|---|---|---|---|---|
| | AG212 E. coli | AG215 K. pneumonia | AG290 E. cloacae | AG220 P. aeruginosa | AG225 A. baumannii | SZ380 M. smegmatis | ATCC19977 M. abcessus | 25 nmol N. gonorrhoeae |
| GEN | 0.5 | 0.25 | 0.25 | 0.5-1 | 0.5-1 | | 2-4 | |
| AMK | 2 | 1 | 1 | 2 | 2 | | 2 | |

TABLE 4-continued

Antibiotic potency against bacterial reference strains

| | MIC (μg/mL) | | | | | | | Disk diffusion |
| --- | --- | --- | --- | --- | --- | --- | --- | --- |
| | AG212 E. coli | AG215 K. pneumonia | AG290 E. cloacae | AG220 P. aeruginosa | AG225 A. baumannii | SZ380 M. smegmatis | ATCC19977 M. abcessus | 25 nmol N. gonorrhoeae |
| PLZ | 0.5-1 | 0.25-0.5 | 0.5 | 2-4 | 2 | | 4 | |
| APR | 4 | 2 | 4 | 4 | 4 | | 2 | <8 mm |
| DC146 | 16 | 4 | 4 | 32 | 8 | | 4 | |
| DC131 | 8 | 2 | 4 | 64 | 16 | | 16 | |
| DC177 | 8 | 4 | 8 | >64 | 16 | 2 | 16 | |
| DC201 | 4 | 2 | 2 | 4-8 | 4-8 | 0.25 | 1-2 | |
| DC214 | 2 | 1 | 1-2 | 8 | 8 | 0.25 | 2 | |
| DC178 | 8 | 4 | 8 | >64 | 16 | 2 | 32 | |
| DC124 | 2 | 1-2 | 1-2 | 16-32 | 8 | | 8 | |
| DC185 | 2 | 0.5-1 | 1 | 1-2 | 2 | | 1 | |
| DC186 | 2-4 | 1 | 1-2 | 16-32 | 8 | | 8 | |
| DC138 | 2 | 1 | 2 | 16 | 4 | | 2 | |
| DC176 | 2-4 | 2 | 4 | 16 | 8 | 0.5 | 2 | |
| DC169 | 4 | 2 | 2 | 4 | 4 | 0.125 | 1 | |
| DC161 | 2 | 1 | 2 | 2 | 2 | | 0.5 | 10 mm |
| DC191 | 2 | 1-2 | 2 | 4 | 8 | 0.5 | 2 | |
| DC170 | 4 | 2 | 4 | 8 | 4-8 | 0.25 | 1 | |
| DC168 | 4 | 1 | 4 | 4 | 4 | 0.125 | 1 | |
| DC167 | 16 | 4 | 8 | 32 | 16 | | 2 | |
| DC207 | 16 | 8 | 16 | 64 | 32 | 1 | 8 | |
| DC213 | 4-8 | 2 | 4-8 | 8 | 8 | 0.25 | 1 | |
| DC208 | 8 | 4 | 4 | 16-32 | 16 | 0.5 | 2 | |
| DC209 | 2-4 | 1 | 1 | 2-4 | 4 | 0.125 | 0.5-1 | |
| DC212 | 4 | 2 | 4 | 4 | 4 | | | |

TABLE 5

Antibacterial activity against representative clinical isolates

| | AG001 E. coli WT | AG055 E. coli WT | AG003 E. coli AAC(3)-II | AG173 E. coli AAC(3)-IV | AG163 E. coli APH(3')-I | AG038 MRSA | AG039 MRSA AAC(6')-I ANT(4')-I | AG042 MRSA AAC(6')-I ANT(4')-I APH(2') | AG031 P. aer. APH(3')-II | AG032 P. aer. APH(3')-II | AG033 P. aer. APH(3')-II AAC(6')-I |
| --- | --- | --- | --- | --- | --- | --- | --- | --- | --- | --- | --- |
| GEN | 1 | 0.5 | 32-64 | | | 0.25-0.5 | 0.25-0.5 | 64 | 0.5 | 0.5 | 16 |
| AMK | | | | | | 4 | 2-4 | 16-32 | 4 | 4 | 64 |
| PLZ | 2-4 | 2-4 | 2-4 | | | 2-4 | 2-4 | 2 | 4 | 4 | 16-32 |
| APR | 8-16 | 8 | 8 | ≥128 | 4 | 4-8 | 8 | 8 | 8-16 | 8 | 16-32 |
| DC146 | 16 | 16 | 16 | 128 | 8 | 16-32 | 16-32 | 16 | 64 | 64 | 64-128 |
| DC131 | 16 | 16-32 | 16 | 16-32 | 8-16 | 64 | 64 | 64 | 64-128 | 64-128 | 128 |
| DC177 | 8 | 16 | 8 | >64 | 8 | 32 | 16-32 | 32 | >32 | >32 | >32 |
| DC201 | 4 | | | | | 2-4 | | | 16 | | |
| DC214 | 2 | | | 16 | | 4 | | | 8-16 | | |
| DC178 | 32 | 16 | 16 | 32-64 | 8 | 16-32 | 32 | 32 | >32 | >32 | >32 |
| DC124 | 8 | 8 | 4-8 | 4 | 4-8 | 8-16 | 8 | 8 | 32-64 | 32-64 | 128 |
| DC185 | 2 | 2 | 1-2 | 4 | 2 | 1 | 1 | 1 | 2 | 2 | 2 |
| DC186 | 2 | 4 | 2 | 32 | 2 | 4 | 4-8 | 4-8 | 16 | 32 | 64 |
| DC138 | 4 | 8 | 4 | 1-2 | 8 | 2-4 | 2-4 | 2 | 32-64 | 64 | 64 |
| DC176 | 4 | 8 | 4 | 2-4 | 4 | 4-8 | 4-8 | 8 | 16 | 32 | >32 |
| DC169 | 4 | 4 | 4 | 32 | | 2-4 | 2 | 4 | 8 | 8 | 16 |
| DC161 | 4 | 4 | 4-8 | 64 | | 4 | 4 | 2-4 | 4 | 4 | 8 |
| DC191 | 8 | | | 4-8 | | 4 | | | | | |
| DC170 | 8 | 4 | 8 | 64 | | 4-8 | 4-8 | 8 | 8-16 | 16 | 32 |
| DC168 | 8 | 4 | 4 | 128 | | 2-4 | 2-4 | 4 | 8-16 | 8-16 | 32 |
| DC167 | 16 | 16 | 16 | >128 | 8-16 | 16-32 | 16-32 | 64 | 32-64 | 32-64 | 64-128 |
| DC207 | 16 | | | >128 | | 32 | | | 128 | | |
| DC213 | 16 | | | 128 | | 4 | | | 16-32 | | |
| DC208 | 8 | | | >64 | | 8-16 | | | 32 | | |
| DC209 | 2 | | | 32 | 4 | 1-2 | | | 4 | | |
| DC212 | 8 | | | | | 4 | | | 8 | | |

TABLE 6

Activity against G1405-methylated 16S-rRNA

| | Engineered E. coli | | | | | | Clinical isolates | | | |
|---|---|---|---|---|---|---|---|---|---|---|
| | | | | | | | E. coli AG153 | K. pneum. AG269 | Enterob. AG302 | A baum. |
| | E. coli pH430 WT | E. coli AG103 armA | E. coli pH424 armA | E. coli pH425 rmtB | E. coli pH426 rmtC | E. coli pH427 rmtF | AAC(3)-II APH(3')-II rmtB | AAC(3)-II AAC(6')-I rmtB | AAC(3)-II AAC(6')-I rmtC | AG227 APH(3')-I armA |
| GEN | 0.25 | | >128 | >128 | >128 | >128 | >256 | >256 | >256 | >256 |
| AMK | 1 | | >128 | >128 | >128 | >128 | >256 | >256 | >256 | >256 |
| PLZ | 0.5 | >32 | | | | | | | | |
| APR | 2-4 | 1-2 | 2-4 | 4 | 4 | 4 | 8 | 2 | 4 | 2 |
| DC146 | 8 | 1 | 4 | 4 | 8 | 4 | | | | |
| DC131 | 4 | 1 | 2 | 4 | 4 | 4 | | | | |
| DC177 | 8 | 2-4 | 8 | 8 | 16 | 8 | | | | |
| DC201 | 8 | | 2 | | | | 8 | 4 | 4 | 8-16 |
| DC214 | 4 | | 2 | | | | 2 | 2 | 1-2 | 4-8 |
| DC178 | 8 | 2 | 2 | 8 | 8 | 8 | | | | |
| DC124 | 2 | 0.5 | 1 | 4 | 2 | 2 | 4 | 2 | 4 | 16 |
| DC185 | 1 | 0.5-1 | 2 | 2 | 2 | 2 | 4 | 1 | 1 | 2 |
| DC186 | 2 | 0.5-1 | 2 | 2 | 4 | 2 | | | | |
| DC138 | 2 | <0.125 | 1 | 1 | 1 | 1 | | | | |
| DC176 | 2 | 0.25-0.5 | 2 | 2 | 4 | 4 | 4 | 2 | 2 | 2 |
| DC169 | 4 | 1 | 2 | 4 | 4 | 4 | | | | |
| DC161 | 2 | | 2 | 2 | 2 | 2 | | | | |
| DC191 | 2-4 | | 2 | | | | 4 | 2 | 2-4 | 4 |
| DC170 | 4 | 2 | 2 | 4 | 4 | 4 | | | | |
| DC168 | 2 | 1 | 2 | 2 | 2 | 2 | | | | |
| DC167 | 8 | 4 | 8 | 16 | 16 | 16 | | | | |
| DC207 | 8 | | 4 | | | | 8 | 8 | 8-16 | 16-32 |
| DC213 | 4 | | 4 | | | | 32 | 4-8 | 4-8 | 4-8 |
| DC208 | 4-8 | | 2 | | | | 8 | 4 | 4 | 8 |
| DC209 | 2-4 | | 2 | | | | 2-4 | 1 | 2 | 2-4 |

The invention claimed is:

1. A compound characterized by a general formula (100)

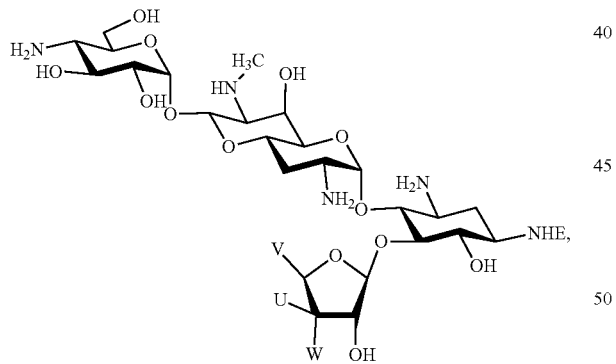

(100)

wherein

E is selected from H and (S)-4-amino-2-hydroxybutyryl, (S)-3-amino-2-hydroxypropionyl, —CON(OH)(CH$_2$)$_2$NH$_2$, (2R,4S)-2-hydroxy-4,5-diamino-pentanoyl, and (2S,4R)-2,5-dihydroxy-4-aminopentanoyl;

V is selected from H and CH$_2$-D, wherein

D is selected from OH, NH$_2$, NHCHO, NHR$^D$ and NHCONHR$^D$, wherein R$^D$ is selected from H, OH, unsubstituted or amino- and/or hydroxy-substituted C$_1$ to C$_6$ alkyl;

U and W are selected from the following alternatives:

one of U and W is —R$^W$ and the other one is selected from H, F and OH, or one of U and W is —OR$^W$ and the other one is H, wherein R$^W$ is selected from an amino- and/or hydroxy-substituted C$_1$ to C$_6$ alkyl, CH$_2$(CH$_2$)$_n$NH(CH$_2$)$_3$NH$_2$ and CH$_2$(CH$_2$)$_n$—R$^N$, wherein n is selected from 1, 2 or 3, R$^N$ is selected from NXY and a moiety characterized by formula (400)

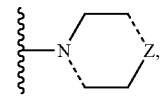

(400)

wherein

X and Y are independently selected from H, and unsubstituted or amino- and/or hydroxyl-substituted C$_1$ to C$_3$ alkyl, and Z is selected from O, NX and CH$_2$, or one of U and W is described by a moiety characterized by formula (300), (301), (304) or (305) and the other one of U and W is H

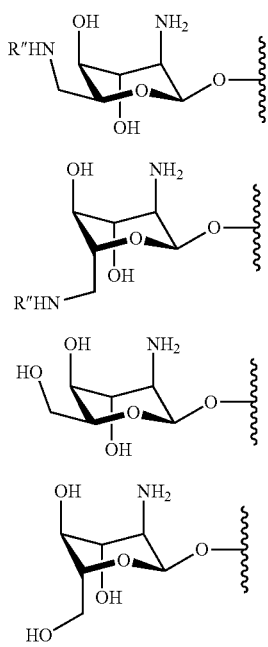

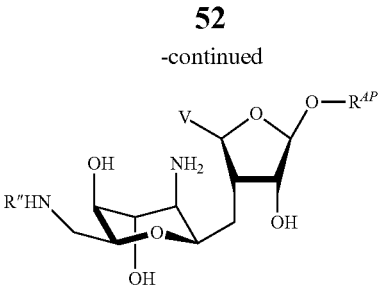

wherein R$^{AP}$ designates a moiety described by formula (2)

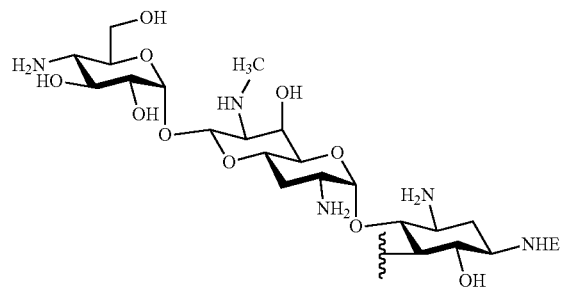

wherein R" is selected from H and an amino- and/or hydroxy-substituted C$_1$ to C$_6$ alkyl.

2. The compound according to claim 1, wherein V is selected from CH$_2$OH, H, CH$_2$NHCHO and CH$_2$NHCONH$_2$.

3. The compound according to claim 1, wherein V is CH$_2$NHR$^D$.

4. The compound according to claim 1, wherein E is H.

5. The compound according to claim 1, wherein one of U and W is —R$^W$ and the other one is selected from H, F, OH, or one of U and W is —OR$^W$ and the other one is H.

6. The compound according to claim 1, wherein R$^W$ is selected from (CH$_2$)$_2$OH, (CH$_2$)$_2$NH$_2$, (CH$_2$)$_2$NMe$_2$, (CH$_2$)$_2$NEt$_2$, (CH$_2$)$_2$NHMe, (CH$_2$)$_2$NHEt, (CH$_2$)$_3$OH, (CH$_2$)$_3$NH$_2$, (CH$_2$)$_3$NMe$_2$, (CH$_2$)$_3$NEt$_2$, (CH$_2$)$_3$NHMe, (CH$_2$)$_3$NHEt, CH$_2$CHOHCH$_2$OH, CH$_2$CHOHCH$_2$NH$_2$, CH$_2$CHOHCH$_2$NMe$_2$, CH$_2$CHOHCH$_2$NEt$_2$, CH$_2$CHOHCH$_2$NHMe and CH$_2$CHOHCH$_2$NHEt.

7. The compound according to claim 1, wherein
a. W is —R$^W$ and U is selected from H, F, OH, or
b. W is —OR$^W$ and U is H.

8. The compound according to claim 1, characterized by a general formula (112), (113) or (114)

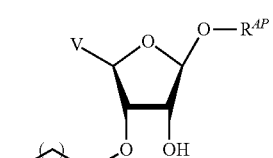

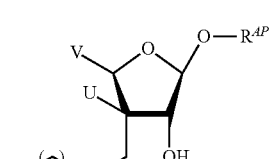

and ⸹ denotes the position where the apramycin backbone is attached to the compound described by general formula (112), (113), or (114),
wherein U is selected from OH and F and n, R", R$^N$ and V have the same meaning as indicated above.

9. The compound according to claim 8, characterized by the general formula
a. (112), E is H, R$^N$ is OH, V is CH$_2$OH and n is 1 [5—O-β-[3'''-O-(2-hydroxyethyl)-D-ribofuranosyl] apramycin; DCWSU178];
b. (112), E is H, R$^N$ is NH$_2$, V is CH$_2$NH$_2$ and n is 1 [5—O-β-[5-amino-3-O-(2-aminoethyl)-5-deoxy-D-ribofuranosyl] apramycin; DCWSU185];
c. (112), wherein E is H, V is CH$_2$NHCOH, R$^N$ is NH$_2$ and n is 1 [5—O-β-[3-O-(2-aminoethyl)-5-deoxy-5-formamido-D-ribofuranosyl] apramycin; DCWSU186].

10. The compound according to claim 1, wherein
a. E, U and V are H and W is —OR$^W$, and R$^W$ is selected from (CH$_2$)$_2$OH, (CH$_2$)$_2$NH$_2$, (CH$_2$)$_2$NMe$_2$, (CH$_2$)$_2$NEt$_2$, (CH$_2$)$_2$NHMe, (CH$_2$)$_2$NHEt, (CH$_2$)$_3$OH, (CH$_2$)$_3$NH$_2$, (CH$_2$)$_3$NMe$_2$, (CH$_2$)$_3$NEt$_2$, (CH$_2$)$_3$NHMe, (CH$_2$)$_3$NHEt, CH$_2$CHOHCH$_2$OH, CH$_2$CHOHCH$_2$NH$_2$, CH$_2$CHOHCH$_2$NMe$_2$, CH$_2$CHOHCH$_2$NEt$_2$, CH$_2$CHOHCH$_2$NHMe and CH$_2$CHOHCH$_2$NHEt; or
b. E and U are H, V is CH$_2$OH and W is a moiety described by formula (300), with R" selected from H, (CH$_2$)$_2$OH, (CH$_2$)$_2$NH$_2$, (CH$_2$)$_2$NMe$_2$, (CH$_2$)$_2$NEt$_2$, (CH$_2$)$_2$NHMe and (CH$_2$)$_3$NHEt.

11. The compound according to claim 1, wherein D is selected from OH, NHCHO and NHCONH$_2$.

12. The compound according to claim 1, wherein X and Y are independently selected from H, CH$_3$, CH$_2$CH$_3$, CH$_2$CH$_2$OH or CH$_2$CH$_2$NH$_2$.

13. The compound according to claim 1, wherein one of U and W is

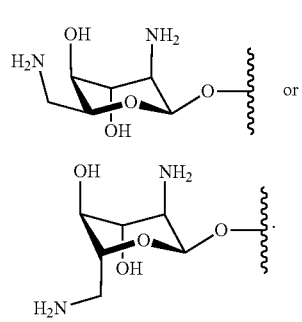
14. A method for treatment of a bacterial infection comprising:
   systemically administering to a subject in need thereof the compound of claim 1, wherein the infection is caused by a pathogen from family Enterobacteriaceae, thereby treating the bacterial infection.
* * * * *